US012781275B2

(12) United States Patent
Patel

(10) Patent No.: US 12,781,275 B2
(45) Date of Patent: Nov. 3, 2026

(54) MEASUREMENT OF NUCLEIC ACID

(71) Applicant: Abhijit Ajit Patel, Madison, CT (US)

(72) Inventor: Abhijit Ajit Patel, Madison, CT (US)

(73) Assignee: NATIONAL INSTITUTES OF HEALTH (NIH), U.S. DEPT. OF HEALTH AND HUMAN SERVICES (DHHS), U.S. GOVERNMENT, Bethesda, MD (US)

( * ) Notice: Subject to any disclaimer, the term of this patent is extended or adjusted under 35 U.S.C. 154(b) by 1249 days.

(21) Appl. No.: 17/105,188

(22) Filed: Nov. 25, 2020

(65) Prior Publication Data

US 2021/0214781 A1 Jul. 15, 2021

Related U.S. Application Data

(63) Continuation-in-part of application No. 15/544,834, filed as application No. PCT/US2016/017920 on Feb. 14, 2016, now abandoned.

(51) Int. Cl.

*C12Q 1/6869* (2018.01)
*C12Q 1/686* (2018.01)
*C12Q 1/6883* (2018.01)

(52) U.S. Cl.

CPC ........... *C12Q 1/6869* (2013.01); *C12Q 1/686* (2013.01); *C12Q 1/6883* (2013.01)

(58) Field of Classification Search

CPC .... C12Q 1/6869; C12Q 1/686; C12Q 1/6883; C12Q 2523/125; C12Q 2525/191

See application file for complete search history.

(56) References Cited

U.S. PATENT DOCUMENTS

| | | | | | |
|---|---|---|---|---|---|
| 2005/0196792 | A1 | 9/2005 | Fodor et al. | | |
| 2011/0201524 | A1* | 8/2011 | Kester | C12Q 1/6858 | 435/6.12 |
| 2014/0178881 | A1* | 6/2014 | Booth | C01G 55/002 | 435/6.11 |
| 2014/0322707 | A1* | 10/2014 | He | C12Q 1/6827 | 435/6.11 |
| 2018/0030528 | A1* | 2/2018 | Van Den Boom | G16B 20/10 | |
| 2019/0032148 | A1 | 1/2019 | Lewin et al. | | |

FOREIGN PATENT DOCUMENTS

| | | | | |
|---|---|---|---|---|
| CN | 110643702 | A | 1/2020 | |
| WO | WO-2015188192 | A2 * | 12/2015 | C12N 15/1068 |
| WO | WO2020243609 | A1 | 12/2020 | |
| WO | WO2022255944 | A2 | 12/2022 | |

OTHER PUBLICATIONS

International Search Report of PCT/US2024/035148 issued by KIPO on Oct. 14, 2024.

* cited by examiner

*Primary Examiner* — Sahana S Kaup

(74) *Attorney, Agent, or Firm* — Emerson, Thomson & Bennett, LLC; Roger D. Emerson; Peter R. Detorre

(57) ABSTRACT

The current document is directed to methods and compositions that enable simplified, sensitive, and accurate quantification of nucleic acids, including sequence variations and epigenetic modifications. Some methods enable highly sensitive measurement of low-abundance nucleic acid variants from a complex mixture of nucleic acid molecules.

9 Claims, 16 Drawing Sheets

Specification includes a Sequence Listing.

A

B

The above reaction can be performed in a single compartment (micro-well or droplet) in which there is a low probability of having more than one copy of any particular amplifiable genomic target region. Similar reactions, containing different compartment-specific tags, can be performed in parallel in many compartments.

MEASUREMENT OF NUCLEIC ACID

CROSS-REFERENCE TO RELATED APPLICATIONS

This application is a continuation-in-part of U.S. patent application Ser. No. 15/544,834, filed Jul. 19, 2017, which claims priority to PCT/US2016/017920, filed Feb. 14, 2016, which claims the benefit of U.S. Provisional Application No. 62/940,030, filed Nov. 25, 2019, which claims the benefit of U.S. Provisional Application No. 62/135,923, filed Mar. 20, 2015, and claims the benefit of U.S. Provisional Application No. 62/116,302, filed Feb. 13, 2015; the subject matter of all of which are hereby incorporated by reference as if fully set forth herein.

STATEMENT REGARDING FEDERALLY SPONSORED RESEARCH

This invention was made with government support under TR000140, TR000142, and R01CA197486 awarded by the National Institutes of Health. The government has certain rights in the invention.

TECHNICAL FIELD

The present document is related to identification and quantitation of nucleic acids in solutions.

BACKGROUND

Many applications in biomedical research and clinical medicine rely on accurate detection and quantitation of nucleic acids. Some applications rely on measurement of variant deoxyribonucleic acid ("DNA") or RNA sequences that indicate the presence genomic alterations such as point mutations, insertions, deletions, translocations, polymorphisms, or copy-number variations. Several challenges exist in the measurement of nucleic acids, from both technical and practical standpoints. Often, measurements must be made from large numbers of samples. Additionally, if very few copies of a particular nucleic acid sequence of interest are present in a limited sample containing a complex mixture of nucleic acid molecules, it can be challenging to reliably identify and quantify the low-abundance variants.

Achieving high analytical sensitivity for detection of rare variant sequences can be especially challenging in situations where the amount of DNA or RNA in a given sample is limited. An application of such a method is to detect small amounts of tumor-derived DNA or RNA molecules in the blood of individuals that have cancer. It is known that fragmented molecules of DNA and RNA are released into the bloodstream from dying cancer cells in patients with various types of malignancies. Such circulating tumor-derived nucleic acids are showing excellent promise as non-invasive cancer biomarkers. In the bloodstream, tumor-derived nucleic acids can be distinguished from normal background DNA or RNA based on the presence of tumor-specific mutations. However, such mutant nucleic acid copies are usually present in small amounts in a background of relatively abundant normal (wild-type) molecules. Often the mutant tumor-derived copies comprise less than 1% of the total DNA or RNA in plasma, and sometimes the abundance can be as low as 0.01% or lower. Thus, an assay with extremely high analytical sensitivity is required to detect and measure such low-abundance DNA or RNA.

The challenge of measuring low-abundance nucleic acid variants is further compounded when it is not known beforehand which somatic mutations are present in the patient's tumor (for example, in the setting of cancer screening). Without prior knowledge of the tumor's mutation profile, ultrasensitive detection of mutations in tumor-derived circulating nucleic acids requires broad and deep mutation coverage, robust error suppression, and efficient molecular sampling. For example, lung tumors have a median of ~150 non-synonymous mutations per tumor (driver and passenger mutations), and these mutations can occur in a broad range of possible genomic locations. Thus, to optimize detection sensitivity, a potential solution is to develop a sequencing-based assay that targets a large number of mutation-prone genomic regions with extremely deep coverage and maximal library yield. If mutation coverage is sufficiently broad, multiple mutant loci can be targeted for any given tumor, increasing the probability of finding at least one mutation in plasma. Importantly, an assay with such broad and deep coverage would require extremely robust suppression of analytical noise (sequencer errors, PCR errors, or DNA/RNA damage) occurring anywhere across the broadly targeted genomic regions. An additional strategy for detection of low-abundance tumor-derived DNA fragments is to measure tumor-specific epigenetic signatures, such as methylation or hydroxymethylation patterns in tumor-derived DNA. Because such cancer-specific epigenetic marks are found in multiple genomic regions of tumor-derived DNA, there is expected to be a greater concentration of informative tumor-derived DNA fragments in the circulation, potentially improving the ability to detect a cancer-specific signal.

SUMMARY

The current document is directed to methods and compositions that enable quantitation of low-abundance variant nucleic acid sequences from a complex mixture of nucleic acid molecules. Methods and compositions are described which permit very high-confidence mutation calls to be made from biological specimens containing very few mutant molecules by ensuring that the molecules are efficiently converted to next-generation sequencing libraries (with high conversion yield) and by applying stringent error suppression techniques to reduce analytical background noise. These methods can also be used to enable analysis of epigenetic modifications such as methylation and hydroxymethylation of cytosine bases with high confidence and without a need for comparison to reference genomic sequences. Methods and compositions are also described which improve the efficiency and simplicity of the analytical workflow, to permit higher throughput of samples and simultaneous analysis of multiple genomic regions while reducing cost and user effort.

DETAILED DESCRIPTION

Figure 1:
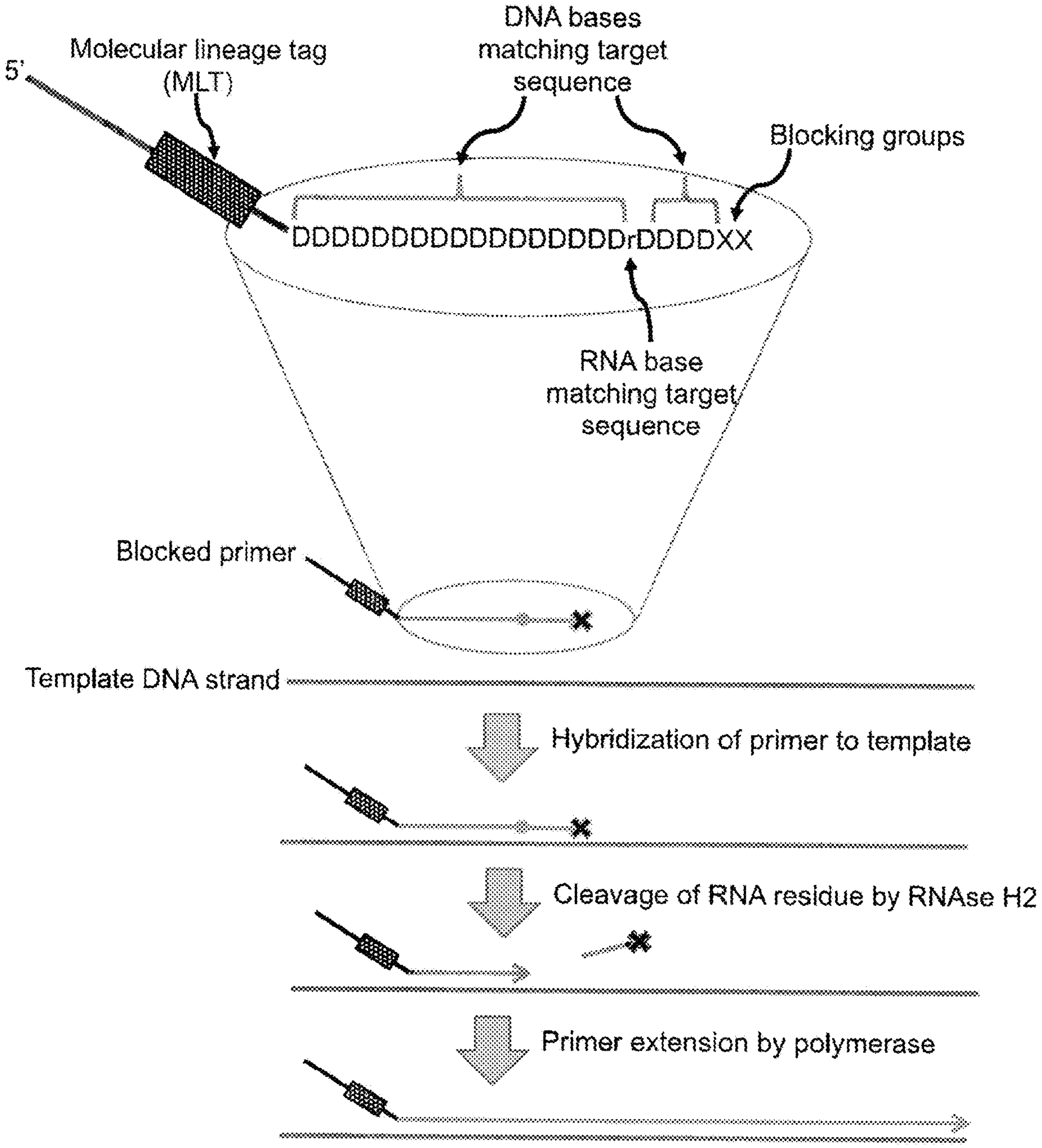
FIG. 1 shows a schematic of an RNAse H2-activatable primer that is designed to resist digestion of its terminal blocking groups by the 3' to 5' exonuclease activity of proofreading polymerases.

The current document is directed to methods and compositions relating to next-generation sequencing and medical diagnostics. Methods include identifying and quantifying nucleic acid variants, particularly those available in low abundance or those obscured by an abundance of wild-type sequences. The current document is also directed to methods related to identifying and quantifying specific sequences from a plurality of sequences amid a plurality of samples. The current document is also directed to detecting and distinguishing true nucleic acid variants from polymerase misincorporation errors, sequencer errors, and sample misclassification errors. In one implementation, methods include early attachment of barcodes and molecular lineage tags (MLTs) to targeted nucleic acids within a sample. Methods also include use of pairs of 3'-blocked primers that become unblocked upon highly specific hybridization to target DNA sequences, enabling assignment of MLTs while minimizing spurious amplification products during the polymerase chain reaction (PCR). Methods include raising the annealing temperature after the first few cycles of PCR to avoid participation of MLT-containing primers in later cycles of the reaction. Methods also include clonal overlapping paired-end sequencing to achieve sequence redundancy. Methods also include dividing of PCR amplifications into many small reaction compartments (such as aqueous droplets in oil or microscopic reaction volumes within a microfluidic device) to enable tracking of molecular lineage. Additional methods include amplification and tagging of both strands of a double-stranded DNA fragment within a microscopic reaction volume to improve analytical sensitivity by allowing mutations to be confirmed on both strands of a DNA duplex. Methods also include introduction of multiple copies of clonally tagged oligonucleotides into many small reaction volumes (e.g. micro-compartments) to facilitate compartment-specific tagging of the nucleic acid contents within the reaction volume. In one implementation, such clonally tagged oligonucleotides can be introduced to the compartments without needing to be attached to a surface such as a micro-bead or the compartment walls.

In one implementation, a method includes measuring nucleic acid variants by tagging and amplifying low abundance template nucleic acids in a multiplexed PCR. Low abundance template nucleic acids may be fetal DNA in the maternal circulation, circulating tumor DNA (ctDNA), circulating tumor RNA, exosome-derived RNA, viral RNA, viral DNA, DNA from a transplanted organ, or bacterial DNA. A multiplex PCR may include gene specific primers for a mutation prone genomic region. In one implementation, a mutation prone region may be within a gene that is altered in association with cancer.

In one implementation, primers comprise a barcode and/or a molecular lineage tag (MLT). In one implementation, a MLT can be 2-10 nucleotides. In another implementation, a MLT can be 6, 7, or 8 nucleotides. In one implementation, a barcode can identify the sample of origin of the template nucleic acid. In one implementation, a primer extension reaction employs targeted early barcoding. In targeted early barcoding, a plurality of different primers specific for different nucleic acid regions all have an identical barcode. An identical barcode identifies the nucleic acids from a particular sample. In one implementation, primers used for targeted early barcoding are produced by combining a unique barcode-containing oligonucleotide segment with a uniform mixture of gene-specific primer segments in a modular fashion.

In one implementation, disclosed assays can be used for clinical purposes. In one implementation, nucleic acid variants within blood can be identified and measured before and after treatment. In an example of cancer, a nucleic acid variant (e.g., cancer-related mutation) can be identified and/or measured prior to treatment (e.g., chemotherapy, radiation therapy, surgery, biologic therapy, combinations thereof). Then after treatment, the same nucleic acid variant can be identified or measured. After treatment, a quantitative change in the nucleic acid variant can indicate that the therapy was successful.

Explanation of the Phrase "Molecular Lineage Tag" ("MLT")

The phrase "molecular lineage tag" ("MLT") is used to refer to a stretch of sequence that is contained within a synthetic oligonucleotide (e.g. a primer) and is used to assign diverse sequence tags to copies of template nucleic acid molecules. Assignment of MLTs enables the lineage of copied (or amplified) DNA sequences to be traced to early copies made from template nucleic acid molecules during the first few cycles of PCR. A molecular lineage tag can contain degenerate and/or predefined DNA sequences, although a diverse population of tags is most easily achieved by incorporating several degenerate positions. A molecular lineage tag is designed to have between two and 14 degenerate base positions, but preferably has between six and eight base positions. The bases need not be consecutive, and can be separated by constant sequences. The number of possible MLT sequences that can be generated in a population of oligonucleotide molecules is generally determined by the length of the MLT sequence and the number of possible bases at each degenerate position. For example, if an MLT is eight bases long, and has an approximately equal probability of having A, C, G, or T at each position, then the number of possible sequences is 4^8=65,536. MLTs need not have sufficient diversity to ensure assignment of a completely unique sequence tag to each copied template molecule, but rather there should be a low probability of assigning any given MLT sequence to a particular molecule. The greater the number of possible MLT sequences, the lower the probability of any particular sequence being assigned to a given template molecule. When many template molecules are copied and tagged, it is possible that the same MLT sequence might be assigned to more than one template molecule. MLT sequences are used to track the lineage of molecules from initial copying through amplification, processing and sequencing. They can be used to distinguish sequences that arise from polymerase misincorporations or sequencer errors from sequences that are derived from true mutant template molecules. MLTs can also be used to identify when amplified PCR products were copied from a single DNA strand or more than one DNA strand (e.g. when a single copy of a template nucleic acid fragment is amplified within a small reaction compartment). MLTs can also be used to distinguish sequences that have the wrong barcode assignment as a result of cross-over of barcodes during pooled amplification.

The phrase "molecular lineage tagging" refers to the process of assigning molecular lineage tags to nucleic acid templates molecules. MLTs can be incorporated within primers, and can be attached to copies made from targeted template nucleic acid fragments by specific extension of primers on the templates.

Quantification of Low-Abundance Nucleic Acid Variants:

Methods and compositions are disclosed that identify and quantify nucleic acid sequence variants. Methods are disclosed that identify and quantify low-abundance sequence variants from complex mixtures of DNA or RNA. The methods can measure small amounts of tumor-derived DNA that can be found in the circulation of patients with various types of cancer.

Assessment of rare variant DNA sequences is important in many areas of biology and medicine. Small amounts of fetal DNA can be found in the circulation of pregnant women. One implementation includes analyzing rare fetal DNA that can be used to assess disease-associated genetic features or the sex of the fetus. An organ that is undergoing rejection by the recipient can release small amounts of DNA into the blood, and this donor-derived DNA can be distinguished based on genetic differences between the donor and the recipient. One implementation includes measuring donor-derived DNA to provide information about organ rejection and efficacy of treatment. In another implementation, nucleic acids can be detected from an infectious agent (e.g., bacteria, virus, fungus, parasite, etc.) in a patient sample. Genetic information about variations in pathogen-derived nucleic acids can help to better characterize the infection and to guide treatment decisions. For instance, detection of antibiotic resistance genes in the bacterial genome infecting a patient can direct antibiotic treatments.

Detection and measurement of low-abundance mutations has many important applications in the field of oncology. Tumors are known to acquire somatic mutations, some of which promote the unregulated proliferation of cancer cells. Identifying and quantifying such mutations has become a key diagnostic goal in the field of oncology. Companion diagnostics have become an important tool in identifying the mutational cause of cancer and then administering effective therapy for that particular mutation. Furthermore, some tumors acquire new mutations that confer resistance to targeted therapies. Thus, accurate determination of a tumor's mutation status can be a critical factor in determining the appropriateness of particular therapies for a given patient. However, detecting tumor-specific somatic mutations can be difficult, especially if tumor tissue obtained from a biopsy or a resection specimen has few tumor cells in a large background of stromal cells. Tumor-derived mutant DNA can be even more challenging to measure when it is found in very small amounts in blood, sputum, urine, stool, pleural fluid, or other biological samples.

Tumor-derived DNA is released into the bloodstream from dying cancer cells in patients with various types of malignancies. Detection of circulating tumor DNA (ctDNA) has several applications including, but not limited to, detecting presence of a malignancy, informing a prognosis, assessing treatment efficacy, tracking changes in tumor mutation status, and monitoring for disease recurrence or progression. Since unique somatic mutations can be used to distinguish tumor-derived DNA from normal background DNA in plasma, such circulating tumor-derived DNA represents a new class of highly specific cancer biomarkers with clinical applications that may complement those of conventional serum protein markers. In one implementation, methods include screening ctDNA for presence of tumor-specific, somatic mutations. In such implementations, false-positive results are expected to be very rare since it would be very unlikely to find cancer-related mutations in the plasma DNA of a healthy individual. Disclosed methods include methods that measure rare mutant DNA molecules that are shed into blood from cancer cells with high analytical sensitivity and specificity. Achieving extremely high detection sensitivity is especially important for detection of a small tumor at an early (and more curable) stage.

Since somatic mutations can occur at many possible locations within various cancer-related genes, a clinically useful test for analyzing ctDNA would need to be able to evaluate mutations in many genes simultaneously, and preferably from many samples simultaneously. Analysis of a plurality of mutation-prone regions from a plurality of samples allows more efficient use of large volumes of sequence data that can be obtained using massively parallel sequencing technologies. In one implementation, labeling molecules arising from a given sample with a sample-specific DNA sequence tag, also known as a barcode or index, facilitates simultaneous analysis of more than one sample. By using distinct barcode sequences to label molecules derived from different samples, it is possible to combine molecules and to carry out massively parallel sequencing on a mixture. Resultant sequences can then be sorted based on barcode identity to determine which sequences were derived from which samples. To minimize chances of misclassification, barcodes are designed so that any given barcode can be reliably distinguished from all other barcodes in the set by having distinct bases at a minimum of two positions.

In most protocols that are currently used to prepare samples for massively parallel sequencing, barcodes are attached after several steps of sample processing (e.g. purification, amplification, end repair, etc). Barcodes can be attached either by ligation of barcoded sequencing adapters or by incorporation of barcodes within primers that are used to make copies of nucleic acids of interest. Both approaches typically use several processing steps to be performed separately on nucleic acids derived from each sample before barcodes can be attached. Only after barcodes are attached can samples be mixed.

In one implementation, barcodes are assigned to targeted molecules at a very early step of sample processing. Targeted early barcode attachment not only permits sequencing of multiple samples to be performed in batch, it also enables most processing steps to be performed in a combined reaction volume. Once barcodes are attached to nucleic acid molecules in a sample-specific manner, molecules can be mixed, and all subsequent steps can be carried out in a single tube. If a large number of samples are analyzed, targeted early barcoding can greatly simplify the workflow. Since all molecules can be processed under identical conditions in a single tube, the molecules would experience uniform experimental conditions, and inter-sample variations would be minimized. In one implementation, tagging of nucleic acids from different samples can be achieved in consistent proportions and then used to enable quantitative comparisons of nucleic acid concentrations across samples. Thus, early barcoding can be used to quantify a total amount of various targeted nucleic acids, and not just variants, across many samples.

In one implementation, well-defined mixtures of primers are produced containing combinations of sample-specific barcodes and consistent ratios of gene-specific segments. Such primers can be used for targeted early barcoding and subsequent batched sample processing. These primers can also be used for quantitation of DNA or RNA in different samples. In one implementation, such primers allow parallel processing and analysis of multiple mutation-prone genomic target regions from multiple samples in a simplified and uniform manner.

Currently disclosed methods include methods that accurately quantify mutant DNA rather than simply determining its presence or absence. In one implementation, an amount of mutant DNA provides information about tumor burden and prognosis. Currently disclosed methods are capable of analyzing DNA that is highly fragmented due to degradation by blood-borne nucleases as well as due to degradation upon release from cells undergoing apoptotic death. Since somatic mutations can occur at many possible locations within various cancer-related genes, one implementation can evaluate mutations in many genes simultaneously from a given sample. Currently disclosed methods are capable of finding mutations in ctDNA without knowing beforehand which mutations are present in a patient's tumor. One implementation is able to screen for many different types of cancer by evaluating multiple regions of genomic DNA that are prone to developing tumor-specific somatic mutations. One implementation includes multiple samples combined together in the same reaction tube to minimize inter-sample variations.

Currently disclosed methods also include methods to identify epigenetic modifications in DNA fragments, such as methylation or hydroxymethylation of cytosine bases. In one implementation, epigenetic modifications can be identified without need for comparison to reference genomic sequences. In one implementation, epigenetic modifications can be identified on both paired strands of double-stranded DNA fragments, for example, enabling characterization of four possible methylation states at a CpG site: (1) methylation on cytosines of both strands, (2) methylation of cytosine on the + strand (3) methylation of cytosine on the − strand, and (4) methylation of cytosine on neither strand. In one implementation methylated or hydroxymethylated cytosines can be identified by bisulfite treatment or enzymatic treatment of DNA. In one implementation, comparison of bisulfite converted or enzymatically converted sequences from paired strands of a double-stranded DNA fragment can be used to disambiguate cytosines, thymines, and epigenetically modified cytosines in the original, biologically-derived DNA fragments. In one implementation, comparison of paired-strand sequences enables identification of DNA sequence positions at which a cytosine was converted to a thymine (because the opposite strand would have a guanine base at the complementary position). In one implementation, comparison of paired-strand sequences enables highly confident sequence determination of unmodified DNA bases as well as epigenetically modified bases. In one implementation, epigenetic modifications can be measured in DNA derived from human plasma (cell-free DNA) or from tumor tissue. In one implementation cancer-specific epigenetic modification patterns can be used to identify and measure tumor-derived DNA in the blood of patients with cancer. Such measurements could be used to screen patients for cancer, to diagnose the presence of residual cancer after treatment, to assess therapeutic response, or to monitor cancer recurrence or progression. Measurements of epigenetic patterns could also be used to assess tumor heterogeneity or the biological aggressiveness or prognosis of a cancer. Measurements of epigenetic patterns in tumor DNA could also be used to predict efficacy of various therapies such as chemotherapy, radiation therapy, immunotherapy, or targeted/biological therapy.

Although the currently described methods have been optimized for measurement of small amounts of mutant or epigenetically altered circulating tumor DNA (ctDNA) in a background of normal (wild-type) cell-free DNA in the plasma or serum of a patient having cancer, it is understood that they could be applied more broadly to the analysis of nucleic acid variants or epigenetic modifications from a variety of sources. Examples of such sources include, but are not limited to lymph nodes, tumor margins, pleural fluid, urine, stool, serum, bone marrow, peripheral white blood cells, cheek swabs, circulating tumor cells, cerebrospinal fluid, peritoneal fluid, amniotic fluid, cystic fluid, frozen tumor specimens, and tumor specimens that have been formalin-fixed and paraffin-embedded.

Methods:

Utility and Composition of Modular Primer Mixes:

Modular primer mixes can be used to assign sample-specific tags to targeted nucleic acid molecules (e.g., cDNA copied from RNA templates). However, such modular primer mixes can have a broad range of other uses. They can be used, more generally, to assign tags that could aid in identifying, categorizing, classifying, sorting, counting, or determining the distribution or frequency of targeted nucleic acid molecules (RNA or DNA). A modular primer mix is a mixture of primers having multiple distinct target-specific sequences in the 3' segment, and having a unique tag sequence in the 5' segment. Often, several modular primer mixes are made as a set, such that each primer mix has a distinct tag, and all mixes have the same composition of target-specific sequences. When the numbers of targets and tags become large, it can be impractical to individually synthesize primers and then mix them.

The tags (also referred to as barcodes or labels) that are incorporated into modular primer mixes may consist of arbitrary sequences, but typically include pre-defined sequences that can be reliably differentiated from each other. For example, in the RNA profiling method, each tag was designed to differ from all other tags in the set by at least two nucleotide positions so that sequencing errors would rarely lead to misclassification of tags. Tags need not be contained within a single, contiguous stretch of bases. In certain implementations, nucleotide positions comprising tag sequences can be distributed across non-contiguous regions of the 5' segments of modular primer mixes. Tags can also contain random or degenerate positions (A degenerate position is one at which, for example, the four nucleotides A, T, C, and G are incorporated with equal probability during oligonucleotide synthesis). However, tags within modular primer mixes must contain at least some positions having pre-defined (not degenerate) sequences.

Within modular primer mixes, tags need not be sample-specific. For example, a tag can be assigned to a sample, a molecule, a location, or a compartment. A tag can also be assigned to a set of samples, a set of molecules, a set of locations, or a set of compartments. Depending on the application, the assignment of tags could be random (e.g. any tag is randomly assigned to any sample, molecule, location, or compartment), or it could be pre-determined (e.g. one can decide to assign a particular tag to a particular sample, molecule, location, or compartment). Unique assignment of tags is not always necessary. For some applications each sample, molecule, location, or compartment must be assigned a unique tag. For some other applications it is acceptable for a given tag to be assigned to more than one sample, molecule, location, or compartment.

In some applications, more than one modular primer mix can be used to label a target or set of targets. For example, modular primer mixes could be used as both forward and reverse primer sets in a PCR amplification reaction, permitting assignment of two distinct tags to a target. A large diversity of labels can be achieved by using various combinations of tagged forward and reverse primer mixes.

Quantitation of Low-Abundance Mutant DNA from Complex Mixtures

Isolation of Template DNA:

Methods for purification or isolation of DNA or RNA from various clinical or experimental specimens are disclosed. Many kits and reagents are commercially available to facilitate nucleic acid purification. Depending on the type of sample to be analyzed, appropriate nucleic acid isolation techniques can be selected. Substances that might inhibit subsequent enzymatic reaction steps (such as polymerization) should be removed or reduced to non-inhibitory concentrations in purified DNA or RNA samples. Yield of nucleic should be maximized whenever possible. It would be disadvantageous to lose DNA during purification, since the lost DNA might include rare variant DNA. When isolating DNA from plasma, about 1 ng to 100 ng of cell-free DNA can be purified from 1 mL of plasma, which corresponds to about 350 to 35,000 genome copies. DNA yields can vary dramatically, especially in patients with an ongoing disease process such as cancer.

In one implementation, DNA can also be analyzed from other sample types, including but not limited to the following: pleural fluid, urine, stool, serum, bone marrow, peripheral white blood cells, circulating tumor cells, cerebrospinal fluid, peritoneal fluid, amniotic fluid, cystic fluid, lymph nodes, frozen tumor specimens, and tumor specimens that have been formalin-fixed and paraffin-embedded.

Lineage-Traced PCR

Figure 2:
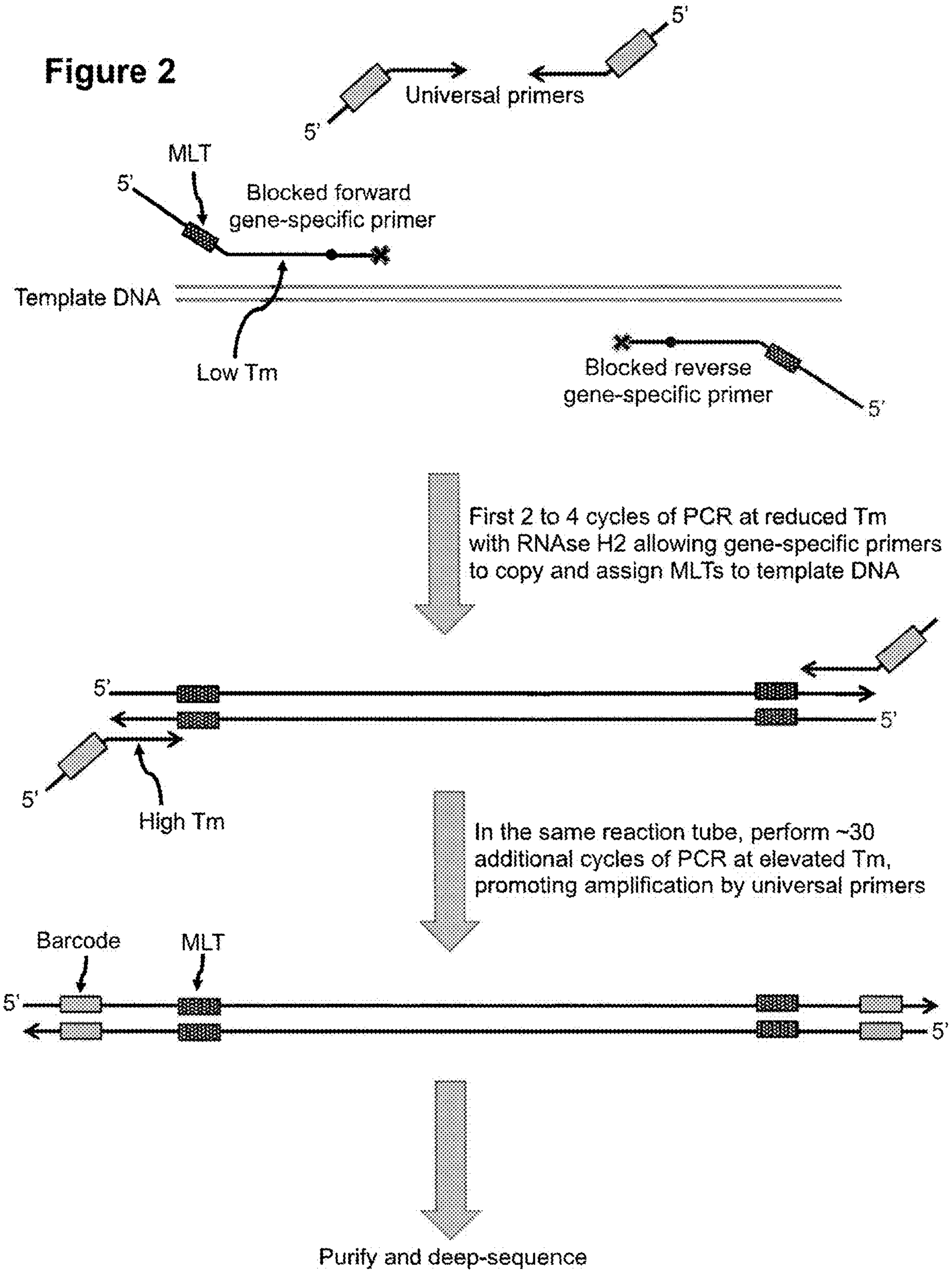
FIG. 2 provides a schematic description of Lineage-Traced PCR.

In one implementation, methods are provided that enable targeted template DNA molecules to be labeled with “molecular lineage tags” (MLTs) using gene-specific primers, and that enable these tagged copies to then be further copied (amplified) using universal primers. In one implementation, this reaction is performed in a single reaction volume without transferring reagents, which offers a significant advantage of procedural simplicity. As illustrated in FIG. 2, several gene-specific primers containing MLT sequences are used to simultaneously copy and label multiple targeted genomic regions of interest (e.g., regions that are prone to somatic mutations in cancer). The gene-specific primers have a melting temperature (for hybridization to the target gene sequence) that is lower than the melting temperature of the universal primers. Copying of targeted template DNA fragments and assignment of MLT sequences is promoted by using a lower annealing temperature during the first few (two to four) cycles of PCR. In subsequent PCR cycles, the annealing temperature is raised to discourage further participation of the MLT-containing gene-specific primers in the reaction. The 5' portion of the forward gene-specific primers contains a common sequence that is identical to the 3' portion of the forward universal primer sequence. The 5' portion of the reverse gene-specific primers contains a second (different) common sequence that is identical to the 3' portion of the reverse universal primer sequence.

The universal primer sequences are designed to have a higher melting temperature than the gene-specific primers. In one implementation, universal primers can be modified with nucleotide analogs at some positions to increase the stability of hybridization, such as locked nucleic acid (LNA) residues. Alternatively, universal primers can simply have a longer sequence and/or greater G/C content to increase the melting temperature. During the later cycles of PCR (after the first two to four cycles) the annealing temperature of thermal cycling can be raised to a level at which universal primers can efficiently hybridize, but gene-specific primers cannot. Thus, the MLT labeled copies which are generated in the first few PCR cycles become amplified and should comprise a large portion of the amplicon sequences.

In one implementation, the gene-specific primers would be present in the PCR cocktail in relatively low concentration (~10 to ~50 nM each), whereas the barcoded universal primers would be present in higher concentration (~200 to ~500 nM each). In one implementation, short universal primers lacking a barcode and adapter sequence could also be added to the cocktail in a relatively high concentration (~100 nM to 500 nM each). To allow sufficient time for hybridization and extension of the low-concentration gene-specific primers, a longer annealing time can be used for the first few PCR cycles, with optional slow cooling to the annealing temperature. During subsequent PCR cycles, a faster annealing time can be used because of the higher concentration of the universal primers.

Minimizing off-target hybridization and extension of gene-specific primers is critical to the success of this method. Because of the presence of universal primers within the same reaction cocktail, it is especially important to minimize hybridization and extension of gene specific primers with each other (i.e., formation of primer dimers). Even very small amounts of dimer formation among gene-specific primers can be catastrophic to the reaction, because those dimers can be exponentially copied and amplified by the universal primers. If the amplification of dimers dominates the reaction, the targeted gene regions may not be sufficiently amplified. To minimize off-target hybridization and extension of gene-specific primers, In one implementation, blocked gene-specific primers are used. The 3'-end of such primers is blocked with one or more residues that cannot be extended by a PCR polymerase. It is also important that the blocking group should not be digestible by the 3'-5' exonuclease activity of the polymerase. For this purpose, In one implementation, two nucleotides can be attached in the reverse orientation at the end of the primer (so that the penultimate linkage is 3'-3'). As illustrated in FIG. 1 a single RNA residue can be introduced into the DNA oligonucleotide, so that the blocking group can be cleaved off by thermostable RNAse H2 enzyme upon target-specific hybridization of the primer. Upon cleavage of the blocking group, the primer can be extended on its intended target. While some spurious hybridization and extension may still occur, such measures can minimize its impact on the reaction.

FIG. 1 shows a schematic of an RNAse H2-activatable primer that is designed to resist digestion of its terminal blocking groups by the 3' to 5' exonuclease activity of proofreading polymerases. Blocking groups are added to the 3'-end of the primer to prevent non-specific extension of the primer, especially to avoid formation of primer dimers. Upon specific hybridization of the primer to its target DNA sequence, a thermostable RNAse H2 enzyme can cleave the primer at its single RNA nucleotide, producing a 3' hydroxyl end that can then be extended by a polymerase. The positions indicated with a “D” represent DNA nucleotides that are complementary to the target sequence. The position indicated with an “r” represents an RNA nucleotide that is complementary to the target sequence. The blocking groups indicated by “XX” represent two nucleotides that are attached in reverse orientation (the penultimate linkage is a 3'-3' linkage, and the terminal “X” has a free 5' hydroxyl). The XX positions are synthesized using 5'-CE (beta-cyanoethyl) phosphoramidites. A dA-5' phosphoramidite was used, but one could also use dC-5', dT-5', or dG-5'. A polymerase will not extend from a 5' terminus, nor will its proofreading 3'-5' exonuclease activity digest such a terminus. In this example, the 5' region of the primer is depicted as having a degenerate molecular lineage tag and a universal primer sequence, but these features are optional and other features such as a sample-specific barcode could be included.

FIG. 2 provides a schematic description of Lineage-Traced PCR. The goal of Lineage-Traced PCR is to assign molecular lineage tags (MLTs) to template molecules during the first few cycles of PCR, and then to amplify these tagged copies using universal primers during subsequent PCR cycles (while minimizing incorporation of additional MLTs). This strategy can be used to differentiate true template-derived mutations from polymerase misincorporation errors and sequencer errors. The strategy can also be used to confirm that both strands of a double-stranded DNA template were tagged and amplified within a small reaction volume such as a droplet or micro-well. Lineage-traced PCR can be carried out in a single reaction volume or in multiple microscopic reaction volumes using a continuous thermal cycling program without transferring or adding reagents. The method uses gene-specific primers that have a low melting temperature (for example, 60° C.), and universal primers that have a higher melting temperature (for example, 72° C.). The gene-specific primers contain an MLT sequence as well as a universal primer sequence in their 5' region. At least the first two (but as many as the first four) cycles of PCR are carried out at a low Tm (e.g. 60° C.) to permit hybridization and extension of the MLT-containing gene-specific primers. For the subsequent ~30 cycles of PCR, a higher Tm is used (e.g. 72° C.) to promote preferential use of universal primers, and to minimize incorporation of additional MLTs. To avoid amplification of spurious products by the universal primers, it is imperative to minimize primer-dimer formation from the gene-specific primers. Thus scheme to enhance primer specificity must be employed, such as use of RNAse H2 activatable gene-specific primers. Universal primers could also be RNAse H2 activatable, although that is optional. Here the universal primers are shown to contain a sample-specific barcode, but this portion of the primer could be omitted, or other features could be incorporated depending on the intended application. Tm=melting temperature. MLT=molecular lineage tag.

Figure 3:
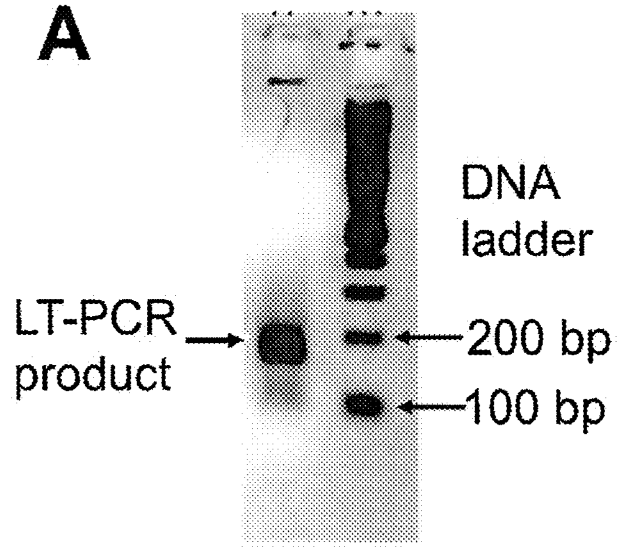
FIG. 3 shows results of lineage-traced PCR experiments.
Figure 3:
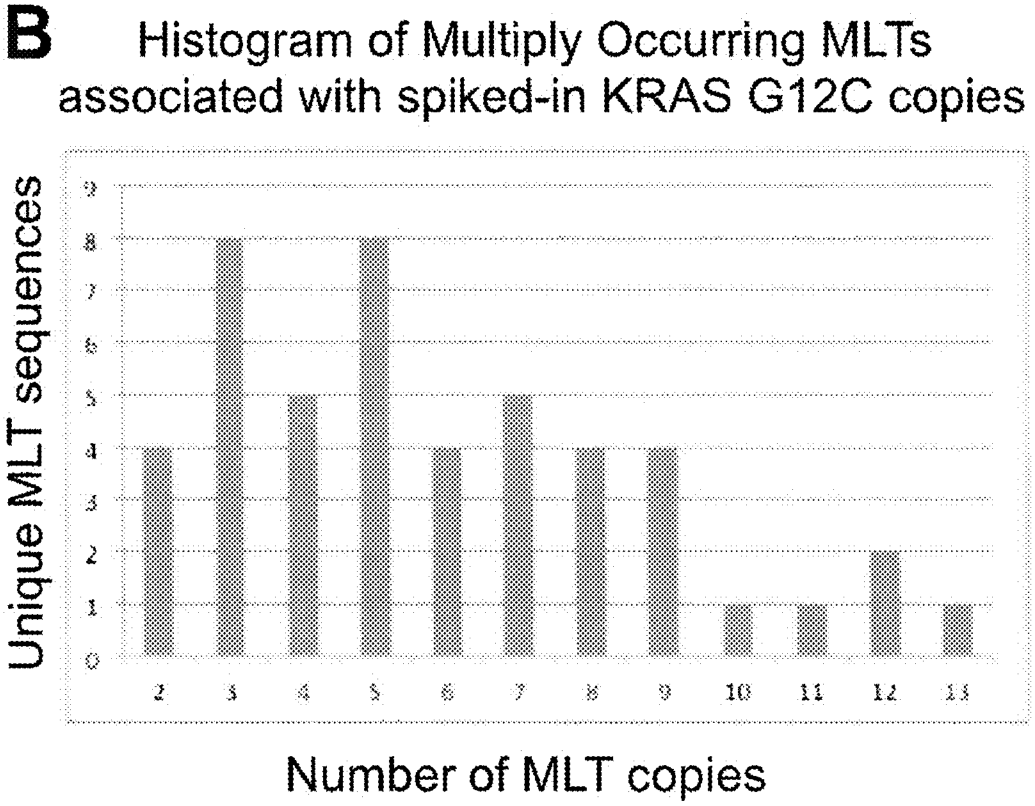

FIG. 3 shows results of lineage-traced PCR experiments. FIG. 3 (A) shows that amplification products from a single-tube lineage-traced PCR experiment produce a band migrating at the expected size on a 2% agarose gel. FIG. 3 (B) shows analysis of next-generation sequencing data generated from lineage-traced PCR amplification products shows an expected distribution pattern of MLT copies on a histogram. The analyzed sample consisted of ~20 genome equivalents of double-stranded DNA containing a known KRAS G12C mutation spiked into ~6000 genome equivalents of double-stranded wild-type DNA derived from healthy volunteer human plasma. The X-axis indicates the number of KRAS G12C mutant reads in which a given MLT sequence pair was found. The Y axis indicates the number of unique MLT sequence pairs (different tags) having a given number of read copies. Since approximately 20 double-stranded mutant DNA copies were added to the reaction, ~40 different MLT sequence pairs would be expected to have multiple read counts, as was observed.

In one implementation, the specificity of universal primers can also be enhanced by incorporating an RNAse H2-cleavable blocking group into the primers. In one implementation, universal primers can also be labeled with sample-specific barcodes, so that use of different barcoded primers for different samples would allow the PCR products to be pooled and subjected to next-generation sequencing in batch. The sequence data could then be sorted into sample-specific bins based on barcode identity. In one implementation, universal primers can also contain adapter sequences, which facilitate sequencing on a next-generation sequencing (NGS) platform of choice. In one implementation, a mixture of long (containing sample-specific barcode and adapter sequence) and short (lacking barcode and adapter) universal primers can be used. Because the short primers would have faster hybridization kinetics, they can enhance the efficiency of amplification during the early cycles of PCR.

In certain implementations, the DNA products are gel-purified to select products of the desired size and to eliminate unused primers before subjecting to massively parallel sequencing. In certain implementations, other approaches to purification could be used, including but not limited to hybrid capture using biotin-tagged complementary oligonucleotides, high-performance liquid chromatography, capillary electrophoresis, silica membrane partitioning, or binding to magnetic Solid Phase Reversible Immobilization (SPRI) beads.

In one implementation, a next-generation sequencer is used to obtain large numbers of sequences from the tagged, amplified, and purified PCR products. Clonal sequences (each sequence arising from a single nucleic acid molecule) produced by such a sequencer can be used to identify and quantify variant molecules using an approach known as ultra-deep sequencing. In principle, because large numbers of sequences can be obtained for each target site and for each sample, rare variants can be detected and measured. However, the error rate of the sequencer can limit the sensitivity of detection because such errors might be mistaken as true variants. To minimize the contribution of sequencer errors, One implementation uses clonal overlapping paired-end sequences. By separately sequencing opposite strands of DNA from each clonal population, and comparing the overlapping regions of the sequences, the vast majority of variants arising from sequencer errors can be eliminated. In one implementation, the region of sequence overlap is designed to be in the mutation-prone area. In one implementation, only read-pairs that perfectly match in the overlapping region are retained for further analysis. For such analysis, sequencers that produce clonal paired-end reads are useful. In certain implementations, other massively parallel sequencing platforms can also be utilized.

In one implementation, errors introduced during PCR amplification, processing, or sequencing can be distinguished from true template-derived mutant sequences by analyzing the distribution of molecular lineage tags (MLTs) associated with variant sequences. If the number of acquired NGS reads for a given target-sample bin is several-fold greater than the number of targeted template DNA copies within that sample, then an originally-assigned MLT would be expected to be present in multiple copies. Thus, if a mutant template DNA fragment were labeled with an MLT sequence during an early cycle of PCR, then the sequence data would be expected to contain multiple reads having that MLT sequence and the mutation. Conversely, variants arising from PCR errors or sequencer errors would be expected to contain fewer reads having the same MLT sequence (typically each MLT sequence would occur only once). In one implementation, MLTs can also be used to distinguish sequences bearing incorrect sample-specific barcodes due to cross-over events during pooled amplification.

Compartmentalized PCR Followed by NGS to Identify Matching Mutations on Both Strands of a DNA Duplex Although the lineage-traced PCR method described above can distinguish true template-derived mutations from most PCR errors and sequencer errors, it has difficulty identifying misincorporations that occur during the first few PCR cycles. Variant sequences arising from such an early misincorporation error can be associated with a relatively high number of MLT copies, similar to the multiple MLT copies expected for a true template-derived mutation. To improve upon this limitation, an alternative strategy for identifying template-derived mutations is to confirm that the same mutation exists on both strands of a given double-stranded template DNA fragment. Errors arising from PCR or from base damage of the template DNA would be very unlikely to produce complementary alterations on copies of both strands of the same template fragment.

Figure 7:
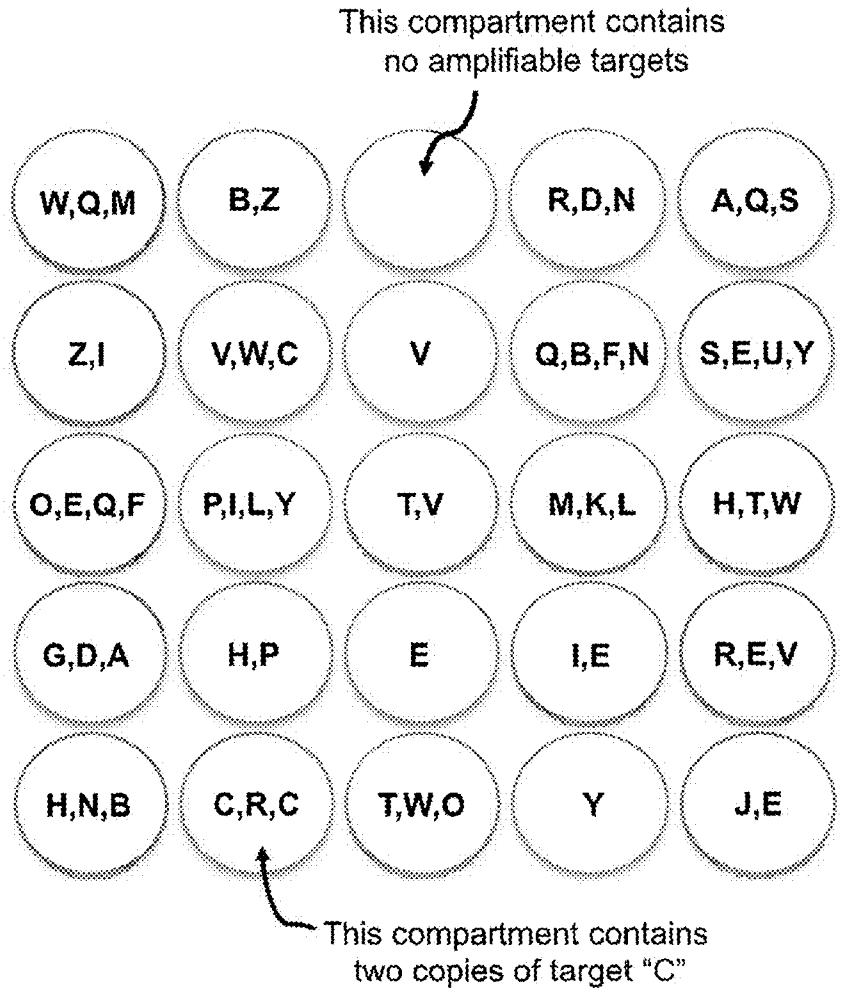
FIG. 7 shows an example of how different targets might be randomly compartmentalized within droplets or micro-wells for PCR amplification.

In one implementation, a compartmentalization, tagging, amplification, and sequencing strategy is used to verify that a mutation is present on both strands of a double-stranded template DNA fragment. In one implementation, the PCR reaction cocktail is similar to that used for lineage-traced PCR above (it contains universal primers and a mixture of RNAse H2-activatable gene-specific primers that contain MLT sequences). However, an important difference is that one of the long universal barcoded primers (either forward or reverse) is omitted from the cocktail so that primers containing a compartment-specific barcode can be used instead. In one implementation, the PCR reaction cocktail (including template DNA fragments) is divided into many microfluidic compartments so that any given compartment has a very low probability of containing more than one copy of a particular targeted template DNA fragment. As illustrated in FIG. 7, a compartment can have multiple amplifiable targeted fragments (different targets), but it should rarely have more than one copy of the same target. For example, if a copy of a given target is only found in approximately 1 out of 10 compartments, then the probability of finding two copies of that target in any given compartment would be ~1/100. All compartments contain universal primers and the full panel of gene-specific primers, so that all amplifiable targets within a compartment would be tagged, copied, and amplified. In one implementation, all compartments are simultaneously subjected to the same thermal cycling protocol (similar to that used for lineage-traced PCR).

FIG. 7 shows an example of how different targets might be randomly compartmentalized within droplets or micro-wells for PCR amplification. Each letter represents a targeted template DNA fragment, and each occurrence of a letter represents a single copy of that target. Compartmentalization of the amplification reaction is carried out such that typically zero or one (and occasionally two or more) copies of a given amplifiable, targeted template DNA fragment is present within a compartment. However, since multiple genomic regions are simultaneously targeted, several different targeted DNA fragments (usually in single copy each, occasionally in more than one copy) can be present within a compartment.

Figure 8:
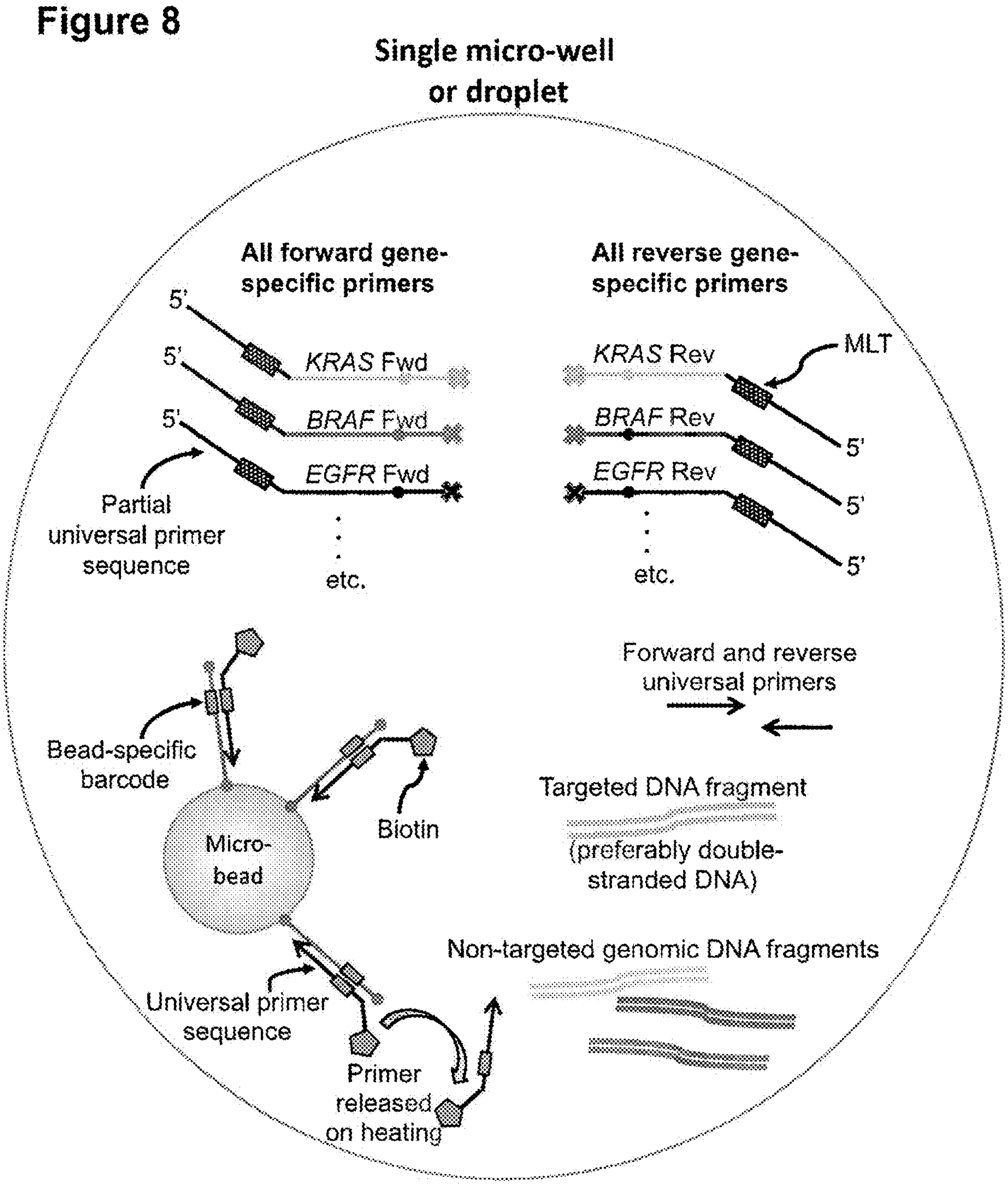
FIG. 8 shows an example of the contents of a single reaction compartment (such as a micro-well or a droplet).

FIG. 8 shows an example of the contents of a single reaction compartment (such as a micro-well or a droplet). Shown are MLT-containing gene-specific primers, universal primers, targeted template DNA fragments (and other non-targeted DNA fragments), and a bead carrying heat-releasable primers having a bead-specific barcode. In addition to this, the reaction compartment would contain reaction buffer, dNTPs, RNAse H2 enzyme, and polymerase (such as Phusion Hot Start). All compartments would contain the full panel of gene-specific primers. Each gene-specific primer contains an MLT sequence and it also has a portion of the universal primer sequence. Each gene-specific primer is present in relatively low concentration such as 5 to 50 nM. Universal primers are in high concentration (e.g. 200 to 500 nM). Barcoded primers released from the bead would be expected to have a relatively low concentration in the compartment (~5 to 50 nM). Double stranded DNA template fragments would allow the most robust error suppression, but single stranded templates could also be used. Any given micro-bead carries multiple copies of primers having the same bead-specific barcode. Since bead distribution within compartments is approximately random, many compartments would contain more than one micro-bead, and a minority of compartments would contain none (determined by Poisson statistics). In this example, biotin labeled amplification products would then be captured and isolated using streptavidin coated beads.

Figure 9:
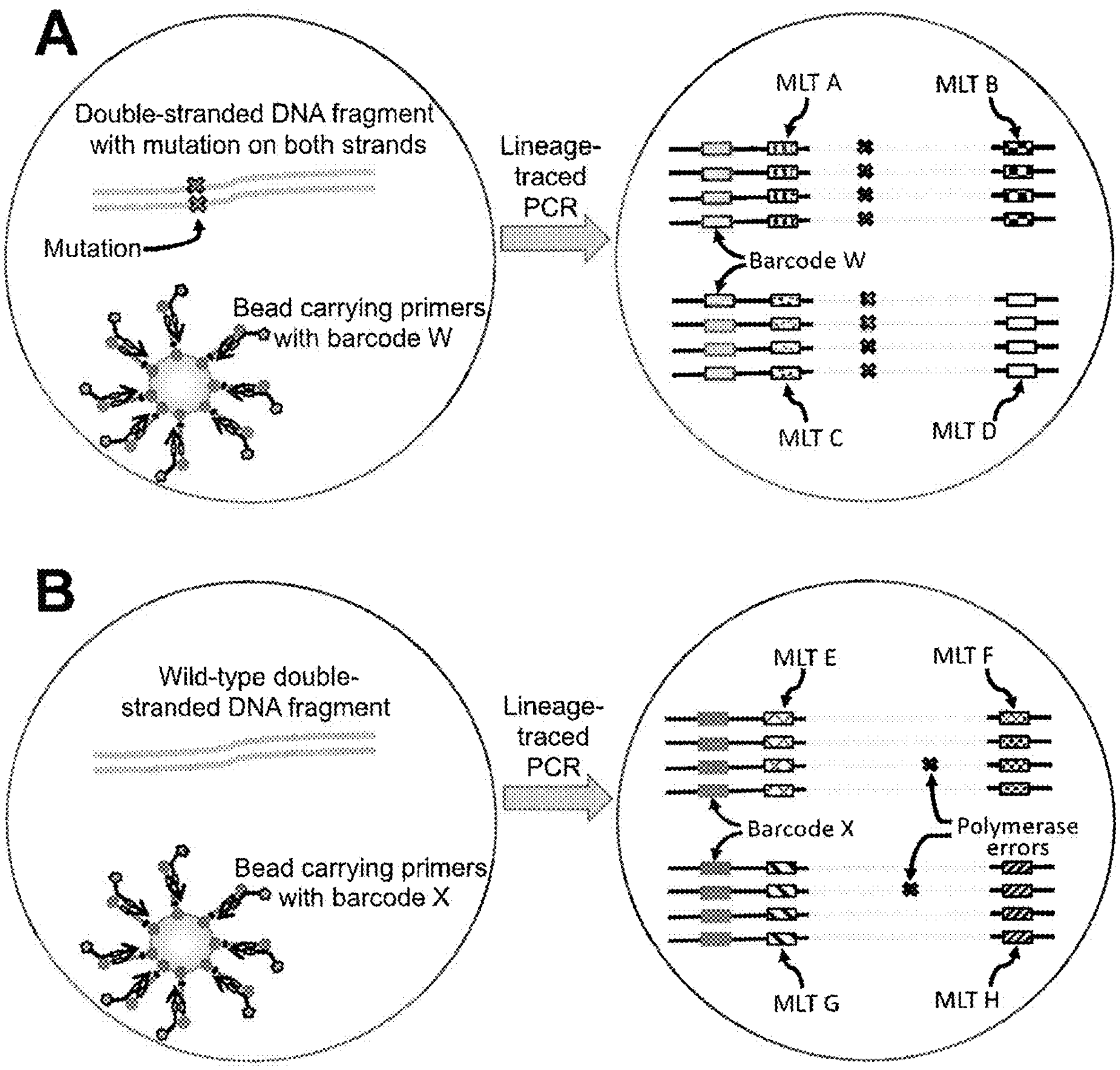
FIGS. 9A and B show two example scenarios of lineage-traced PCR being carried out within a micro-compartment containing a single microbead carrying barcoded primers.

FIGS. 9A and B show two example scenarios of lineage-traced PCR being carried out within a micro-compartment containing a single microbead carrying barcoded primers. Panel A depicts tagging and amplification of a double-stranded targeted DNA fragment that contains a true mutation on both strands of the duplex (the two strands of the duplex are perfectly complementary). In this case, the same bead-specific barcode is assigned to all amplification products. The presence of mutations in multiple reads containing two distinct MLT pairs (i.e. A-B, and C-D) indicates that the mutation was present on both strands of the template DNA. Panel B depicts similar tagging and amplification of a wild-type double-stranded DNA fragment. In this case, the amplification products contain a few polymerase errors, but when sequences are grouped by bead-specific barcode, no consistent mutation is seen. MLTs and barcodes labeled with different letters (e.g. MLT G or Barcode W) represent different nucleotide sequence tags. For simplicity, each tag or barcode is identified by a single letter of the alphabet, whereas in reality each tag typically consists of a stretch of six to ten bases.

Figure 10:
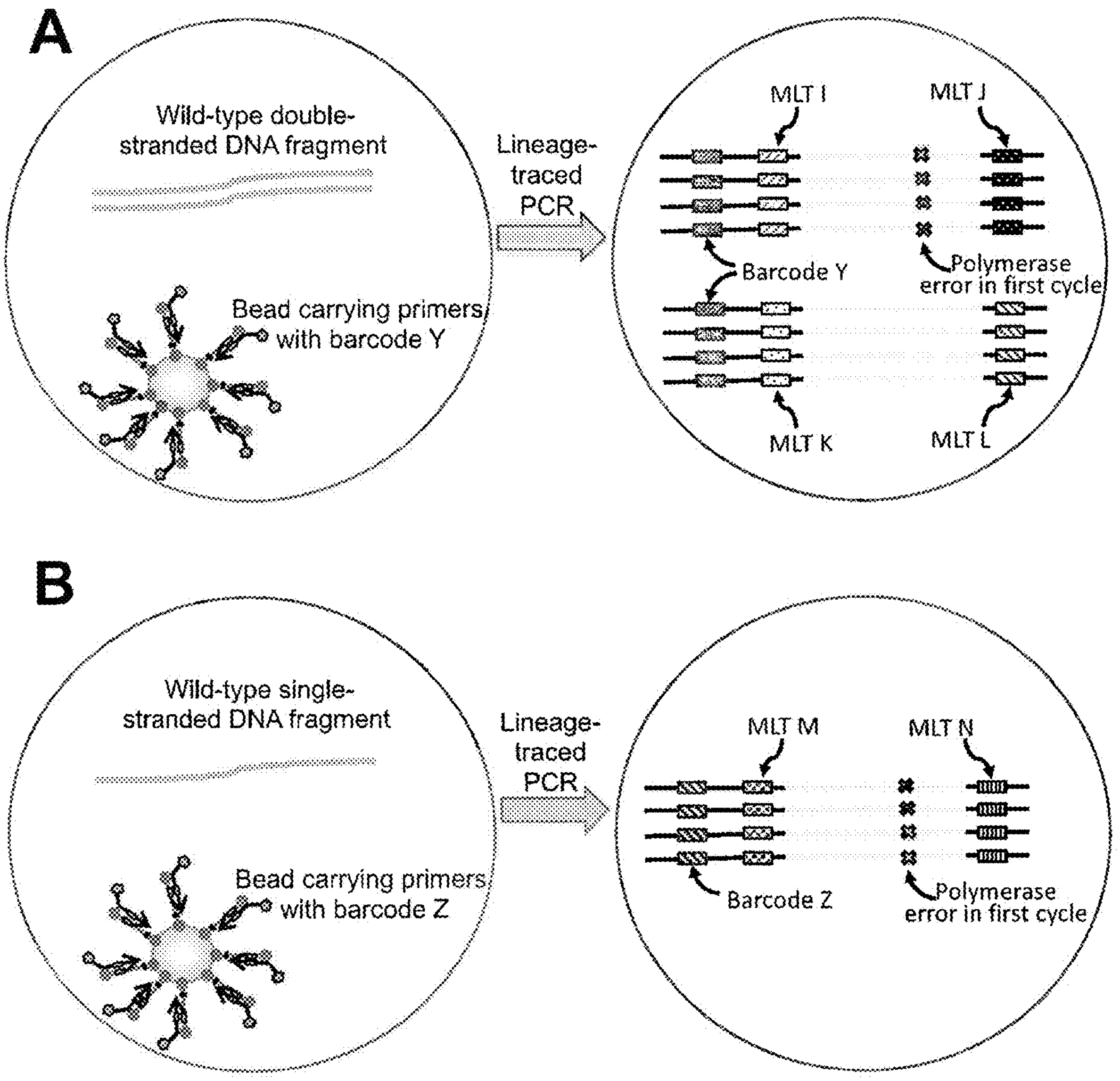
FIGS. 10A and B show two additional example scenarios of lineage-traced PCR being carried out within a micro-compartment containing a single microbead carrying barcoded primers.

FIGS. 10A and B show two additional example scenarios of lineage-traced PCR being carried out within a micro-compartment containing a single microbead carrying barcoded primers. Panel A depicts tagging and amplification of a wild-type double-stranded DNA fragment in which a polymerase misincorporation error occurred during the first cycle of PCR, when copying one of the two DNA template strands. This is shown as an extreme example of how an error could be distinguished even if it occurred during the first cycle of PCR. In this case, the amplification products show the error associated with only one of the two MLT pairs (i.e. I-J), not with both MLT pairs (i.e. I-J and K-L) as would be expected if a true mutation were copied from both strands of a template DNA duplex. Panel B depicts tagging and amplification of a wild-type single-stranded DNA fragment in which a polymerase misincorporation error occurred during the first cycle of PCR. In this case, although the error may be found in the entire population of amplified copies within that compartment (tagged with barcode Z), the copies all have a single MLT pair (i.e. M-N), not two (or more) MLT pairs as would be expected for a true mutation copied from both strands of a template DNA duplex.

Figure 11:
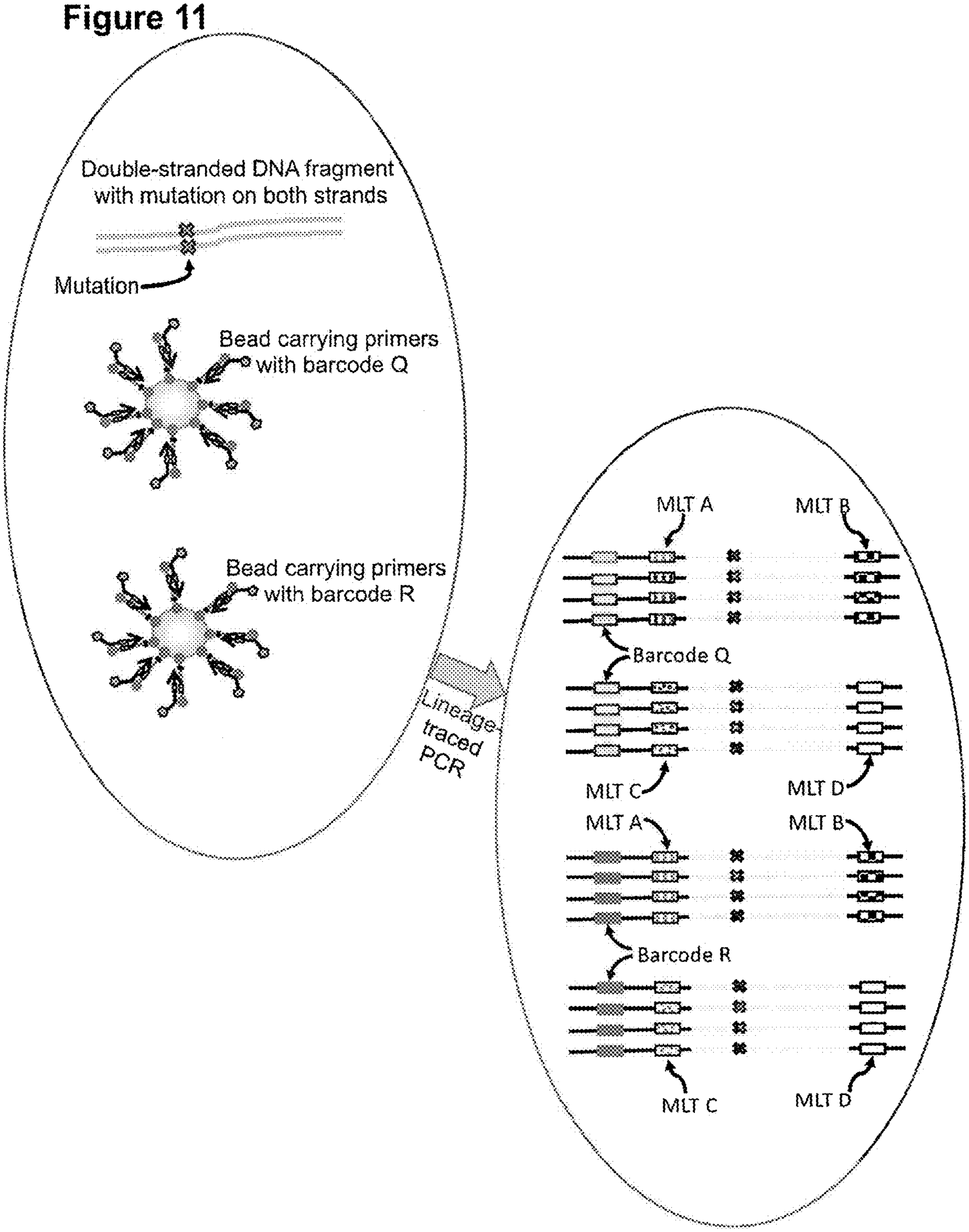
FIG. 11 illustrates how analysis of lineage-traced PCR within micro-compartments would be performed if there were two (or more) differently barcoded primers in a given compartment.

FIG. 11 illustrates how the analysis would be performed if there were two (or more) differently barcoded primers on two (or more) beads in a given compartment. Beads are expected to be distributed within different compartments according to a Poisson distribution, with some compartments containing zero beads, some compartments containing a single bead, and some compartments containing two or more. In order to reduce the number of compartments containing zero beads, one could aim to achieve a median of two or three beads per compartment. Alternatively, methods exist to overcome Poisson statistics to distribute a single bead into a single compartment, but these approaches involve complex microfluidic manipulations or pre-dispensing of primers into defined reaction chambers. Compartments in which more than one barcoded primer set is present can be identified during subsequent computational analysis of sequence data. Because a given MLT pair would have an extremely low probability of being found in sequences derived from more than one compartment, all compartment-specific barcodes associated with such a pair can be inferred to be derived from a single compartment.

In one implementation, molecular lineage tags (MLTs) are assigned to template molecules via gene-specific primers, and then these tagged copies are amplified by universal primers as was described for lineage-traced PCR. Within a compartment, if there is generally not more than one copy of a given targeted double-stranded template DNA fragment, then MLTs can be used to identify amplified sequences arising from copies of the two different strands (illustrated in FIG. 9). In one implementation, primers containing one or a few compartment-specific tags would be used to identify the amplicons produced within a given reaction compartment. Thus, using such a tagging scheme, it is possible to confirm that the same variant sequence was copied from two different strands of DNA within the same compartment.

The PCR cocktail can be divided into microfluidic compartments in various ways. In one implementation, the compartments can be as small at 10 picoliters and as large as 10 nanoliters. In certain implementations, the compartments are between ~0.1 to 1 nanoliter in volume. Ideally, the volume of the compartments for a given experiment should be uniform. The number of compartments can range from a few thousand to several million, depending on the application and the expected concentration of template DNA molecules. In one implementation, PCR compartments can be produced as droplets of PCR cocktail in oil using a microfluidic droplet generator device. Mineral oil can be used for this purpose or fluorinated oils can also be used. Surfactant can be used to stabilize the droplets and prevent coalescence of droplets before or during PCR. In one implementation, an emulsion of PCR cocktail in oil can also be made simply by vigorously agitating the mixture (but this approach has the disadvantage of creating non-uniform droplet sizes). In another implementation, the PCR cocktail can be compartmentalized into micro-wells on a microfluidic device. In one implementation, a slide containing patterned polydimethylsiloxane (PDMS) with thousands of nanoliter-sized wells can be used. In one implementation, a microfluidic device containing a narrow serpentine channel can be used in which reaction volumes are separated by oil or air. In one implementation, a similar microfluidic device can be used in which a PCR cocktail can be introduced into channels and then the channels can be divided into separate reaction chambers by simultaneously closing thousands of microvalves. In yet another implementation, a PCR cocktail can be compartmentalized into micro-wells on the surface of a wafer or chip made of silicon or plastic. In a preferred implementation, a silicon wafer can be etched using the established processes of photolithography and Deep Reactive Ion Etching (DRIE) to create an array of micro-wells in the silicon surface, such that each micro-well can accommodate a liquid volume of between 0.01 and 10 nanoliters, preferably between 0.1 and 5 nanoliters, and more preferably between 0.5 and 2 nanoliters. The micro-wells can be created by etching the silicon to a depth of between 10 and 500 micrometers, with a preferred depth of between 100 and 200 micrometers. The length and width of each micro-well can range between 10 micrometers and 500 micrometers, preferably between 20 and 150 micrometers. In one implementation, microwell dimensions of ~80 micrometers length, ~30 micrometers width, and ~150 micrometers depth have been used. Spacing between microwells can be between 1 and 500 micrometers, preferably between 10 and 60 micrometers. To make the silicon surface of the micro-wells compatible with PCR, the surface can be made bio-compatible, for example, by coating the surface of the micro-wells with silicon dioxide and/or polyethylene glycol. The PCR cocktail can be filled into the microwells, in one implementation, with the assistance of capillary force. The aqueous PCR cocktail in each micro-well can be isolated from the PCR cocktail in neighboring compartments by enclosing the top of the well with a solid or semisolid (flexible or compressible) material such as glass, plastic, rubber, or silicone. Preferably, the PCR cocktails in each micro-well can be isolated from neighboring micro-wells by adding oil on top of the microwells (such as Mineral Oil, Silicone Oil, or Fluorinated oils [e.g. FC-40 Fluorinert, Novec 7500, etc]). The oil can prevent transfer of aqueous PCR solution between micro-wells, and can reduce evaporation of aqueous solution during the thermal cycling that is required in PCR. A detailed description of how to produce PCR-compatible microwells in silicon wafers is provided in Example 3. PCR can be carried out by thermal cycling the micro-compartments simultaneously.

In one implementation, clonal primers containing a compartment-specific tag (or barcode) can be introduced to the compartments via a micro-bead. It is possible to produce a large population of micro-beads that each carry many copies of uniformly tagged primers, but a large diversity of tags exists on different beads. A given bead would carry a clonal population of tagged primers on its surface (all having the same tag), but different beads would carry primers having different tags. In one implementation, microbeads can be mixed with the PCR cocktail and can be compartmentalized with the cocktail. In one implementation, the concentration of beads would be adjusted so that an average of two or three beads would be delivered to each compartment (such that few compartments would have zero beads). The distribution of beads into compartments would be expected to follow Poisson statistics. In one implementation, primers can be released into the compartmentalized solution from the bead surface by heating (by melting the primer off from a complementary DNA strand attached to the bead). In another implementation, primers can be released into the compartmentalized solution from the bead surface by photocleavage (a photocleavable phosphoramidite can be used to link the oligonucleotide to the bead surface). In another implementation, the primers can remain attached to the beads and the hybridization and polymerization reactions can be performed on the bead surface. In one implementation, superparamagnetic beads can be used (coated with cross-linked polystyrene and surface activated with amine or hydroxyl groups). In other implementations, beads can be used that are composed of materials including but not limited to agarose, polyacrylamide, polystyrene, or polymethyl methacrylate. In one implementation, beads can be coated with streptavidin to bind to biotin-labeled oligonucleotides. In certain implementations, beads can be between 0.5 micrometers and 100 micrometers in size. In certain implementations, beads are between 1 micrometer and 5 micrometers in size. In certain implementations, beads used in a given experiment are a relatively uniform size and carry a relatively uniform number of primer copies on each bead.

Figure 4:
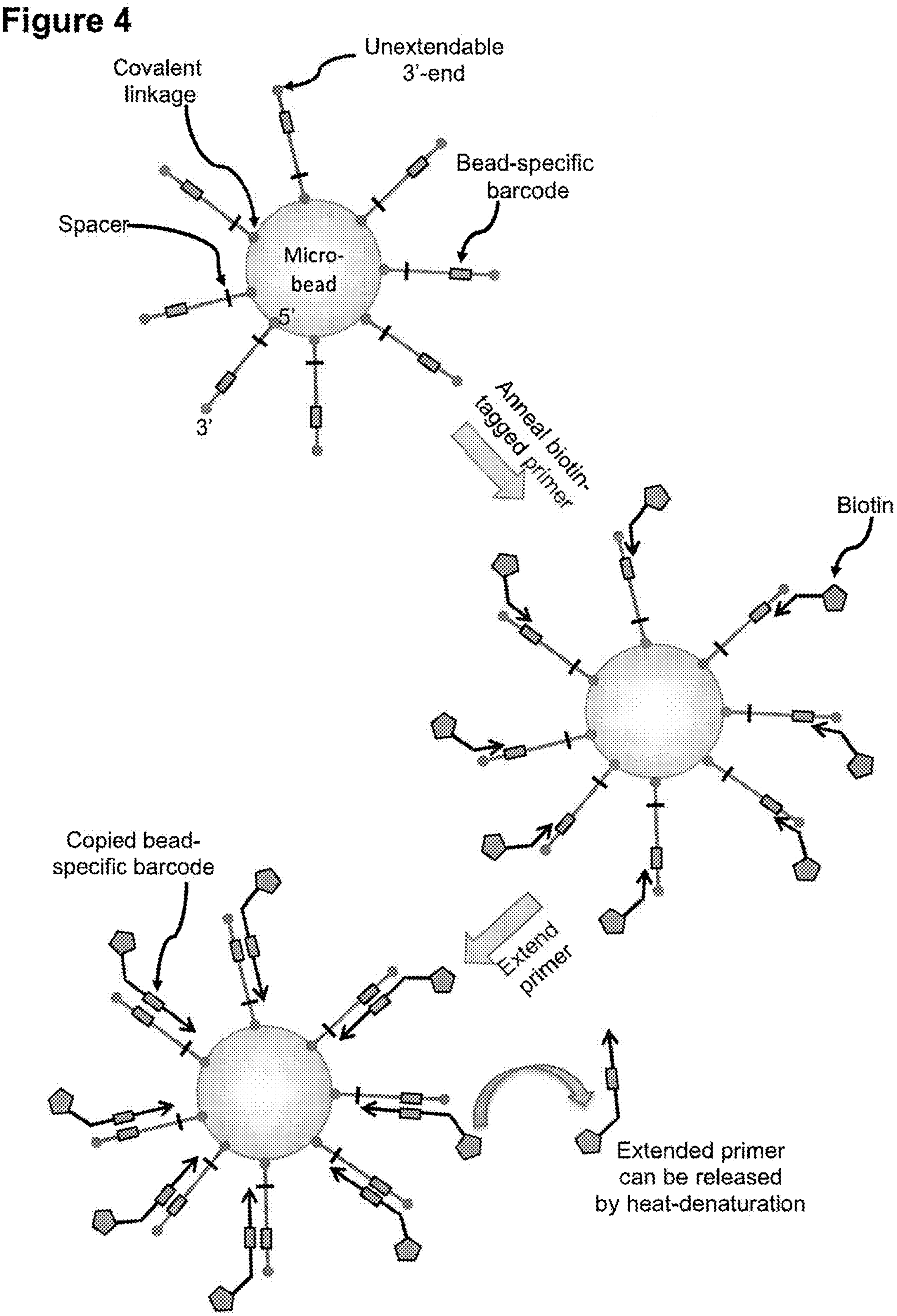
FIG. 4 shows an example of how heat-releasable primers containing bead-specific barcodes can be produced on microbeads.

FIG. 4 shows an example of how heat-releasable primers containing bead-specific barcodes can be produced on microbeads. First, oligonucleotides can be synthesized on the surface of microbeads using standard phosphoramidite chemistry on an automated oligonucleotide synthesizer. The microbead surface can be functionalized with, for example, amine or hydroxyl groups, which will form a covalent linkage with phosphoramidite monomers. Additional phosphoramidite monomers can then be added sequentially using standard synthesis protocols. Depending on the desired orientation of the bead-bound oligonucleotide, either standard or 5'-beta-cyanoethyl phosphoramidite monomers can be used. To introduce some distance between the oligonucleotide and the bead surface, one or multiple spacer phosphoramidites can be added to the bead surface before adding nucleotide monomers. Split and pool synthesis, as described in the methods section, can be used to incorporate bead-specific barcodes in the oligonucleotides. If microbeads are too small to be retained by the frits used in the columns of automated oligonucleotide synthesizers, one can use super-paramagnetic microbeads held in place by a magnet. A second oligonucleotide containing a common priming sequence (and an optional biotin group) can be used to copy the bead-bound oligonucleotide using a DNA polymerase. In this way, the extended primers would contain the bead-specific barcode sequences as well as the universal primer sequence. After the beads are compartmentalized into smaller reaction volumes such as droplets or micro-wells, the extended primer containing the bead-specific barcode can be released from the bead by heat-denaturation (e.g. during PCR). Other modes of primer release could also be used, such as photocleavage and chemical decoupling.

Figure 5:
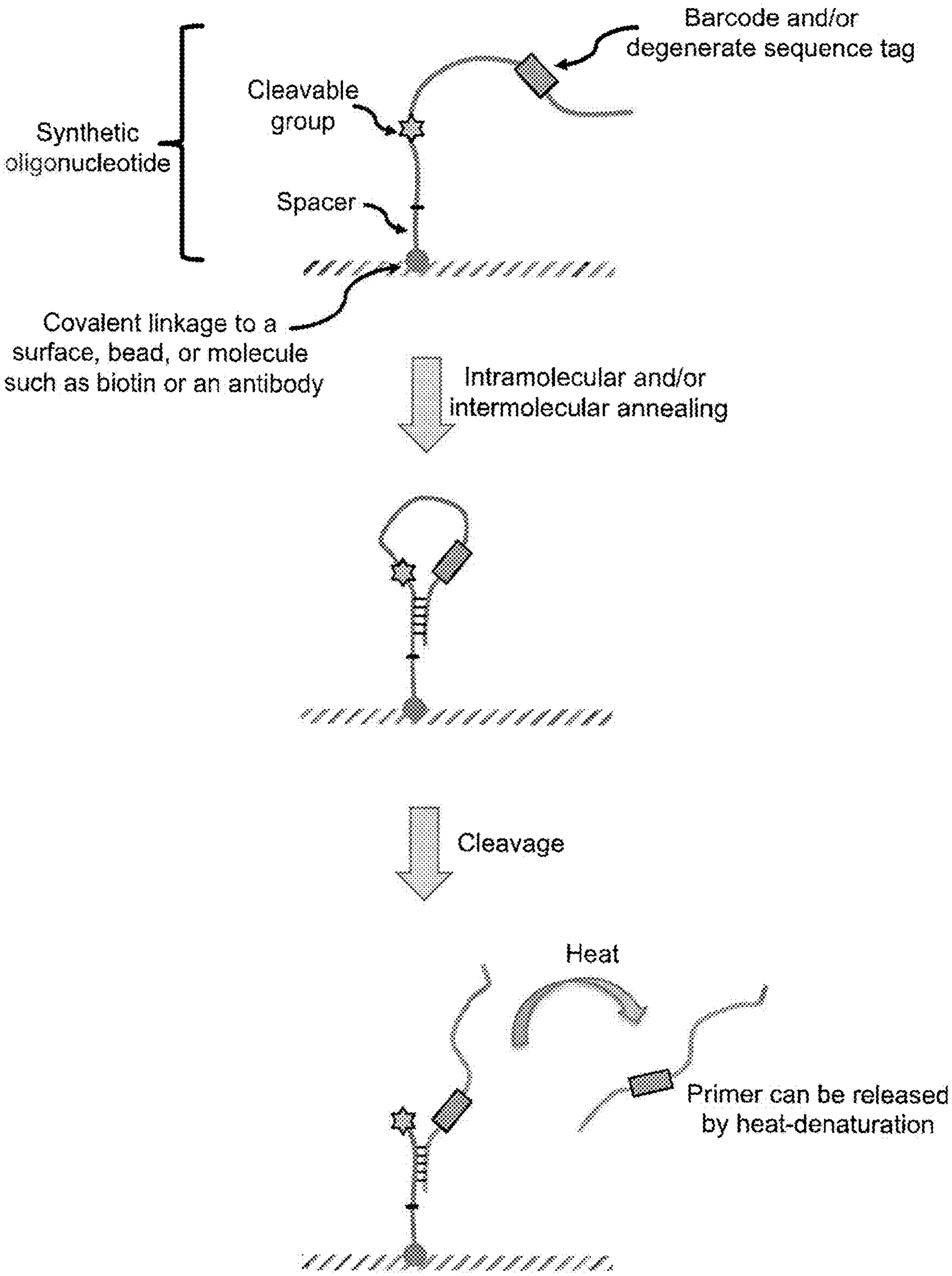
FIG. 5 shows a method for producing temporarily immobilized oligonucleotides that can be released by heat-denaturation.

FIG. 5 shows an alternative method for producing temporarily immobilized oligonucleotides that can be released by heat-denaturation. Oligonucleotides containing a cleavable group (for example, a photo-cleavable linker) can either be directly synthesized on a surface (such as a micro-bead) or can be coupled post-synthesis to a surface, particle, or molecule via a covalent bond or biotin affinity capture. A set of defined barcode sequences or degenerate tag sequences (such as MLTs) could be incorporated into the oligonucleotide. The tags could also be synthesized via split-and-pool synthesis to produce a large diversity of tags with multiple copies of the same tag on a given bead (or particle). The oligonucleotide is designed to have a region of self-complementarity, such that the cleaved oligonucleotide would remain attached via base-pairing interactions (hybridization). The oligonucleotide can be released into solution at a later time by heat-denaturation. The oligonucleotide can be synthesized in either the 5' to 3' or the 3' to 5' direction, depending on the downstream application.

In one implementation, a population of beads carrying a diverse set of clonally tagged primers (one bead, one tag) can be synthesized using a split-and-pool oligonucleotide synthesis approach. Common primer sequences can be synthesized using standard phosphoramidite chemistry on an automated oligonucleotide synthesizer. Primers can be synthesized in the 5' to 3' or the 3' to 5' direction, using the appropriate phosphoramidites. In one implementation, phosphoramidites can be covalently linked to the beads by using beads whose surface is modified with amine or hydroxyl groups. In one implementation, a permanent magnet or electromagnet can be used to retain magnetic microbeads within a synthesis column on an automated oligonucleotide synthesizer (since beads may be too small to be retained by a frit). In one implementation, a split-and-pool synthesis approach is used to produce a diversity of clonal tags on the beads. The common region of the primer is made, and then the synthesizer is paused at the beginning of the tag sequence. In one implementation, the beads are pooled and then split into four different fresh columns, and a different phosphoramidite (dA, dT, dC, or dG) is added to the four columns (one phosphoramidite per column). In another implementation, more or less than four columns and four phosphoramidites can be used (to increase or decrease the number of possible residues at a given position). After each coupling cycle within the tag region, the beads are pooled and re-distributed into fresh columns for the next cycle. In this way, the oligonucleotides coupled to a given bead receive the same base in a given cycle, but which base is added at a given position is randomly chosen. In one implementation, a bead-specific tag sequence can be between 1 and 15 bases in length. In certain implementations, a bead-specific tag sequence can be 8 to 12 bases in length. In one implementation, a complementary primer can be hybridized to the bead-bound oligonucleotide and extended using a polymerase to copy the tag sequence and additional primer sequence as schematized in FIG. 4. The extended primer would serve as a heat-releasable primer having a bead-specific barcode. In one implementation, this heat-releasable barcoded primer can be used to hybridize and extend on the PCR amplified targets within the compartment (the 3'-end of the heat-releasable primers would contain a portion of the universal primer sequence to facilitate hybridization with the targeted amplicons).

In another implementation, primers containing compartment-specific tags can be pre-distributed within compartments. For example, if a PCR cocktail is to be divided into micro-wells on a microfluidic device, primers containing compartment-specific tags can be added to each micro-well before adding the PCR cocktail. In one implementation, primers could be chemically coupled to the surface or the wall of a micro-well, or coupled via a biotin-streptavidin interaction. In one implementation, primers could be released from the microwell by heating (by melting off of an immobilized complementary oligonucleotide as described above), by photocleavage, or other means. In one implementation, primers could remain attached to the surface of the well, and polymerization could be carried out on the surface.

In one implementation, tagged amplification products would be pooled after PCR by combining the contents of the many small reaction volumes. In one implementation, this can be achieved by adding a reagent that causes aqueous droplets in oil to coalesce (e.g. chloroform). In one implementation, reaction volumes can be combined by harvesting reaction products from micro-wells on a microfluidic device. In one implementation, the pooled, amplified DNA products are gel-purified to select products of the desired size and to eliminate unused primers before subjecting to massively parallel sequencing. In certain implementations, other approaches to purification could be used, including but not limited to hybrid capture using biotin-tagged complementary oligonucleotides, high-performance liquid chromatography, capillary electrophoresis, silica membrane partitioning, or binding to magnetic Solid Phase Reversible Immobilization (SPRI) beads.

In one implementation, next-generation sequencing (NGS) is used to obtain large numbers of sequences from the tagged, amplified, and purified PCR products. In one implementation, a clonal overlapping paired-end sequencing approach (as described above) can be used to filter out reads containing sequencer-derived errors. In one implementation, sequence data is analyzed to identify true mutations derived from copying both strands of a targeted double-stranded template DNA fragment. The strategy used to identify such true mutations can be understood by referring to FIGS. 9-11. The following logic is used:

1. In one implementation, MLT patterns can be used to determine whether amplified PCR products within a micro-compartment were derived from copying one template strand or two template strands. In one implementation, if a single MLT sequence-pair is seen in the amplified sequences from a given compartment, then it can be inferred that the amplified sequences were derived from a single strand of DNA that was amplified within that compartment. In one implementation, if two (or more) MLT sequence-pairs are seen in the amplified sequences from a given compartment, then it can be inferred that the amplified sequences were derived from two (or more) strands of DNA that were amplified within that compartment.
2. In one implementation, PCR amplified sequences can be identified as being derived from a given compartment based on analysis of compartment-specific barcodes. In one implementation, there can be a single barcode assigned to a compartment. In another implementation, there can be more than one barcode assigned to a compartment. If there is more than one barcode, the combination of barcodes can be used to identify the PCR products as having been derived from the same compartment.
3. In one implementation, a mutation would be considered to be an authentic template-derived mutation if the (a) the majority of amplified sequences derived from a given compartment contain the mutation, and (b) the observed MLT pattern confirms that the amplified sequences are derived from more than one template strand. Since a compartment would be very unlikely to contain more than one DNA fragment, it can be inferred with high certainty that sequences derived from more than one template strand are derived from complementary strands of a duplex DNA fragment.

Method for Delivering Clonally Tagged Oligonucleotides to Different Compartments:

Using beads to deliver clonally tagged primers to different compartments has several disadvantages. Synthesis of such bead populations can be complex, especially because split-and-pool steps are used. It can also be difficult to ensure random distribution of beads into compartments, because the beads can settle or aggregate, leading to a distribution that does not follow Poisson statistics. To achieve a more random distribution of beads, a bead slurry may need to be continuously stirred, or compartmentalization may be performed quickly to minimize settling of beads.

Pre-dispensing clonally tagged primers to into micro-compartments has a disadvantage of procedural complexity. Primers must be separately synthesized with different tags, and copies of differently tagged primers would have to be dispensed into different micro-wells. This would involve use of a special robotic device. It may be feasible to distribute tagged primers into hundreds or thousands of micro-wells, but it would be difficult to achieve this for larger numbers of compartments (e.g. millions).

Methods and compositions are disclosed that deliver clonally tagged oligonucleotides to micro-compartments without requiring attachment of the oligonucleotides to a surface (such as beads or a micro-well wall). Use of oligonucleotides in solution is advantageous because it ensures more even distribution of tags into compartments and is very simple to implement. The scheme is outlined in FIG. 6.

Figure 6:
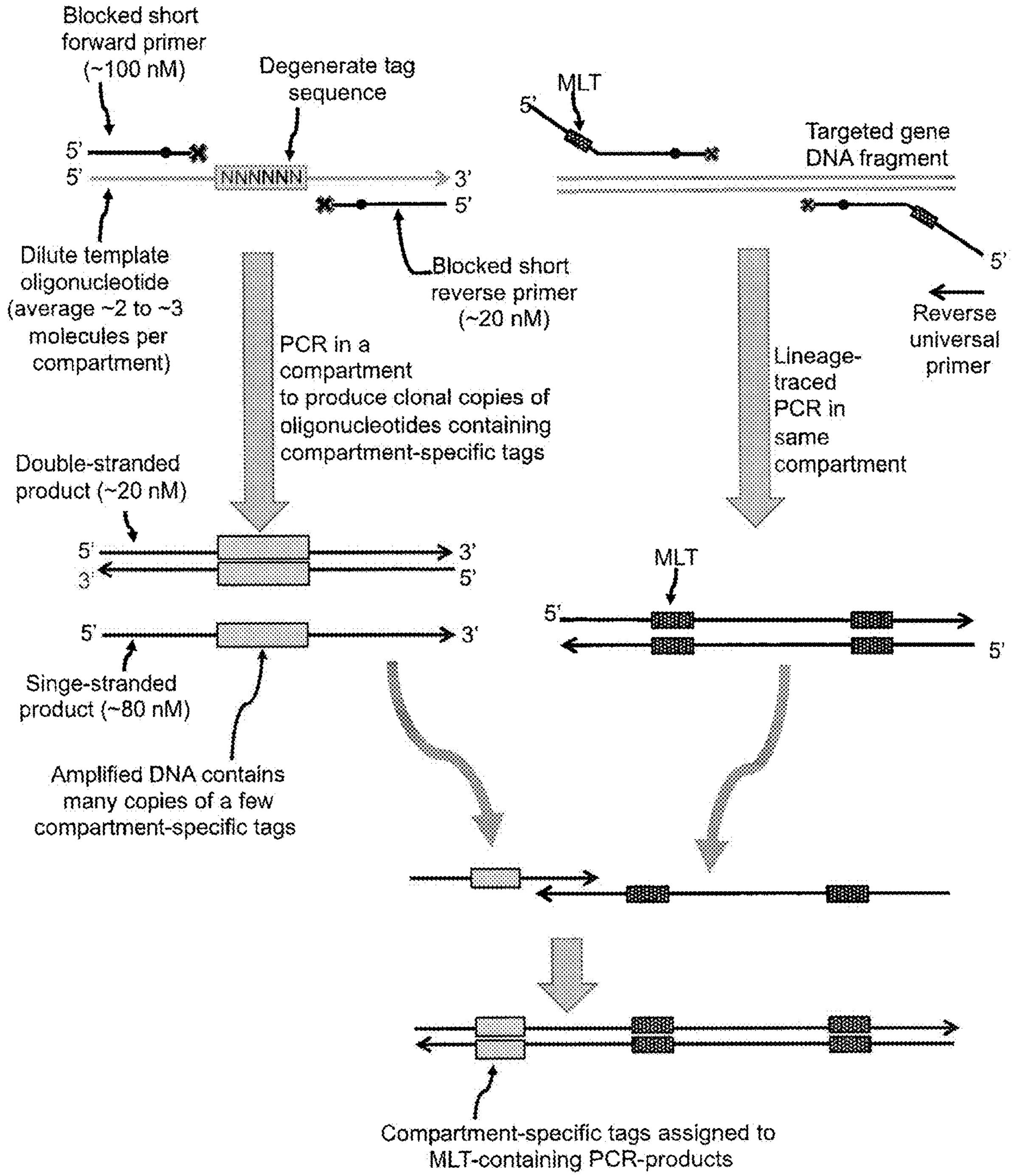
FIG. 6 shows an in-solution method for delivering clonally tagged oligonucleotides into micro-compartments, which can function as primers to add compartment-specific tags to PCR products that are co-amplified with the same reaction volume.

FIG. 6 shows an in-solution method for delivering clonally tagged oligonucleotides into micro-compartments, which can function as primers to add compartment-specific tags to PCR products that are co-amplified with the same reaction volume. A template oligonucleotide containing a degenerate tag sequence can be added to a PCR cocktail such that when the PCR cocktail is compartmentalized, a small number of individual template oligonucleotide molecules (for example, an average of ~2 to ~3 molecules) are partitioned into each compartment. Primers capable of amplifying the template oligonucleotide are also included in the reaction cocktail. Thus, when PCR is carried out, a small number of template oligonucleotides within each compartment are amplified to produce many copies containing a few clonal compartment-specific tags. These clonally tagged oligonucleotides can be used as primers to assign compartment-specific tags to other PCR products that are co-amplified within the same reaction volume (for example, via lineage-traced PCR of multiple genomic regions).

In one implementation, many copies of a uniformly tagged oligonucleotide sequence can be produced in a compartment by introducing a single molecule of that tagged DNA sequence into the compartment and then copying and amplifying it within the compartment using short primers (via PCR). By starting with a single tagged DNA molecule as a template, the amplified copies within the compartment would be clonal, harboring the same tag as the template molecule. In one implementation, the tagged template DNA can be double stranded. In another implementation, the template DNA can be single-stranded, consisting of either the top or bottom complementary strand. In one implementation, tag (or barcode) sequences within a population of template molecules can be generated by incorporating degenerate positions during oligonucleotide synthesis (e.g., by incorporating multiple "N" positions, were N denotes an approximately equal probability of coupling a T, C, G, or A base). In one implementation, pre-defined barcodes can also be incorporated into the template molecules. In one implementation, more than one differently tagged molecule can be used as a template within a compartment, in which case the amplified oligonucleotides within a compartment would contain more than one tag sequence. In certain implementations, to minimize the number of compartments containing no tagged template molecule, an average of two or three differently tagged template molecules can be introduced into a compartment (distributed according to Poisson statistics). In one implementation, the resulting amplified clonally tagged oligonucleotide copies within a compartment can function as primers by hybridizing to and copying other DNA sequences within the compartment. In one implementation, such primers can be used to assign compartment-specific tags to the amplification products within a compartment. If primers containing more than one compartment-specific tag (barcode) are present within a compartment, the combination of tags can be used to identify the amplification products as being derived from a given compartment. In one implementation, an unequal concentration of forward and reverse short primers can be used to amplify a tagged template molecule within a compartment. In one implementation, a forward primer can be two-fold to 20-fold more concentrated than a reverse primer (or vice versa). Use of primers of unequal concentration leads to "asymmetric PCR", producing more copies of one amplified strand than its complement. In one implementation, such asymmetric amplification can promote hybridization of the amplified clonally tagged oligonucleotides with other DNA sequences in the compartment (thus allowing the amplified oligonucleotides to function as tagged primers). FIG. 6 illustrates this approach.

This method to introduce many copies of a clonally tagged oligonucleotide sequence into a reaction compartment has many potential applications. In one implementation, it can be used to aid in measurement of low-abundance mutant DNA molecules as described above. In another implementation, it can be used to tag amplified DNA products from single cells in different compartments to generate single-cell genomic data. In another implementation, the method can be used to label copies of complementary DNA (cDNA) from single cells in different compartments to facilitate high-throughput RNA profiling of single cells. In another implementation, the method can be used to assign the same tag to multiple amplicons derived from a larger chromosomal fragment within a compartment, in order to facilitate genomic sequence assembly.

In another implementation, the compartment-specific DNA tagging method can be used to facilitate highly multiplexed single cell proteomics. In this approach, antibodies targeting different proteins can be labeled with oligonucleotides containing an antibody-specific barcode sequence flanked by common primer binding sequences. A multiplexed panel of antibodies can be bound to proteins on the surface of intact cells or inside fixed and permeabilized cells. Each antibody in the panel is labeled with an oligonucleotide containing a different antibody-specific tag. After washing away excess antibodies, cells can be compartmentalized (for example into aqueous droplets in oil or into micro-wells on a microfluidic device) such that each compartment is unlikely to contain more than one cell. Common PCR primers within the compartments could be used to simultaneously amplify all antibody-bound barcoded oligonucleotides via common primer binding sequences. The relative abundance of an amplified tag within a compartment would reflect the relative abundance of the corresponding antibody bound to its protein target within the cell. Compartment-specific barcodes could then be introduced to enable quantitation of proteins in different single cells. Since a large variety of antibody-specific tags can be created, the multiplexing capacity for different antibodies is virtually limitless.

More generally, the described method can be used for any application in which nucleic acid molecules within a compartment need to be labeled with a compartment-specific tag.

Figure 15:
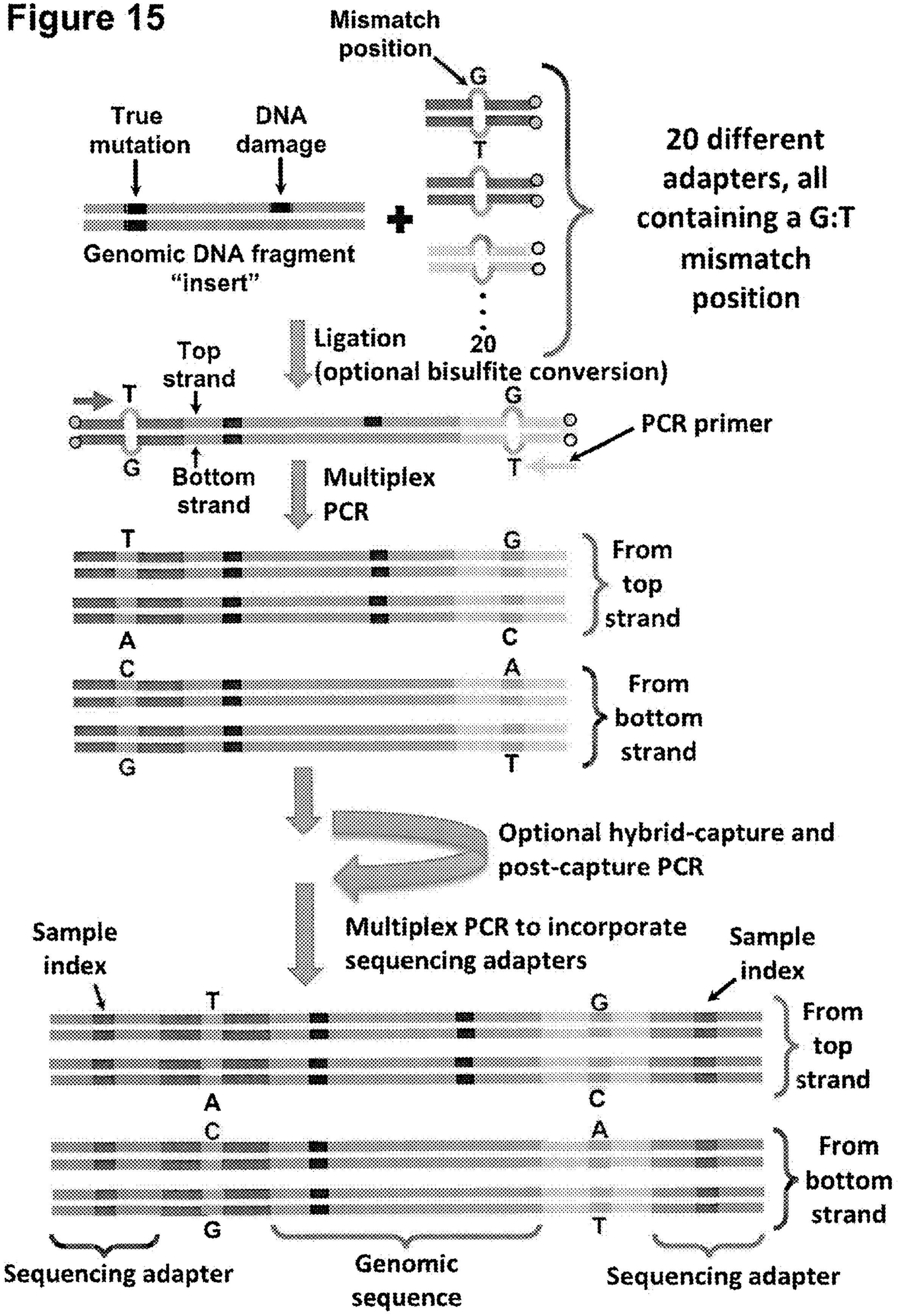
FIG. 15 shows an example schematic of how multiple different (non-Y-shaped) adapter sequences can be ligated to genomic insert DNA fragments to enable PCR-amplification of the inserts prior to next-generation sequencing. The presence of mismatched bases in the paired adapter strands enables sequences arising from the top strand of an insert DNA fragment to be distinguished from those arising from the bottom strand. True mutations should be found on sequences arising from both strands of an insert DNA fragment. In contrast, DNA damage, PCR errors, or sequencer errors would be very unlikely to be found on sequences arising from both strands of an insert DNA fragment.

Methods for Sequencing Library Preparation Via Adapter Ligation and Paired-Strand Analysis:

FIG. 15 provides a schematic of methods and systems to enable analysis of sequence information derived from paired strands of DNA from individual double-stranded DNA fragments. This approach is directed to sensitive and efficient measurement of low-abundance variant sequences within complex nucleic acid mixtures. The method ligates double-stranded DNA fragments obtained from biological samples to partially or fully double-stranded adapter oligonucleotides which enable PCR-amplification, optional hybrid-capture-based enrichment, and next-generation sequencing of the biologically-derived DNA fragments. This method employs multiple different adapter sequences simultaneously in a single ligation reaction, so that there is a high probability of having different adapter sequences ligated to the two ends of a double-stranded DNA fragment (also known as the insert). Because multiple possible combinations of adapter sequences can be ligated to the two ends of a given insert, sequences derived from the same individual insert molecule can be identified based on the beginning and end positions of the insert sequence (relative to the genomic reference) and the specific combination of adapters. In one implementation, the adapters are designed to have at least one non-complementary (mismatched) base pair (such as G:T) so that PCR-amplification products derived from the top strand of the adapter-ligated insert can be distinguished from those derived from the bottom strand of the same adapter-ligated insert. By comparing PCR-amplified sequences arising from both strands of a double-stranded DNA insert fragment, a variant (mutation) can be identified with very high confidence if the sequence is confirmed to be present on both strands of the DNA insert fragment.

The concept of comparing paired strands of DNA from individual double-stranded DNA fragments as described previously in this document can also be applied to improving methods for analysis of epigenetic modifications of DNA molecules, including but not limited to methylation of cytosine and/or hydroxymethylation of cytosine. Current sequencing-based methods of methylation or hydroxymethylation analysis typically perform chemical (e.g., sodium bisulfite) or enzymatic (e.g. TET2, APOBEC3A, T4-beta-Gal, etc) conversion of cytosines to uracils (which subsequently can be replaced by thymines during copying and amplification by PCR), wherein the rate of conversion is dependent on the presence or absence of epigenetic modifications such as methylation or hydroxymethylation. This difference in conversion efficiency is used to distinguish modified and unmodified cytosine bases via subsequent sequencing. For example, with bisulfite conversion, most unmodified cytosines become converted to thymines (after bisulfite treatment and PCR) and are read as “T” bases during sequencing, whereas 5-methyl-cytosine bases or 5-hyroxymethylcytosine bases rarely become converted, and are read as “C” bases during sequencing. Such conversion of many “C” bases in a DNA sequence to “T” bases leads to many analytical challenges. The increased degeneracy of converted DNA sequences (converted from a 4-letter code to a mostly 3-letter code) can introduce challenges in performing sequence alignments and accurate mapping to a reference genome sequence, especially in regions with repetitive sequences. Furthermore, it becomes challenging to determine with high confidence whether a base which is read as a “T” in the converted sequence was originally a “T” or a “C” in the pre-converted DNA. This is usually inferred by comparison to a known reference sequence (such as the human genome), but because “C” to “T” mutations are common in genomic DNA, it becomes difficult to know the true epigenetic status of such bases.

To address these challenges, we show that comparison of converted sequences derived from paired strands of a double-stranded DNA fragment can be used to disambiguate cytosine, thymine, and modified cytosine (e.g. 5-methylcytosine or 5-hydroxymethylcytosine) in the original DNA fragments. We show that this can be achieved in a high-throughput manner, enabling a plurality of DNA fragments to be simultaneously analyzed using next-generation sequencing readouts. Importantly, the methods we describe do not require comparison to a reference sequence (such as the human genome), because disambiguation of bases can be achieved by comparing converted sequences derived from paired strands of the double-stranded DNA fragment. Additionally, the methods we describe herein enable characterization of epigenetic modifications on both strands of a double-stranded DNA fragment. Thus, for a given CpG site, the methods make it possible to determine whether the cytosines are modified on both strands of DNA, only on the (+) strand, only on the (−) strand, or on neither strand. Thus, for example, instead of simply knowing whether a particular CpG site is methylated or unmethylated on one strand, one can know whether it is fully methylated, fully unmethylated, or hemi-methylated on paired strands.

In one implementation, the method enables determination of base sequences and epigenetic modifications of a plurality of DNA fragments. In one implementation, DNA fragments are purified from biological specimens such as (but not limited to) human plasma, whole blood, solid organs, blood cells, tumor tissue, urine, cerebrospinal fluid, saliva, pleural fluid, peritoneal fluid, stool, or vaginal fluid. In one implementation, the DNA fragments are subjected to enzymatic end-repair and/or A-tailing, in order to generate fragments with either blunt ends or ends with an overhanging A on the 3'-end. This prepares the DNA fragments for ligation. In one implementation, end-repair can be performed with 5-methyl-dCTP and/or 5-methoxy-dCTP in the reaction cocktail (as partial or complete replacement for dCTP) to serve as a marker for the portion of the double-stranded DNA that was filled-in by polymerase extension. In one implementation, DNA adapter molecules are ligated to both paired DNA strands of a double-stranded DNA fragment (on one end or both ends of the DNA fragment). In an alternate implementation, adapter molecules can be attached in a similar manner by a transposase enzyme or by primer extension. In a further alternate implementation, an adapter molecule can be ligated to the 5'-end of one strand of DNA, and a polymerase can be used to extend the 3'-end of the opposite strand to make a reverse-complement copy of the ligated adapter molecule, thereby attaching adapter sequences to both strands of the DNA. In one implementation, the adapter molecule comprises a DNA sequence tag that is substantially unique to the adapter (e.g., a Unique Molecular Identifier). In another implementation, the adapter molecule comprises a Molecular Lineage Tag (which may have diverse sequences but not necessarily sufficient diversity to be unique). In another implementation, a plurality of different adapters are used (e.g. similar to the scheme shown in FIG. 15). In one implementation, the adapter can be fully double-stranded, or can be partially double-stranded and partially single-stranded. In one implementation, the adapter can be fully single-stranded. In one implementation, the adapter can comprise the 4 unmodified DNA bases (A, C, T, and G). In another implementation, the adapter can comprise modified DNA bases, including but not limited to 5-methylcytosine and/or 5-hydroxymethylcytosine. In one implementation, partially-double-stranded adapters (e.g., Y-shaped), all having a common sequence, can be ligated to both strands of the double-stranded DNA fragments.

In one implementation, the DNA fragments with ligated adapters can be subjected to conversion of cytosine baes to uracil bases, wherein the conversion efficiency is dependent on the presence or absence of an epigenetic modification on the cytosine base. In one implementation, the conversion is performed using chemical reagents, including but not limited to Sodium Bisulfite, potassium perruthenate, and/or pyridine borane. In one implementation, the conversion is performed using enzymatic methods including, but not limited to APOBEC3A, TET2, and/or T4-betaGal. In one implementation, the conversion is performed using a combination of enzymatic and chemical methods. In one implementation, adapters may contain modified bases which would be resistant to conversion. In one implementation, the number of DNA molecules that are subjected to conversion can be intentionally reduced to increase the probability of subsequently sampling sequences derived from both paired strands of a double-stranded DNA fragment. If too many double-stranded DNA fragments are subjected to conversion, then during subsequent sequencing, there may be a low probability of obtaining a sequence derived from both strands of any given DNA fragment.

In one implementation, the converted DNA fragments can be subjected to copying and amplification by the polymerase chain reaction (PCR). In one implementation, uracil bases which were formed from cytosine bases during the conversion process can be replaced by thymine bases in the PCR-generated copies. In one implementation, the number of converted DNA molecules that are subjected to PCR-amplification can be intentionally reduced to increase the probability of subsequently sampling sequences derived from both paired strands of a double-stranded DNA fragment.

In one implementation, the converted and PCR-amplified DNA copies can be subjected to sequencing. In one implementation, sequencing includes but is not limited to next-generation sequencing or massively parallel sequencing. In one implementation, next-generation sequencing can be performed on an instrument manufactured by companies including but not limited to Illumina, Ion Torrent, Qiagen, Thermo Fisher, Roche, and/or Pacific Biosciences. In one implementation, sequencing can be performed in paired-end mode or in single-end mode. In one implementation, sequencing read lengths can be between 30 and 500 bases. In one implementation, sequencing is performed with 150- or 100-base read-lengths, in paired-end mode. In one implementation, the sequencing output yields a plurality of converted sequences.

Figure 16:
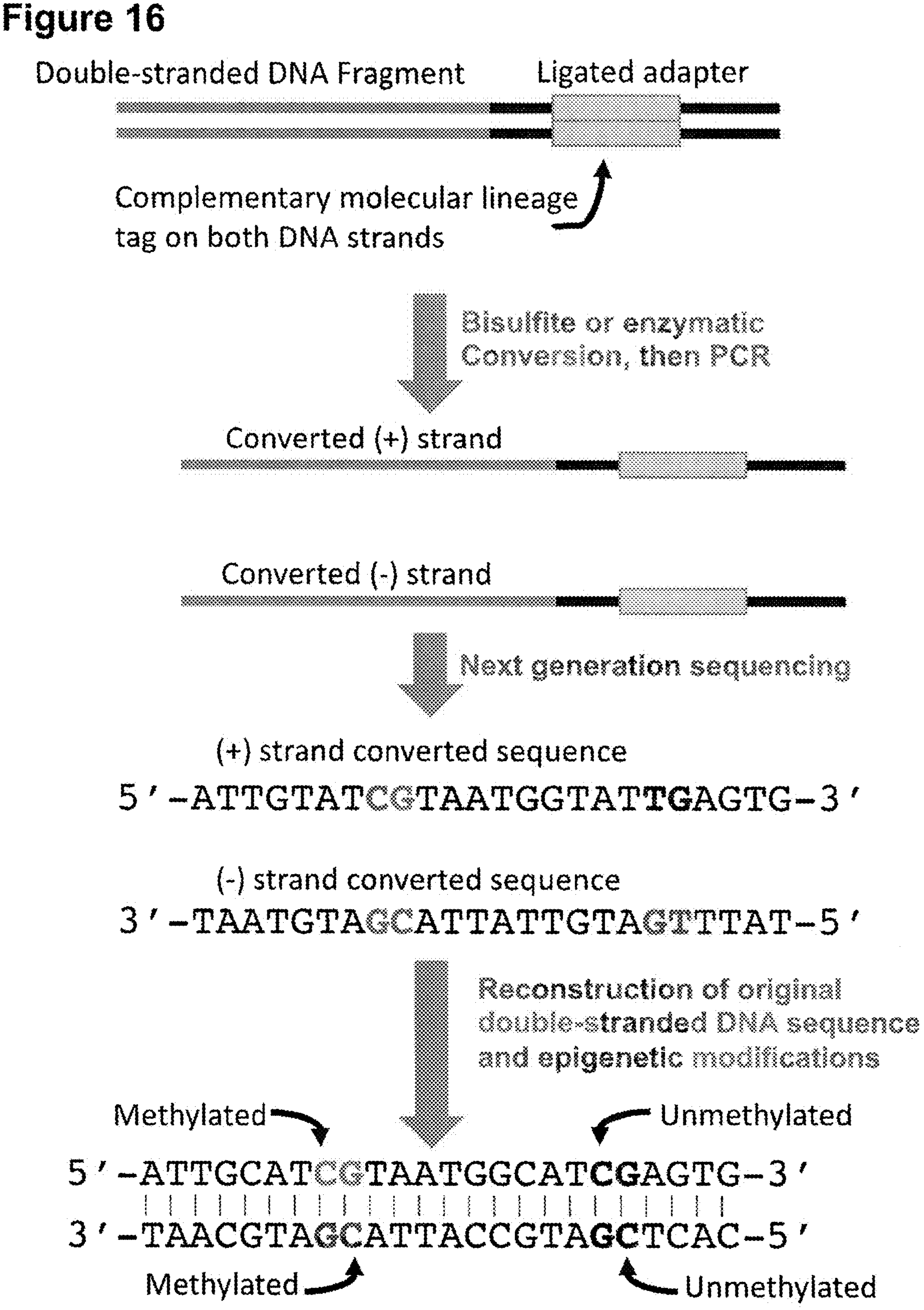
FIG. 16 shows an example schematic of paired-strand analysis of methylation and/or hydroxymethylation. Double-stranded DNA fragments (already ligated to adapters) can undergo bisulfite or enzymatic conversion followed by PCR amplification and next-generation sequencing to produce converted sequences that are derived from both strands of the individual double-stranded DNA fragments. Converted sequences arising from the same double-stranded DNA fragment can be grouped together. Then, as depicted in the example, the original sequence of the double-stranded DNA fragment can be reconstructed, including information about the presence of 5-methylcytosine and/or 5-hydroxymethylcytosine base positions on both strands of the DNA fragment.

In one implementation, the plurality of converted sequences can be grouped into sets, wherein each set of sequences is determined to be derived from an individual double-stranded DNA fragment. In one implementation, each set contains at least one sequence derived from each of the two paired strands. In one implementation, grouping can be performed based on the identity of tags in the ligated adapters. If each adapter has a unique tag, and a common tag is present on both paired-strands of the double-stranded DNA, then sequences having the same tag can be grouped together. In one implementation, the partial or complete sequence of DNA fragment (excluding the adapter sequence) can be used as a unique molecular identifier. Although different fragments may have partially overlapping sequences, if genomic coverage is low, there will be a low probability that two different DNA fragments will be perfectly overlapping (i.e, same length and same end positions in the genome). Thus, in some implementations, the fragment sequence can be used for grouping. Although a given double-stranded DNA fragment would produce two different converted sequences (due to conversion of cytosines at different positions on the (+) strand and the (−) strand), the sequence can still be used to generate groups. Because after conversion and amplification, purines still remain as purines, and pyrimidines still remain as pyrimidines, one approach to identify sequences arising from the same original double-stranded DNA fragment is to further convert sequences to purine (R) and pyrimidine (Y) notation. For example, the hypothetical (+) and (−) strand converted sequences shown in FIG. 16 and listed below have the same sequence when using R and Y notation.

```
(+) strand converted sequence:
                                          (SEQ ID No: 1)
5'-ATTGTATCGTAATGGTATTGAGTG-3'

With R/Y notation:
                                          (SEQ ID No: 2)
5'-RYYRYRYYRYRRYRRYRYYRRRYR-3'

Reverse complement of (-) strand converted
sequence:
                                          (SEQ ID No: 3)
5'-ATTACATCGTAATAACATCAAATA-3'

With R/Y notation:
                                          (SEQ ID NO: 4)
5'-RYYRYRYYRYRRYRRYRYYRRRYR-3'
```

In one implementation, sequences having the same R and Y sequence can be grouped together in a set. In one implementation, grouping of converted sequences can be performed using combined sequence information from the adapter and from the DNA fragment (also known as an "insert").

In one implementation, sequences derived from opposite strands of DNA within each grouped set of sequences can be compared to each other to determine the sequence and the epigenetic modifications of the original double-stranded DNA fragments. Because conversion of cytosines to thymines produces a different sequence from the (+) strand versus from the (−) strand, it is straightforward to identify converted sequences that arise from opposite paired strands. In one implementation, the base sequence and epigenetic modified bases in an original double-stranded DNA fragment can be decoded or reconstructed from the converted sequences from both paired DNA strands using a scheme as shown in Table 8. The decoding scheme shown in Table 8 is provided as an example, and it valid for bisulfite conversion, and some enzymatic conversion methods. In some implementations, for other conversion methods, modified decoding schemes can be used.

EXAMPLES

The present technology may be better understood by reference to the following examples. These examples are intended to be representative of specific implementations.

Example 1

This example describes methods and systems that are directed to sensitive and efficient measurement of low-abundance variant sequences within complex nucleic acid mixtures. We refer to the method described in this example as "lineage-traced PCR" (LT-PCR). The goal of LT-PCR is to assign molecule-specific tags (called molecular lineage tags or MLTs) to template DNA molecules during the first few cycles of PCR to make it possible to distinguish true template-derived mutations from sequencer or PCR errors. This example describes analysis of DNA from blood samples obtained from patients with cancer, but the method can also be more generally applied to samples from other sources such as tumor tissue, cells, urine, etc. The method can be applied to single-stranded or double-stranded DNA templates and also to complementary DNA (cDNA) generated by reverse-transcription of RNA.

Collection and Processing of Patient Plasma Samples:

Blood was collected by venipuncture into a vacuum tube containing potassium-EDTA. Various tube sizes were used, typically between 3 mL and 10 mL. Blood was inverted in the tube several times at the time of collection to ensure even mixing of the $K_2$-EDTA. Samples were stored temporarily and transported at room temperature (20-25° C.) prior to separation of plasma. Plasma was separated and frozen as soon as possible after blood collection, preferably within three or four hours. The collection tubes were centrifuged at 1000×g for 10 minutes in a clinical centrifuge with a swinging bucket rotor with slow acceleration and deceleration (brake off). Plasma was removed from the red blood cells and buffy coat using a 1 mL pipette, being careful not to disturb the cells at the bottom of the tube (to avoid aspirating white blood cells which would lead to increased background wild-type DNA levels). The plasma was dispensed into 1.5 mL cryovials in 0.5 to 1 mL aliquots. The plasma was then frozen at −80° C. until needed for further processing.

Extraction and Purification of DNA from Plasma:

Plasma was removed from the −80° C. freezer and was thawed at room temperature for 15 to 30 minutes before proceeding with DNA extraction. Thawed plasma was then centrifuged at 6800×g for 3 minutes to remove any cryo-precipitate. The supernatant was transferred to a fresh tube for further processing.

The QiaAmp® MinElute® Virus Vacuum Kit (Qiagen) was used for extraction of DNA from plasma volumes up to 1 mL (elution volume as low as 20 μL). For larger volumes of plasma up to 5 mL, the QiaAmp® Circulating Nucleic Acid Kit was used for DNA purification (elution volume as low as 20 μL). All kits were used according to the manufacturer's instructions, generally eluting the DNA into the lowest recommended volume (preferably 20 μL). To process 1 mL of plasma using the QiaAmp® MinElute® Virus Vacuum Kit, 5 micrograms of carrier RNA (cRNA; Qiagen) were added per mL, and the user-developed protocol found on the Qiagen website was followed.

Synthesis of Universal Primers and MLT-Containing Gene-Specific Primers Having Blocked 3'-Ends:

Oligonucleotide primers were designed to target specific mutation-prone regions of genomic DNA for amplification via PCR. Primers were synthesized on an automated DNA oligonucleotide synthesizer (Dr. Oligo 192) using standard phosphoramidite chemistry in the 3' to 5' direction at 200 nanomole scale on Universal Polystyrene Support III (Glen Research). The design of the primers is schematized in FIGS. 1 and 2. Gene-specific primers have gene-specific sequences at their 3'-ends, they contain seven degenerate positions comprising the MLT, and they contain a portion of the universal primer sequence. Universal primers contained LNA modifications in order to raise their melting temperature. Primer sequences are listed in Table 1, below. Primers were either gel purified or cartridge purified. To verify that the method is able to simultaneously analyze multiple targets, primers were designed to target eight genomic regions that are often mutated in cancer: 1 region of KRAS, 1 region of BRAF, 1 region of PPP2R1A, two regions of PIK3CA, and three regions of EGFR. Although in this example, eight genomic regions were targeted in this example, the method can readily be expanded to include tens or hundreds or possibly thousands of target amplicons.

TABLE 1

| Targeted gene | Primer Sequence |
|---|---|
| Gene-specific Forward Primers: | |
| KRAS | CTACACGACGCTCTTCCGATCTNNNNNNNAGGCCTGCTGAAAATGACTGAATATAaACTTXX (SEQ ID No: 5) |
| BRAF | CTACACGACGCTCTTCCGATCTNNNNNNNCCTCACAGTAAAAATAGGTGATTTTGgTCTAXX (SEQ ID No: 6) |
| PPP2R1A | CTACACGACGCTCTTCCGATCTNNNNNNNGACTCCCAGGTACTTCCGGaACCTXX (SEQ ID No: 7) |
| PIK3CA region 1 | CTACACGACGCTCTTCCGATCTNNNNNNNCAGCTCAAAGCAATTTCTACACGaGATCXX (SEQ ID No: 8) |
| PIK3CA region 2 | CTACACGACGCTCTTCCGATCTNNNNNNNGCAAGAGGCTTTGGAGTATTTCATgAAACXX (SEQ ID No: 9) |
| EGFR region 1 | CTACACGACGCTCTTCCGATCTNNNNNNNGGATCCCAGAAGGTGAGAAAGTTAAaATTCXX (SEQ ID No: 10) |
| EGFR region 2 | CTACACGACGCTCTTCCGATCTNNNNNNNAAAACACCGCAGCATGTCAAgATCAXX (SEQ ID No: 11) |
| EGFR region 3 | CTACACGACGCTCTTCCGATCTNNNNNNNCATCTGCCTCACCTCCAcCGTGXX (SEQ ID No: 12) |
| Genie specific Reverse Primers: | |
| KRAS | CAGACGTGTGCTCTTCCGATCTNNNNNNNCTGAATTAGCTGTATCGTCAAGgCACTXX (SEQ ID No: 13) |
| BRAF | CAGACGTGTGCTCTTCCGATCTNNNNNNNACTGTTCAAACTGATGGGACcCACTXX (SEQ ID No: 14) |
| PPP2R1A | CAGACGTGTGCTCTTCCGATCTNNNNNNNCTTGGCAAACTCCCCCAgCTTGXX (SEQ ID No: 15) |
| PIK3CA region 1 | CAGACGTGTGCTCTTCCGATCTNNNNNNNATCTCCATTTTAGCACTTACCTgTGACXX (SEQ ID No: 16) |
| PIK3CA region 2 | CAGACGTGTGCTCTTCCGATCTNNNNNNNTCAATGCATGCTGTTTAATTGTgTGGAXX (SEQ ID No: 17) |
| EGFR region 1 | CAGACGTGTGCTCTTCCGATCTNNNNNNNAGCAGAAACTCACATCGAGGaTTTCXX (SEQ ID No: 18) |
| EGFR region 2 | CAGACGTGTGCTCTTCCGATCTNNNNNNNTGCCTCCTTCTGCATGGTATTeTTTCXX (SEQ ID No: 19) |
| EGFR region 3 | CAGACGTGTGCTCTTCCGATCTNNNNNNNAGCCAATATTGTCTTTGTGTTcCCGGXX (SEQ ID No: 20) |

TABLE 1-continued

| Targeted gene | Primer Sequence |
|---|---|
| Universal Primers: | |
| Short universal forward | ACAC+TCT+TTCCC+TACACGACGCTCTTCCgATCTXX (SEQ ID No: 21) |
| Short universal reverse | G+TGAC+TGGAGT+TCAGACGTGTGCTCTTCCgATCTXX (SEQ ID No: 22) |
| Long universal forward with barcode & sequencing adapter | AATGATACGGCGACCACCGAGATCTACAC[**FWDBC**]ACAC+TCT+TTCCC+TACACGACG-CTCTTCCgATCTXX (SEQ ID No: 23) |
| Long universal reverse with barcode & sequencing adapter | CAAGCAGAAGACGGCATACGAGAT[**REVBC**]G+TGAC+TGGAGT+TCAGACGTGTGCTC-TTCCgATCTXX (SEQ ID No: 24) |

Notes
X = dA in opposite orientation using dA-5'-CE phosphoramidite (Glen Research).
Residues in lower case are RNA; Residues in upper case are DNA.
FWDBC = forward barcode; REVBC = reverse barcode.
Forward and reverse barcodes were each 8 nucleotides long and differed from all other barcodes at a minimum of 2 positions.
N = degenerate position with equal probability of incorporating A, T, C, or G.
A "+" in front of a residue indicates an LNA nucleotide at that position.
All primers were synthesized on Universal Polystyrene Support III (Glen Research).

Lineage-Traced PCR Tagging and Amplification:

A modified polymerase chain reaction (PCR) was performed in a single reaction tube for each DNA template sample using the conditions outlined below:

Lineage-Traced PCR Setup (20 μL Reaction):

- Purified template DNA (may contain co-eluted carrier RNA [cRNA]) 10 μL (or less)
- 5× concentrated Phusion HF Buffer (Thermo) 4 μL
- Mix of 16 gene-specific primers (stock has 200 nM each) 2 μL
- Mix of Universal Forward and Reverse primers with sample-specific barcode and sequencing adapter (stock has 5 μM each) 2 μL
- Mix of 4 dNTPs (stock 10 mM each) 0.4 μL
- Phusion Hot Start II DNA Polymerase (Thermo) (2 U/μL stock) 0.2 μL
- RNAse H2 (Integrated DNA Technologies) (20 mU/μL stock) 1 μL
- Water (to make final volume of 20 uL)

For some reactions, the shorter universal primers (without a barcode and sequencing adapter [Table 1]) were added at a final concentration of 200 nM each, in addition to the longer universal primers. Inclusion of shorter universal primers with faster hybridization kinetics was intended to promote more efficient initial amplification of MLT-labeled copies.

Temperature Cycling Conditions:

a. 98° C. for 30 sec
b. 98° C. for 10 sec
c. 70° C. slowly decreased to 60° C. at rate of 1° C. per 10 sec
d. 60° C. for 1 min
e. 72° C. for 30 sec
f. repeat steps b-e for 2 more cycles (total 3 cycles)
g 98° C. for 10 sec
h. 72° C. for 60 sec
i. repeat steps g-h for 34 more cycles (total 35 cycles)
g. hold at 4° C.

Upon completion of thermal cycling, 2 μL of 100 mM EDTA-containing buffer was added to each reaction volume to inactivate polymerase activity. Approximately 10 μL of the amplification products from each sample were then pooled into a single tube for subsequent purification of the amplified DNA.

Preparation of DNA for Next-Generation Sequencing:

The pooled PCR reaction products were purified on a 2% agarose gel with ethidium bromide and 1×TBE buffer. Since all PCR products were of a similar final length, the pooled products appeared on the gel as a somewhat diffuse band. This diffuse band was excised from the gel using a fresh scalpel blade, ensuring that the gel was cut a few millimeters above and below the visible band to include any low-intensity bands that may have run faster or slower and were not well-visualized. Using a QIAquick® Gel Extraction kit (Qiagen) according to the manufacturer's instructions, the DNA was isolated from the gel slice. The DNA was eluted into 50 μL of elution buffer, EB.

Next-Generation Sequencing

To prepare the sample for loading onto an Illumina HiSeq flow cell, the concentration of the DNA was measured using an Agilent Bioanalyzer®, and the DNA was diluted to the concentration recommended by Illumina. Cluster formation was carried out on the flow cell according to Illumina's protocol. The sample was loaded onto a single lane of a flow cell. The sequencing was performed on a HiSeq® 2000 instrument in multiplexed paired-end mode, with a read length of 75 base pairs in each direction. In additional experiments, sequencing has also been performed on an Illumina MiSeq instrument, and paired-end read lengths of 100, 150, 200, or 250 base pairs in each direction have also been utilized. Two index reads were also performed, and the length of the index read was increased from the standard seven cycles up to nine cycles so that our longer barcode (index) sequences could be appropriately read.

Example 2

Similar to Example 1, Example 2 describes methods and systems that are directed to sensitive and efficient measurement of low-abundance variant sequences within complex nucleic acid mixtures. This example incorporates "lineage-traced PCR" (LT-PCR) as described in Example 1, but uses a compartmentalization strategy to further improve upon analytical sensitivity. The PCR was divided into many small reaction volumes such that there was a very low probability of having more than 1 copy of a particular targeted DNA fragment in a given reaction volume. A tagging strategy was used which made it possible to confirm that amplified copies of a variant sequence arose from both stands of a double-stranded template DNA fragment within a given reaction compartment. This example describes analysis of DNA from blood samples obtained from patients with cancer, but the method can also be more generally applied to samples from other sources such as tumor tissue, cells, urine, etc. The method can also be applied to single-stranded DNA templates and also to complementary DNA (cDNA) generated by reverse-transcription of RNA, but with a compromise in the robustness of error suppression.

Collection and Processing of Patient Plasma Samples:

Blood was collected using the same methods as described in Example 1.

Extraction and Purification of DNA from Plasma:

DNA was extracted from patient plasma samples using the same methods as described in Example 1.

Synthesis of Universal Primers and MLT-Containing Gene-Specific Primers Having Blocked 3'-Ends:

The same primers synthesized in Example 1 (Table 1) were used in this example, with the exception of the long forward universal primer (which contains a barcode and sequencing adapter). Primer synthesis was carried out using the same methods as described in Example 1.

Split-and-Pool Synthesis of Oligonucleotides Containing Bead-Specific Barcodes on Magnetic Beads:

Magnetic micro-beads were used to deliver barcoded forward universal primers to different PCR micro-compartments (such as droplets or micro-wells). Each bead was designed to have many primer copies all having the same bead-specific barcode (BSBC). The sequence of the desired forward universal primer sequence is as follows:

(SEQ ID NO: 25)
5'-Biotin-
AATGATACGGCGACCACCGAGATCTACAC[BSBC]ACACTCTTTCCCTAC
ACGACGCTCTTCC-3'

To create millions of magnetic micro-beads having ~1 million bead-specific barcodes, oligonucleotide synthesis was performed directly on the surface of the beads using a split-and-pool approach to generate the barcode sequence. Surface-activated super-paramagnetic 2.8 μm beads having amine modifications (Dynabeads M-270 Amine [Thermo Scientific]) were used as solid supports for oligonucleotide synthesis. For each batch of synthesis, 50 μL of bead slurry was used as provided by the manufacturer (~100 million beads). Because the beads were too small to be retained in the synthesis column by a frit, a donut-shaped neodymium magnet was placed around the column to hold the magnetic beads in place on the sides of the column. A spacer 9 phosphoramidite (Glen Research) directly reacted with the amine-modified beads to create a phosphoramidate bond, which would not be cleaved during standard deprotection in ammonium hydroxide/methylamine (AMA). Additional phosphoramidites were linked to this spacer to grow the desired oligonucleotide chain. The synthesized oligonucleotides remained attached to the beads upon completion of synthesis. The following sequence was synthesized on the surface of the beads:

(SEQ ID NO: 26)
5'-Spacer9-TTTTTTTTTT-spacer C3-
GGAAGAGCGTCGTGTAGGGAAAGAGTGT[BSBC]GTGTAGATCTCGGTGG
TCGCCGTATCATT-3'

To synthesize the oligonucleotide in the 5' to 3' direction, 5'-CE phosphoramidites were used (Glen Research). The oligonucleotide sequence contained 10 dT residues to introduce additional space from the surface of the bead. The bead-specific barcode (BSBC) consisted of 10 residues that were synthesized using split-and-pool synthesis. For phosphoramidite coupling at each of these 10 positions, the synthesis was paused and the magnetic beads were pooled and then split into four columns. The four different columns received the 4 different phosphoramidites (5'-dA, 5'-dT, 5'-dC, and 5'-dG). Synthesis was paused between each of the 10 coupling cycles, to allow the beads to be pooled and equally redistributed to four columns. After synthesis was complete, the bead-bound oligonucleotides were deprotected in AMA at 65° C. for 10 minutes. The beads were then washed with deionized water and then re-suspended in 10 mM Tris pH 7.6 buffer.

To synthesize heat-releasable complementary barcoded primers on the surface of the micro-beads, the following primer was annealed to the bead-bound oligonucleotide, and was extended using Klenow Fragment (Exo-) (New England Biolabs).

(SEQ ID NO: 27)
5'-Biotin-AATGATACGGCGACCACCGAGATC-3'

The beads were re-suspended in 50 μL of NEB buffer 2 (1× concentration) supplemented with 0.2 mM dNTPs. The primer extension reaction was carried out according to the manufacturer's directions, incubating the reaction at 37° C. for 30 minutes after adding Klenow polymerase. Beads were then washed and resuspended in buffer containing 50 mM NaCl and 10 mM Tris pH 7.6.

Bead-Free Method for Delivering Clonally Tagged Primers to Compartments:

In some experiments, instead of using beads, an alternative approach was used to introduce compartment specific tags to the PCR products within the compartments. Like with bead-based delivery, the goal was to deliver the following primer sequence to different compartments:

(SEQ ID NO: 28)
5'-Biotin-
AATGATACGGCGACCACCGAGATCTACAC[CSBC]ACACTCTTTCCCTAC
ACGACGCTCTTCC-3'

In a given compartment, multiple copies of this primer were introduced, with the clonal copies containing one or a few compartment-specific barcodes (CSBCs). To produce such primers, very dilute template DNA was added to the PCR cocktail prior to compartmentalization at a concentration that would allow an average of ~2 to ~3 amplifiable copies (molecules) to be distributed into each compartment (according to a Poisson distribution). The template DNA consisted of the following sequence:

```
DegenTemplate:
                                     (SEQ ID NO: 29)
5'-AATGATACGGCGACCACCGAGATCTACACNNNNNNNNNNNACACTCTT

TCCCTACACGACGCTCTTCC-3'
```

The following primers were also added to the cocktail:

```
Bio-ShortFWD:
                                     (SEQ ID No: 30)
5'-Biotin-AA+TG+AT+ACGGCGACCACCGAGaTCTAXX-3'
(Added in 100 nM final concentration)

ShortREV:
                                     (SEQ ID No: 31)
5'-GGA+AGAGCG+TCG+TGTAGGGAAaGAGTXX-3'
(Added in 20 nM final concentration)
```

X=dA in opposite orientation using dA-5'-CE phosphoramidite (Glen Research).

Residues in lower case are RNA; Residues in upper case are DNA.

N=degenerate position with equal probability of incorporating A, T, C, or G.

A "+" in front of a residue indicates an LNA nucleotide at that position.

As the micro-compartments were subjected to thermal cycling, the few tagged template molecules were clonally amplified, creating many copies of the desired primers containing compartment-specific tags. Because the biotinylated short forward primer was added in 5'-fold excess compared to the short reverse primer, more copies of the forward strand were made than of the reverse strand (via asymmetric PCR). Thus, the excess copies of the forward strand were then able to be further extended by hybridizing to co-amplified gene-specific PCR products in the same compartment. In this way, the gene-specific PCR products in a compartment were labeled with compartment-specific tags. This approach is schematized in FIG. 6.

PCR Cocktail

The PCR cocktail used in this example depended on whether micro-beads were used to deliver compartment-specific primers or whether a bead-free approach was used.

For the bead-based approach, the following PCR cocktail was used:

- Purified template DNA (may contain co-eluted carrier RNA [cRNA]) 10 μL (or less)
- 5× concentrated Phusion HF Buffer (Thermo) 4 μL
- Mix of 16 gene-specific primers (stock has 200 nM each) 2 μL
- Short Universal Forward and Reverse primers (Stock 10 μM each) 1 μL
- Long Universal Reverse primer with sample-specific barcode and sequencing adapter (10 μM stock) 1 μL
- Mix of 4 dNTPs (stock 10 mM each) 0.4 μL
- Phusion Hot Start II DNA Polymerase (Thermo)(2 U/μL stock) 0.2 μL
- RNAse H2 (Integrated DNA Technologies)(20 mU/μL stock) 1 μL
- Water (to make final volume of 20 uL)

(Primer Sequences are Listed in Table 1)

Beads carrying tagged primers were added to the cocktail just prior to compartmentalization, and were mixed well to promote even distribution of the beads into the compartments. The number of beads was adjusted so that an average of ~2 to ~3 beads would be distributed into a micro-compartment.

When the bead-free approach was used to introduce clonal primers containing compartment-specific tags, the following PCR cocktail was used:

- Purified template DNA (may contain co-eluted carrier RNA [cRNA]) 8 μL (or less)
- 5× concentrated Phusion HF Buffer (Thermo) 4 μL
- Mix of 16 gene-specific primers (stock has 200 nM each) 2 μL
- Mix of Short Universal Forward (Stock 5 μM) and Short Universal Reverse primers (Stock 10 μM) 1 μL
- Long Universal Reverse primer with sample-specific barcode and sequencing adapter (10 μM stock) 1 μL
- DegenTemplate (stock concentration adjusted as described below) 1 μL
- Mix of Bio-ShortFWD (1 μM stock) and Short REV (0.2 μM stock) 1 μL
- Mix of 4 dNTPs (stock 10 mM each) 0.4 μL
- Phusion Hot Start II DNA Polymerase (Thermo) (2 U/μL stock) 0.2 μL
- RNAse H2 (Integrated DNA Technologies) (20 mU/μL stock) 1 μL
- Water (to make final volume of 20 μL)

The concentration of the stock solution of the "DegenTemplate" primer was adjusted so that an average of ~2 to ~3 amplifiable molecules would be distributed into each compartment. Digital PCR experiments were conducted using serial dilutions of this template to accurately determine the concentration of amplifiable molecules.

Microfluidic Compartmentalization of PCR:

Two different approaches have been used to compartmentalize the PCR cocktail into microscopic reaction volumes prior to thermal cycling. One approach was to produce microfluidic droplets of aqueous PCR cocktail (optionally containing micro-beads) in oil. A second approach was to divide the PCR cocktail (optionally containing micro-beads) into micro-wells on a microfluidic device. In both approaches, approximately 20,000 separate microscopic reaction volumes of approximately 1 nanoliter each were created from a 20 microliter PCR cocktail. The total number and size of compartments could be adjusted in future experiments depending on the number of genome equivalents being analyzed. The compartmentalization scheme used in this example was based on an estimate of approximately 8-10 ng of genomic template DNA (~3000 genome equivalents).

To compartmentalize the PCR cocktail into aqueous droplets in oil, a BioRad QX100 droplet generator was used with some modifications to the manufacturer's instructions. One modification was that the above PCR cocktail (with or without microbeads) was used instead of the manufacturer's recommended PCR super mix. Droplet Generation Oil for EvaGreen was used. Thermal cycling was carried out in 0.2 mL thin-walled PCR tubes.

To compartmentalize the PCR cocktail into micro-wells, we used a custom microfabricated clear slide onto which polydimethylsiloxane (PDMS) had been patterned to create 20,000 microwells, each holding ~1 nL volume. The PDMS surface had been treated to make it hydrophilic to encourage even distribution of the PCR cocktail into the micro-wells. A coverslip was added to sandwich the PDMS pattern, thus sealing the micro-wells for thermal cycling.

Thermal Cycling:

A thermal cycling protocol was used that was similar to the protocol used in Example 1, except that the final two cycles had a lower annealing temperature to promote hybridization and extension of biotin-labeled primers containing compartment-specific tags.

Temperature Cycling Conditions:

a. 98° C. for 30 sec
b. 98° C. for 10 sec
c. 70° C. slowly decreased to 60° C. at rate of 1° C. per 10 sec
d. 60° C. for 1 min
e. 72° C. for 30 sec
f. repeat steps b-e for 2 more cycles (total 3 cycles)
g 98° C. for 10 sec
h. 72° C. for 60 sec
i. repeat steps g-h for 34 more cycles (total 35 cycles)
j. 98° C. for 10 sec
k. 60° C. for 60 sec
l. repeat steps i-k for 1 more cycle (total 2 cycles)
m. hold at 4° C.

Combining Tagged Products from all Compartments:

Upon completion of thermal cycling, compartmentalized reaction volumes were combined and EDTA-containing buffer was added to the combined volume (~10 mM final concentration) to inactivate polymerase activity. To coalesce droplets in oil, chloroform was added and the emulsion was agitated on a vortexer and then centrifuged at high speed according to Bio-Rad's recommended protocol. To combine the PCR products from micro-wells, the cover slip was removed and the micro-wells were washed with ~200 μL of EDTA-containing buffer. If magnetic beads had been added to the cocktail, these were removed from the solution using a magnet.

Preparation of DNA for Next-Generation Sequencing:

Pooled PCR reaction products were purified on a 2% agarose gel with ethidium bromide and 1×TBE buffer. A band of the expected size (based on size makers run in an adjacent lane) was excised from the gel using a fresh scalpel blade. Using a QIAquick® Gel Extraction kit (Qiagen) according to the manufacturer's instructions, the DNA was isolated from the gel slice. The DNA was eluted into 50 μL of elution buffer, EB (Qiagen).

In some experiments, high-capacity streptavidin-agarose resin slurry (5 μL) (Thermo Scientific) was added to each reaction volume to capture biotin-labeled reaction products. The beads were then washed in 10 mM Tris pH 7.6, and then the DNA strands complementary to the biotinylated strands were eluted from the bead surface by heat-denaturation in 50 μL of elution buffer EB (Qiagen).

Next-Generation Sequencing:

To prepare the sample for loading onto an Illumina HiSeq flow cell, the concentration of the DNA was measured using an Agilent Bioanalyzer®, and the DNA was diluted to the concentration recommended by Illumina. Sequencing was performed as described in Example 1.

Outline of Algorithm for Sequence Analysis:

Computational analysis was performed on the resulting sequence data to identify and quantify mutant double-stranded DNA fragments that produced matching mutant sequences from both strands. The underlying logic used for this analysis is described in the "Methods" section.

Example 3

This example further describes methods and systems that are directed to sensitive and efficient measurement of low-abundance variant sequences within complex nucleic acid mixtures. Specifically, this example describes the production and utilization of microfluidic silicon chips containing thousands of micro-wells in which separate polymerase chain reactions (PCRs) can be performed. These microfluidic chips provide a simple and effective method for compartmentalizing PCR amplification reactions into thousands of micro-volumes to enable amplification of single template nucleic acid molecules or a few (<20) template nucleic acid molecules in each compartment. The example can be applied to analysis of samples containing double-stranded DNA templates, single-stranded DNA templates and to complementary DNA (cDNA) generated by reverse-transcription of RNA.

Fabrication of Silicon Chips Containing PCR-Compatible Microwells:

P-type 4-inch prime grade silicon wafers with orientation <100> were acquired from University Wafers Inc. Each wafer had a thickness of 500+/−25 micrometers with single side polished. The silicon wafer was dipped in JT Baker® 5175-03 CMOS electronic grade buffered oxide etch (BOE) 10:1 solution for 1 minute. The wafer was removed from the BOE solution, and held under a running stream of de-ionized water for at least a minute to remove any traces of BOE. The wafer was blow-dried with nitrogen gas, and then was baked at 150° C. for at least 2 minutes to remove water molecules from the surface.

For spin-coating of photoresist onto the silicon wafer, it was allowed to cool down to room temperature, and then it was centered on the chuck of a Laurell WS-400 6NPP spin-coater and held firmly by vacuum. 7.5 ml of positive photoresist (Microchemicals GmbH AZ® 9260) was dispensed gently at the center of the wafer using a glass beaker. Precaution was taken to avoid forming or trapping bubbles while dispensing the photoresist. The wafer was spin-coated at 3000 rotations per minute (RPM) for a minute with an acceleration of 2014 RPM/s. The wafer was removed from the spin coater and baked at 110° C. for 90 seconds. The wafer was then allowed to cool down to room temperature for 15 minutes.

Figure 12:
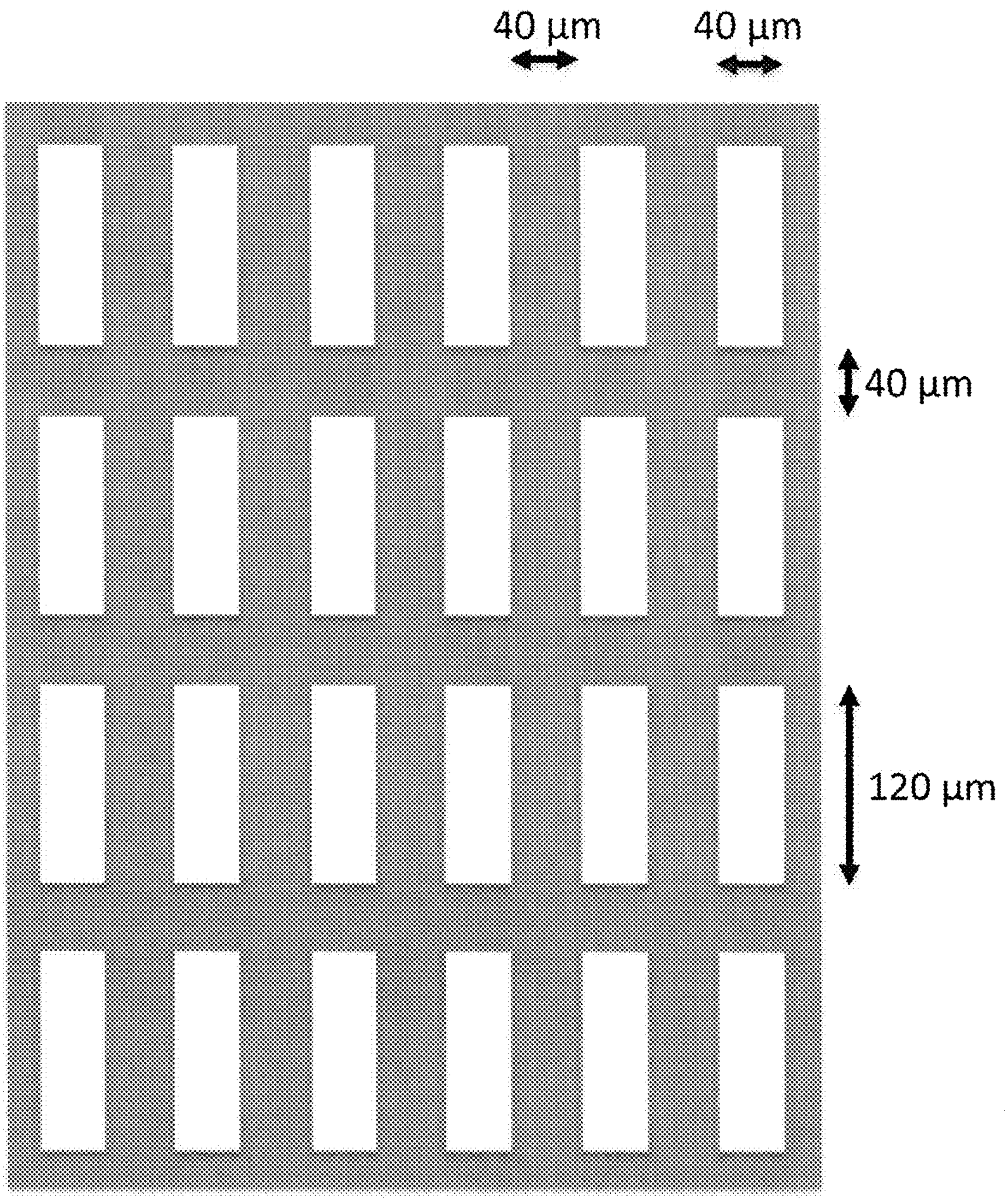
FIG. 12 shows an example of a pattern on a photomask used for photolithography to produce microscopic wells etched into the surface of a silicon wafer. Shaded areas represent opaque portions of the mask, and clear areas represent transparent portions of the mask.

For photolithography, photomasks were drawn using commercial AutoCAD or L-Edit drafting software. Because a positive photoresist was used, areas exposed to UV light would become more soluble in the developer, whereas areas shaded by the mask would remain crosslinked/polymerized. The mask was designed to create rectangular microwells having a width of ~40 micrometers, and a length of ~120 micrometers, with wells separated from each other by walls of ~40 micrometer thickness. Thus, the mask contained an opaque background with a pattern of transparent rectangles, each measuring 40×120 micrometers, with a spacing of 40 micrometers between the transparent rectangles. An illustration of the pattern used on the mask is provided in FIG. 12. Chrome-patterned glass photomasks were printed using a Heidelberg Instruments DWL 66FS laser mask writer, and plastic photomasks were procured from CAD/ART Inc. Glass masks were used as-is, whereas plastic masks were mounted on a clear ¼" thick glass. The lithography was carried out in hard-contact mode with interval exposure methodology. An exposure of ultraviolet (UV) light was given in doses of 75 mJ/$cm^2$ with an intermediate wait period of 5 seconds for a total of exposure dosage of 1350 mJ/$cm^2$. The exposure was carried out at 365/405 nm wavelength, whereas the hard contact pressure was adjusted to 1.5 PSI.

To remove the photoresist from the UV-exposed areas of the wafer, a solution of AZ® 400 developer (from Microchemicals GmbH) was used. 30 ml AZ® 400 concentrated stock solution was diluted with 120 ml of de-ionized water. Development time was adjusted to between 1.5 minutes and 6 minutes based on thickness of the photoresist and intensity of exposure. For typical 7 micrometer thickness of photoresist, the development time was ~2 minutes. After development, the wafer was washed using DI water and blow dried using nitrogen gun.

To etch the microwells into the silicon wafers, an anisotropic etching process was used. The wafer was treated with the Bosch Deep Reactive Ion Etching (DRIE) process on a Plasmalabsystems 180 instrument (Oxford Instruments, Inc). The process was carried using alternating cycles of passivation of silicon substrate using octafluorocyclobutane ($C_4F_8$) and isotropic etching by sulfurhexafluoride ($SF_6$). The chamber pressure was maintained at 35 mTorr, and the flow rates were kept at 100 and 45 sccm for $SF_6$ and $C_4F_8$ respectively. The ICP (Inductively Coupled Plasma) power was maintained at 700 W, whereas the CCP (capacitatively coupled plasma) power for etch and passivation cycles was maintained at 40 W and 15 W respectively, for a duration of 7 s per cycle. The etching depth was evaluated by Zeta Instruments optical scanner or by Alpha-Step IQ surface profiler, and an etch depth of ~150 to ~200 micrometers was targeted and achieved.

To strip any remaining photoresist and residue from the DRIE process from the etched wafer, it was treated in an AutoGlow oxygen plasma machine (from GlowResearch Inc.). The wafer was treated for 5 minutes in oxygen plasma controlled at 300 W and at 300 mTorr pressure. The wafer was then washed sequentially (for 5 minutes in each solvent) in 1-Methyl-2-pyrrolidinone (NMP), Acetone and Isopropyl alcohol (IPA) (all from J.T. Baker Inc.). The wafer was then blow-dried with a nitrogen gun.

To remove any oxide from the surface of the silicon wafer, it was dipped in BOE 10:1 solution for 15 minutes. The wafer was then washed with deionized water, and then baked to dry at 150° C. for at least 2 minutes. To then remove any organic contamination from the surface of the wafer, it was cleaned with piranha solution. The piranha solution was prepared by mixing concentrated sulfuric acid with 30% hydrogen peroxide (both from J. T. Baker). For a typical 4:1 piranha, 20 ml of hydrogen peroxide solution was slowly added to a bath of 80 ml sulfuric acid. The wafers were dipped in the bath for 10 minutes. The wafer was then washed with deionized water, and baked at 150° C. for at least 2 minutes to dry it.

The wafer was then diced (cut) into individual chips of approximately 1.5×1.5 cm, each containing thousands of microwells. Each chip is intended to enable compartmentalized PCR to be performed on an individual DNA sample. The chips were then coated with silicon dioxide using the process of plasma-enhanced chemical vapor deposition (PECVD) with a GSI UltraDep 1000 instrument. The mounting base was heated at 200° C. A silicon dioxide coating of ~1000 nm was deposited in 450 seconds at 200° C. The thickness of the oxide was confirmed optically using a Nanometrics instrument.

The chips were then immersed in pure ethanol (anhydrous, 200 Proof from Decon Laboratories Inc.) and the solution was heated slowly on a hotplate at 90° C. for 30 minutes. Without drying, the chips were immersed in deionized water at room temperature for 10 mins. A Piranha solution of $H_2SO_4$:$H_2O_2$ in the ratio of 4:1 was prepared in a beaker by carefully adding hydrogen peroxide to concentrated sulfuric acid. For the preparation, 10 ml of concentrated sulfuric acid (ACS reagent, 320501, from Sigma Aldrich) was mixed with 2.5 ml of 30% $H_2O_2$ (#2186 from J. T. Baker®). The silicon chips were dipped into the Piranha solution, and heated to 100° C. for 30 minutes. The chips were removed from the Piranha solution and washed in de-ionized water, and dried at 100° C. on a hotplate.

To make the surface of the chips bio-compatible for PCR, the surface was coated with polyethylene glycol (PEG). The PEG treatment was done immediately after the Piranha step (after rinsing the chips in water and drying). A solution of 2 mM m-PEG Silane (MW 5000, #M-SIL-5K from Laysan Bio, Inc.) was freshly prepared in 1 ml/chip anhydrous toluene solution with 0.8 microliters/ml HCl (conc.). Both toluene (#244511) and hydrochloric acid (#H1758) were purchased from Sigma Aldrich. The chips were immersed in the PEG-toluene solution and sonicated for 5 minutes in an ultrasonic bath to promote penetration of the solution into the microwells of the chips. The chips were incubated in the PEG-toluene solution for 12 hours. The chips were then sequentially washed in pure toluene, pure ethanol, and de-ionized water. The chips were finally blow-dried using nitrogen and were stored in a desiccator for future use.

Figure 13:
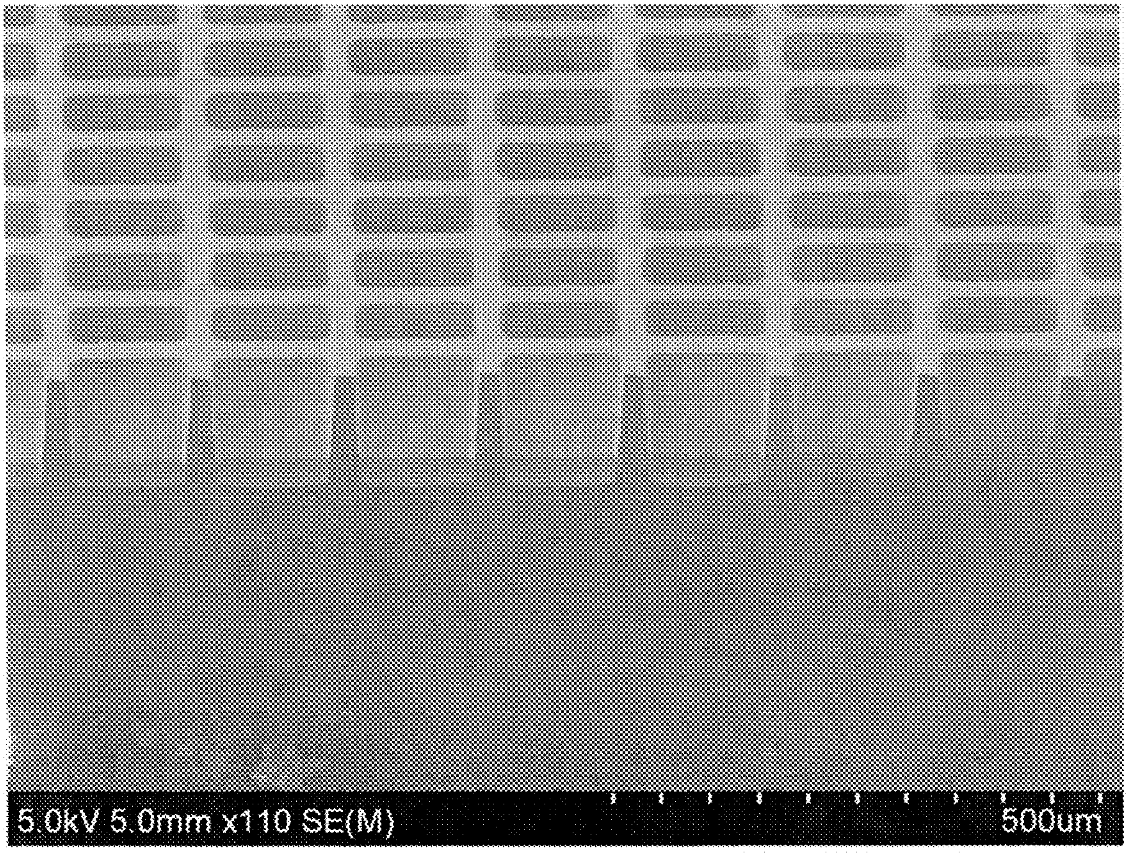
FIG. 13 shows a scanning electron micrograph of an example silicon chip containing micro-wells produced using the methods described in Example 3.

A scanning electron micrograph of an example silicon chip with etched micro-wells is shown in FIG. 13.

Example 4

Figure 14:
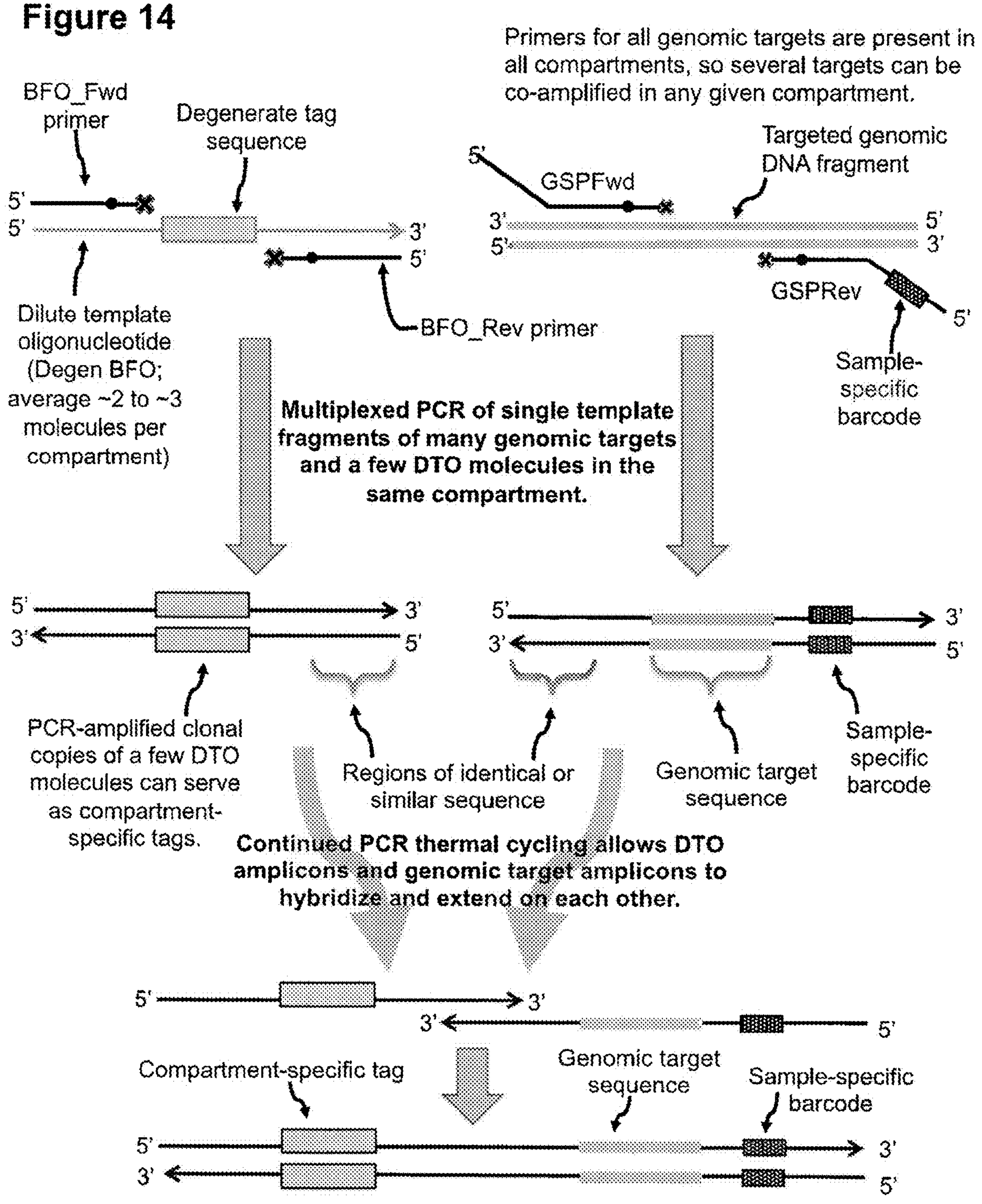
FIG. 14 shows a schematic of compartmentalized multiplexed PCR in which multiple genomic target molecules and a few dilute template oligonucleotide (DTO) molecules are simultaneously amplified in a given compartment (e.g., a micro-well). Amplification of the degenerate sequence region of a DTO molecule produces many clonal copies of an arbitrary sequence which can serve as a compartment-specific tag. Amplified copies of the DTO molecules and genomic DNA in a given compartment can become concatenated into extended amplicons via hybridization of common sequence elements between the DTO primers and the genomic DNA primers. The extended amplicons contain targeted genomic DNA sequences attached to compartment-specific tags.

This example further describes methods and systems that are directed to sensitive and efficient measurement of low-abundance variant sequences within complex nucleic acid mixtures. Specifically, this example describes how the silicon chips containing micro-wells (described in Example 3) have been used to perform compartmentalized PCR for preparation of next-generation sequencing libraries. This example describes how a chip can be encased in a container (housing) which can be filled with oil, serving to isolate the aqueous contents of each micro-well from the contents of other micro-wells. The example describes how the container can be sealed, thermocycled to enable PCR, and the amplification products then recovered from the micro-wells and purified for subsequent next-generation sequencing. This example also describes implementation of a modified version of the bead-free method to introduce clonal primers containing compartment-specific tags, as described in FIG. 14. By adding to the PCR cocktail dilute template oligonucleotides (DTOs) which contain degenerate sequence positions, it is possible to produce compartment-specific tags that can be used to label the PCR products of the genomic targets that are co-amplified in the same compartment. In this example, the DTOs are added to the PCR cocktail at a concentration such that after compartmentalization of the cocktail into micro-wells, each compartment contains an average of ~2-3 individual DTO molecules (and each DTO molecule contains a unique tag sequence). The DTOs serve as seed molecules that can be clonally amplified by PCR within a compartment, to introduce a small number of unique sequence tags to each compartment. Primers are included in the cocktail that can PCR-amplify the DTO molecules within each compartment, producing many clonal copies of the unique tag sequence of the DTO. These clonally-amplified DTO copies (containing compartment-specific tags) can act as primers by hybridizing to and being extended on PCR-amplified copies of genomic targets within the same compartment, as schematized in FIG. 14. In this way, genomic targets (typically a single copy for any given target in a compartment) can be amplified by PCR within a compartment and the amplification products can be labeled with one or a few unique, compartment-specific tags originating from the DTO tag sequences. The example can be applied to analysis of samples containing double-stranded DNA templates, to single-stranded DNA templates, to complementary DNA (cDNA) generated by reverse-transcription of RNA, or to nucleic acid templates derived from single cells.

Encasement of the Silicon Chip into a Container which can be Filled with Oil and Thermo-Cycled:

The silicon chip described in Example 3 was mounted in a custom-made housing (container) consisting of an aluminum base and a plastic lid. The base was made of aluminum so that it could efficiently transmit heat from and to a heating block of a thermal cycler instrument (PCR machine). The thermal cycler was fitted with a flat heating block so that the aluminum housing of the chip, which had a flat base, could make direct contact the heating block over a broad surface to promote efficient heat-transfer. The chip was mounted on the aluminum base using thermally-conductive double-sided adhesive tape (product #8805 from 3M, Inc). The tape was adherent to the top of the aluminum base, and to the back-side of the silicon chip, so that the front-side containing the microwells was exposed and facing up.

PCR Reaction Mix (Cocktail):

The following PCR reaction cocktail was made in a single tube to load into the micro-wells of the silicon chip:

Purified template DNA (0.1 to 200 ng; may contain carrier RNA) 9.6 μL

5× concentrated Phusion HF Buffer (Thermo Fisher #F549L) 3 μL

Mix of 4 dNTPs, stock solution of 10 mM each (NEB #N0447S) 0.3 μL

Mix of GSPFwd1-12 and GSPRev1-12 primers (Table 2; 0.6 μM each) 0.5 μL

Mix of BFO_Fwd and BFO_Rev primers (Table 2; 3 μM each) 0.5 μL

DegenBFO (Dilute Template Oligo) (Table 2; Total ~$5\times10^4$ molecules) 0.5 μL Phusion Hot Start II DNA Polymerase (Thermo Fisher) (2 U/μL stock) 0.3 μL RNAse $H_2$ (Integrated DNA Technologies) (20 mU/μL stock) 0.3 μL (Total final volume 15 μL)

TABLE 2

| | Primer Sequence |
|---|---|
| **Gene-specific Forward Primers:** | |
| GSPFwd1 (KRAS1) | CTACTCACTGCTCTCGACCGTCTGTWWWAGGCCTGCTGAAAATGACTGAATATAaACTTXX (SEQ ID No: 32) |
| GSPFwd2 (KRAS2) | CTACTCACTGCTCTCGACCGTCTGTWWWGAAACCTGTCTCTTGGATATTCTcGACAXX (SEQ ID No: 33) |
| GSPFwd3 (EGFR1) | CTACTCACTGCTCTCGACCGTCTGTWWWGGATCCCAGAAGGTGAGAAAGTTAAaATTCXX (SEQ ID No: 34) |
| GSPFwd4 (EGFR2) | CTACTCACTGCTCTCGACCGTCTGTWWWAAAACACCGCAGCATGTCAAgATCAXX (SEQ ID No: 35) |
| GSPFwd5 (EGFR3) | CTACTCACTGCTCTCGACCGTCTGTWWWCATCTGCCTCACCTCCAcCGTGXX (SEQ ID No: 36) |
| GSPFwd6 (EGFR4) | CTACTCACTGCTCTCGACCGTCTGTWWWTCCCAACCAAGCTCTCTTGaGGATXX (SEQ ID No: 37) |
| GSPFwd7(PIK3CA1) | CTACTCACTGCTCTCGACCGTCTGTWWWCAGCTCAAAGCAATTTCTACACGaGATCXX (SEQ ID No: 38) |
| GSPFwd8 (PIK3CA2) | CTACTCACTGCTCTCGACCGTCTGTWWWAAACTGAGCAAGAGGCTTTGgAGTAXX (SEQ ID No: 39) |
| GSPFwd9 (BRAF) | CTACTCACTGCTCTCGACCGTCTGTWWWTTCTTCATGAAGACCTCACAGTAAAaATAGXX (SEQ ID No: 40) |
| GSPFwd10 (IDH1) | CTACTCACTGCTCTCGACCGTCTGTWWWTTGTGAGTGGATGGGTAAAACcTATCXX (SEQ ID No: 41) |
| GSPFwd11 (U2AF) | CTACTCACTGCTCTCGACCGTCTGTWWWAAATTGGAGCATGTCGTCATgGAGAXX (SEQ ID No: 42) |
| GSPFwd12 (FLT3) | CTACTCACTGCTCTCGACCGTCTGTWWWCCCACGGGAAAGTGGTGAAGaTATGXX (SEQ ID No: 43) |
| **Gene specific Reverse Primers:** | |
| GSPRev1 (KRAS1) | CAAGCAGAAGACGGCATACGAGAT[**BC**]GTGACTGGAGTTCAGACGTGTGCTCTTCCGATCTWWWCTGAATTAGCTGTATCGTCAAGgCACTXX (SEQ ID No: 44) |
| GSPRev2 (KRAS2) | CAAGCAGAAGACGGCATACGAGAT[**BC**]GTGACTGGAGTTCAGACGTGTGCTCTTCCGATCTWWWCTCATGTACTGGTCCCTCATTgCACTXX (SEQ ID No: 45) |
| GSPRev3 (EGFR1) | CAAGCAGAAGACGGCATACGAGAT[**BC**]GTGACTGGAGTTCAGACGTGTGCTCTTCCGATCTWWWAGCAGAAACTCACATCGAGGaTTTCXX (SEQ ID No: 46) |
| GSPRev4 (EGFR2) | CAAGCAGAAGACGGCATACGAGAT[**BC**]GTGACTGGAGTTCAGACGTGTGCTCTTCCGATCTWWWTGCCTCCTTCTGCATGGTATTcTTTCXX (SEQ ID No: 47) |
| GSPRev5 (EGFR3) | CAAGCAGAAGACGGCATACGAGAT[**BC**]GTGACTGGAGTTCAGACGTGTGCTCTTCCGATCTWWWAGCCAATATTGTCTTTGTGTTcCCGGXX (SEQ ID No: 48) |
| GSPRev6 (EGFR4) | CAAGCAGAAGACGGCATACGAGAT[**BC**]GTGACTGGAGTTCAGACGTGTGCTCTTCCGATCTWWWAGGGACCTTACCTTATACACcGTGCXX (SEQ ID No: 49) |
| GSPRev7 (PIK3CA1) | CAAGCAGAAGACGGCATACGAGAT[**BC**]GTGACTGGAGTTCAGACGTGTGCTCTTCCGATCTWWWATCTCCATTTTAGCACTTACCTgTGACXX (SEQ ID No: 50) |
| GSPRev8 (PIK3CA2) | CAAGCAGAAGACGGCATACGAGAT[**BC**]GTGACTGGAGTTCAGACGTGTGCTCTTCCGATCTWWWTCCAATCCATTTTTGTTGTCCaGCCAXX (SEQ ID No: 51) |
| GSPRev9 (BRAF) | CAAGCAGAAGACGGCATACGAGAT[**BC**]GTGACTGGAGTTCAGACGTGTGCTCTTCCGATCTWWWACTGTTCAAACTGATGGGACcCACTXX (SEQ ID No: 52) |
| GSPRev10 (IDH1) | CAAGCAGAAGACGGCATACGAGAT[**BC**]GTGACTGGAGTTCAGACGTGTGCTCTTCCGATCTWWWCATTATTGCCAACATGACTTACTTgATCCXX (SEQ ID No: 53) |
| GSPRev11 (U2AF) | CAAGCAGAAGACGGCATACGAGAT[**BC**]GTGACTGGAGTTCAGACGTGTGCTCTTCCGATCTWWWTGGCTAAACGTCGGTTTATTgTGCAXX (SEQ ID No: 54) |

TABLE 2-continued

| | Primer Sequence |
|---|---|
| GSPRev12 (FLT3) | CAAGCAGAAGACGGCATACGAGAT[**BC**]GTGACTGGAGTTCAGACGTGTGCTCTTCCGATCTW WWCCTCACATTGCCCCTGACAAcATAGXX (SEQ ID No: 55) |
| Universal Primers | |
| BFO_Fwd | AATGATACGGCGACCACCGAGATcTACAXX (SEQ ID No: 56) |
| BFO_Rev | GTCGAGAGCAGTGAGTAGGTGcGTAGXX (SEQ ID No: 57) |
| DegenBFO | AATGATACGGCGACCACCGAGATCTACACNNNNNNNNNNNNNACTACGCACCTACTCACTGCTC TCGACCGTCTG (SEQ ID No: 58) |

Notes for Table 2
X = inverse dA (Glen Research #10-0001-02 and #20-0012-42)
Residues in lower case are RNA; Residues in upper case are DNA.
[BC] = sample-specific barcode; each sample-specific barcode was 8 nucleotides long and differed from all other barcodes at a minimum of 2 positions.
N = degenerate position with equal probability of incorporating A, T, C, or G.
W = degenerate position with equal probability of incorporating A or T.

The concentration of the degenerate Dilute Template Oligonucleotide (DTO; also called DegenBFO in Table 2) solution was adjusted so that an average of ~2 to ~3 amplifiable molecules would be distributed into each compartment of the silicon chip. For example, if the chip has ~20,000 compartments, we would adjust the concentration of the DTO such that the µL PCR cocktail contained ~40,000 to ~60,000 amplifiable DTO molecules. We aimed to have average of ~2 to ~3 amplifiable DTO molecules per compartment so that the probability of a compartment having 0 molecules would be low (according to Poisson statistics). Digital PCR experiments were conducted using various concentrations of the DTO templates to accurately determine the concentration of amplifiable molecules.

Loading PCR Cocktail into Silicon Chip Micro-Wells and Isolating Micro-Wells with Oil:

The PCR cocktail (15 µL total volume) was loaded onto the silicon chip by placing the entire volume onto the surface of the chip with a pipette and spreading it across the surface of the chip using the side of a fresh polypropylene 200 µL pipette tip. The side surface of the conical pipette tip was brought in contact with the surface of the chip, and the PCR cocktail was spread across the surface of the chip using the pipette tip in a squeegee-like motion to push the solution. The aqueous PCR cocktail was drawn into the micro-wells on the surface of the silicon chip by capillary force. After spreading the aqueous PCR cocktail over the surface of the chip, most of the aqueous solution was contained within micro-wells, and very little was remaining on the surface outside of the micro-wells. The chip was then heated to ~37° C. on an aluminum heating-block for ~90 seconds to dry any excess PCR cocktail that remained on the chip surface and did not enter a micro-well (since the chip was already mounted on the aluminum housing base, the aluminum housing base was placed on the heating-block with the chip on the base).

Degassed Fluorinert FC40 fluorinated oil (3M, Inc.) was added using a pipette in sufficient quantity to entirely cover the top surface of the chip without spilling over the edge of the chip. The purpose of the oil was to act as a barrier against further evaporation of the aqueous PCR cocktail from the micro-wells and to prevent exchange of molecules across different micro-wells. After adding the oil on top of the chip, a rigid plastic cover (made of polycarbonate) was placed over the chip and held tightly in place with clips, forming an airtight seal with the aluminum base. A silicone gasket was sandwiched between the aluminum base and the plastic cover to ensure a good seal. In this way, the silicon chip was housed between the aluminum base and the plastic cover. A small opening (port) in the plastic cover was used to add more degassed Fluorinert FC-40 oil (3M, Inc.) in the space surrounding the chip, until the chamber was almost completely filled and there was very little air left (<3 µL) in the chamber between the aluminum base and the plastic cover. Once the oil was almost completely filling the chamber, a small piece of adhesive tape was used to seal the port in the plastic cover so that the oil was completely sealed within the housing (and the silicon chip was completely immersed in the oil).

Thermo-Cycling of the Sealed Silicon Chip:

The sealed chamber (housing) containing the silicon chip was placed on a thermo-cycler with a flat heating block adapter. A Bio-Rad T100 thermo-cycler with a standard 96-well heating block was used in conjunction with a Techne in-situ hybridization adapter (Fisher Scientific Cat #13-245-153) to create a flat heating surface. The silicon chip bathed in oil within the sealed chamber (housing) was placed on the flat heating surface of the thermo-cycler, with the aluminum base making direct contact with the flat metallic heating surface to ensure good heat exchange. Multiple chips could be thermo-cycled simultaneously on a single heating block. The thermo-cycler was run using the following parameters:

Temperature Cycling Conditions:

a. 98° C. for 120 sec
b. 98° C. for 60 sec
c. 70° C. slowly decreased to 62° C. at rate of 1° C. per 10 sec
d. 62° C. for 2 min
e. 72° C. for 60 sec
f. repeat steps b-e for 3 more cycles (total 4 cycles)
g. 98° C. for 60 sec
h. 62° C. for 120 sec
i. 72°° C. for 60 sec
j. repeat steps g-i for 30 more cycles (total 31 cycles)
k. 98° C. for 60 sec
l. 55° C. for 120 sec
m. 72° C. for 60 sec
n. repeat steps k-m for 3 more cycle (total 4 cycles)
o. hold at 4° C.

Recovery and Purification of Amplified DNA Products from the Silicon Chip Micro-Wells:

Upon completion of the thermal cycling, the tape was removed from the port on the plastic cover to provide access to the chamber. A pipette was used to drain the oil completely from the chamber. Then, 120 µL of extraction solution (consisting of 50 mM NaCl and 10 mM EDTA) was added to the chamber such that the solution was in direct contact with the entire surface of the silicon chip for at approximately 30 minutes. The amplified PCR products in the micro-wells were recovered from the micro-wells by diffusion into the extraction solution. The extraction solution containing the PCR products was then removed from the housing chamber using a pipette, and the DNA was isolated from the extraction solution using Agencourt AMPure XP beads (Beckman Coulter, #A63881).

150 μL of AMPure XP bead slurry was added to 100 μL of recovered extraction solution containing PCR-amplified products in a 1.5 mL microfuge tube. Isolation of DNA was performed according to the instructions provided by the manufacturer of the kit. The mixture of bead slurry and extraction solution was allowed to incubate at room temperature for ~5 minutes to allow the DNA fragments to bind to the paramagnetic beads. Then, a magnet was used to pull the beads (with bound DNA fragments) to one side of the tube, and the remaining supernatant solution was removed from the tube using a pipette. The beads were then washed by adding 400 μL of a wash solution containing 80% ethanol to immerse the beads, incubating for 30 seconds at room temperature, and removing the wash solution with a pipette. The wash was repeated once more with a second, fresh volume of 400 μL wash solution. After removing the second wash solution, the beads were allowed to dry for 2 minutes at room temperature to allow any remaining traces of ethanol to evaporate. Finally, the DNA fragments were eluted from the surface of the magnetic beads by adding 30 μL of aqueous elution buffer containing 10 mM Tris-Cl (pH 7.6). The tube was removed from the magnet to allow the beads to float free in the elution buffer for 2 minutes. The elution buffer allowed the purified DNA fragments to be released from the surface of the magnetic beads and into the solution. A magnet was then used to pull the beads once again to the side of the tube so that the elution buffer containing the purified, eluted DNA fragments could be recovered from the tube with a pipette and transferred to a fresh, new microfuge tube.

Next-Generation Sequencing and Data Analysis:

The purified PCR products were prepared for next-generation sequencing by measuring the concentration of DNA using an Agilent Bioanalyzer, and quantitative PCR. The DNA was then diluted to the concentration recommended for loading onto an Illumina HiSeq 2500 flow cell (according to manufacturer's specifications). Cluster formation was carried out on the flow cell according to Illumina's protocol. The sample was loaded onto a single lane of a flow cell. The sequencing was performed on a HiSeq® 2500 instrument in paired-end mode, with a read length of 75 base pairs in each direction (2×75 bp mode). In additional experiments, sequencing has also been performed on an Illumina MiSeq instrument, and paired-end read lengths of 100 or 150 base pairs in each direction have also been utilized. Two index reads were also performed, with the lengths of the first and second index reads being 8 bases and 12 bases, respectively. A special custom sequencing primer had to be added to the Illumina-supplied sequencing primer cocktail for sequencing of Read 1 (as defined in the Illumina workflow). This special primer was needed because the region in the PCR amplicons to which the standard Read 1 primer typically binds was replaced with a non-standard sequence. The primer which was supplemented in the Illumina Read 1 primer cocktail had the following sequence:

```
Supplemented Read 1 Primer:
                                    (SEQ ID NO: 59)
ACTACGCACCTACTCACTGCTCTCGACCGTCTGT
```

Analysis of sequence data was performed as described in Example 2 and in the "Methods" section.

Example 5

This example also describes methods and systems that are directed to sensitive and efficient measurement of low-abundance variant sequences within complex nucleic acid mixtures. Specifically, this example describes a method in which double-stranded DNA fragments obtained from a biological sample are ligated to partially or fully double-stranded adapter oligonucleotides which enable PCR-amplification, optional hybrid-capture-based enrichment, and next-generation sequencing of the biologically-derived DNA fragments (schematized in FIG. 15). Importantly, this approach uses multiple different adapter sequences simultaneously in a single ligation reaction, so that there is a high probability (>49%) that 2 different adapter sequences are ligated to the two ends of any given double-stranded DNA fragment of biological origin (known as the DNA insert). This is in contrast to most standard adapter ligation methods, in which a single Y-shaped adapter (where the ligatable end is mostly double-stranded and the PCR-primer binding regions are single-stranded) is ligated to the two ends of any given double-stranded DNA insert fragment. Because multiple possible combinations of adapter sequences can be ligated to the two ends of a given insert, it is possible to use both the beginning and end positions of the insert sequence and the specific adapter combination to identify individual insert molecules. Furthermore, the adapters are designed to have at least one non-complementary (mismatched) base pair (such as G:T) so that PCR-amplification products derived from the top strand of the adapter-ligated insert can be distinguished from those derived from the bottom strand of the same adapter-ligated insert. By comparing PCR-amplified sequences arising from both strands of a double-stranded DNA insert fragment, a variant (mutation) can be identified with very high confidence if the sequence is confirmed to be present on both strands of the DNA insert fragment. On the other hand, if a variant sequence is found on only one of the two DNA strands of a DNA insert fragment, it is likely to be arising from either a damaged DNA base (present on one strand, but not the opposite strand), a PCR polymerase nucleotide misincorporation error, or a sequencing error. This approach can be used to enable very high-confidence variant calling from virtually any source of double-stranded DNA, including but not limited to circulating cell-free DNA, tumor tissue DNA (including formalin-fixed, paraffin-embedded tissue), germline DNA, and DNA derived from single cells or a small number of cells. This approach also enables broader mutation coverage than is generally possible with PCR-amplicon-based preparation of next-generation sequencing libraries. Detailed methods used in this example are described below.

Ligation of Double-Stranded DNA Insert Molecules to Multiple (Non-Y-Shaped) Adapters:

In this example, DNA insert molecules were obtained from the plasma of a patient with advanced-stage lung cancer. DNA was extracted from 1 mL of EDTA-plasma, using the methods that were detailed in Example 1. The yield of cell-free DNA from 1 mL of patient plasma is usually in the range of approximately 5-10 ng, although it can be as high as 100 ng and as low as 1 ng (or even less). To prepare the ends of the insert DNA molecules for ligation of adapters, the insert DNA (approximately 5-10 ng of DNA in 10 μL of 10 mM Tris, pH 7.5) was added to 1.4 μL of NEBNext Ultra II End Prep Reaction buffer and 0.6 μL of NEBNext Ultra II End Prep Enzyme Mix (both obtained from New England Biolabs). The solution was mixed well and incubated at 20° C. for 30 minutes, followed by 65° C. for 30 minutes. After the completion of the end-preparation reaction, ligation of adapters to DNA inserts was achieved by the addition of 2.2 μL of adapter mix (20 adapters total, working stock of 20 nM of each adapter; sequences listed in Table 3), 7.5 μL of NEBNext Ultra II Ligation Master Mix and 0.25 μL of NEBNext Ligation Enhancer (New England Biolabs). The mixture was incubated at 20° C. for 1 hour, after which 44 μL of Agencourt Ampure XP beads (Beckman Coulter) were added. After 10 minutes incubation at room temperature, the solution was placed on a magnetic rack to separate the beads and the supernatant was discarded. The beads were washed twice with 80% ethanol in water (2×150 μL) and left to dry for 10 minutes. The beads were resuspended in 10 μL of 10 mM Tris (pH 7.5) off the magnetic rack and incubated for 10 minutes. The mixture was then placed on the magnetic rack to separate the beads and the supernatant containing the ligated DNA product was transferred to a new microcentrifuge tube.

PCR-Amplification of Adapter-Ligated Insert DNA Molecules:

The ligated DNA product (in 10 μL of 10 mM Tris, pH 7.5) was used in a real-time PCR amplification (25 μL total volume) containing 5 μL of 5× Phire reaction buffer (Thermo Fisher), 0.5 μL of dNTP mix (10 mM of each dNTP), 1.5 μL SYBR Green (1× working stock in water), 2.5 μL of primer mix (20 primers total, working stock of 1 μM of each primer, listed in Table 4), 2.5 μL of RNase $H_2$ solution (working stock of 50 mU/μL; Integrated DNA Technologies), 2.5 μL of water and 0.5 L of Phire Hot Start II DNA Polymerase (Thermo Fisher). Thermal cycling for PCR was carried out on a real-time PCR machine (Bio-Rad IQ5). The cycling parameters were as follows: 1 cycle of 98° C. for 30 seconds, then a maximum of 20 cycles of [98° C. for 10 seconds, 55° C. for 55 seconds and 72° C. for 55 seconds]. Instead of carrying out the PCR for a fixed number of cycles, the fluorescence signal was followed on the real-time PCR machine, and the tube was removed when the signal was nearing saturation (plateau phase). Typically for ~5-10 ng of cell-free DNA, tubes were removed after ~11-13 cycles. To remove a tube, the PCR machine was paused during a 72° C. incubation period with the temperature maintained at 72° C. for at least 1 minute before removing the tube to promote complete polymerase extension on existing template DNA strands. After the completion of the PCR, 50 μL of Ampure XP beads were added to the reaction mixture and incubated for 10 minutes at room temperature. The mixture was placed on a magnetic rack to separate the beads. The supernatant was discarded, and the beads were washed twice with 80% ethanol in water (2×150 μL) and left to dry for 10 minutes. The beads were resuspended in 10 μL of 10 mM Tris (pH 7.5) off the magnetic rack and incubated for 10 minutes. The mixture was then placed back on the magnetic rack to pull the beads to the side of the tube, and the supernatant containing the PCR-amplified product was transferred to a new microcentrifuge tube.

TABLE 3

Adapter Sequences

| Oligonucleotide name (top strand) | Adapter top strand sequence (no phosphate on 5'-end) |
|---|---|
| TS1 | TAAGCAGCGGCTACCACCATTGTTACGAGTGCAACAT (SEQ ID No: 60) |
| TS2 | CCGGCATCAGTCAATGCCTCAATGTGATCAGCAACAT (SEQ ID No: 61) |
| TS3 | GGTCGACGCAAGCGATTACACTTGAACTGTCCAACAT (SEQ ID No: 62) |
| TS4 | AGTTCGGTCAGAGCGTCATTGCTAGTGATGCCAACAT (SEQ ID No: 63) |
| TS5 | GCACCATCCATTGTCGTGGTGATACATGACGCAACAT (SEQ ID No: 64) |
| TS6 | TGGCTGTGCTTGGAGTCAATCGTAGACTGTGCAACAT (SEQ ID No: 65) |
| TS7 | AACTCAGGTCCGTGTCGGAAGATGACTTGACCAACAT (SEQ ID No: 66) |
| TS8 | CGTTGAACGCTACACGGACGATTGTCAGTTCCAACAT (SEQ ID No: 67) |
| TS9 | CGGATCGGAGCTCGATTGTGTCTTGAGCTAGCAACAT (SEQ ID No: 68) |
| TS10 | CTCGTGCAACTTCGGCTAACCATGTTCGATGCAACAT (SEQ ID No: 69) |
| TS11 | TTCGCACCGCTCATACACTTGGTATAGACTCCAACAT (SEQ ID No: 70) |
| TS12 | ACGTGGCTGAACAAGTCGTAGCTTTCAGTACCAACAT (SEQ ID No: 71) |
| TS13 | CACGTCCGCGTAGTTGAATCGTTAGATGTAGCAACAT (SEQ ID No: 72) |
| TS14 | CCATCGGCGACGAATAGCAGTTTGTACATCGCAACAT (SEQ ID No: 73) |
| TS15 | GCGGCTAGGAACGCAACAAGTATGATGAGTCCAACAT (SEQ ID No: 74) |
| TS16 | GACGCGAGATGCTGGTTGTCTTTCAACTAGGCAACAT (SEQ ID No: 75) |
| TS17 | TACCGGTCACCAGCCAACAATGTATCATAGCCAACAT (SEQ ID No: 76) |
| TS18 | GCTCGGTAACACACGGTCTAGCTTACTAGAGCAACAT (SEQ ID No: 77) |

TABLE 3-continued

| Adapter Sequences | |
|---|---|
| TS19 | TACCACGCTGGCTAGCAACAACTAGTCGATCCAACAT (SEQ ID No: 78) |
| TS20 | GCCAGCGTGGTAAGTAACAGCATCAGTCATGCAACAT (SEQ ID No: 79) |
| Oligonucleotide name (bottom strand) | Adapter bottom strand sequence (X = inverse dA (Glen Research #10-0001-02 and #20-0012-42; P = 5'-phosphate added during oligo synthesis). |
| BS1 | P-TGTTGCACTCGTAGCAATGGTGGTAGCCGCTGCTTA-XX (SEQ ID No: 80) |
| BS2 | P-TGTTGCTGATCACGTTGAGGCATTGACTGATGCCGG-XX (SEQ ID No: 81) |
| BS3 | P-TGTTGGACAGTTCGAGTGTAATCGCTTGCGTCGACC-XX (SEQ ID No: 82) |
| BS4 | P-TGTTGGCATCACTGGCAATGACGCTCTGACCGAACT-XX (SEQ ID No: 83) |
| BS5 | P-TGTTGCGTCATGTGTCACCACGACAATGGATGGTGC-XX (SEQ ID No: 84) |
| BS6 | P-TGTTGCACAGTCTGCGATTGACTCCAAGCACAGCCA-XX (SEQ ID No: 85) |
| BS7 | P-TGTTGGTCAAGTCGTCTTCCGACACGGACCTGAGTT-XX (SEQ ID No: 86) |
| BS8 | P-TGTTGGAACTGACGATCGTCCGTGTAGCGTTCAACG-XX (SEQ ID No: 87) |
| BS9 | P-TGTTGCTAGCTCAGGACACAATCGAGCTCCGATCCG-XX (SEQ ID No: 88) |
| BS10 | P-TGTTGCATCGAACGTGGTTAGCCGAAGTTGCACGAG-XX (SEQ ID No: 89) |
| BS11 | P-TGTTGGAGTCTATGCCAAGTGTATGAGCGGTGCGAA-XX (SEQ ID No: 90) |
| BS12 | P-TGTTGGTACTGAAGGCTACGACTTGTTCAGCCACGT-XX (SEQ ID No: 91) |
| BS13 | P-TGTTGCTACATCTGACGATTCAACTACGCGGACGTG-XX (SEQ ID No: 92) |
| BS14 | P-TGTTGCGATGTACGAACTGCTATTCGTCGCCGATGG-XX (SEQ ID No: 93) |
| BS15 | P-TGTTGGACTCATCGTACTTGTTGCGTTCCTAGCCGC-XX (SEQ ID No: 94) |
| BS16 | P-TGTTGCCTAGTTGGAAGACAACCAGCATCTCGCGTC-XX (SEQ ID No: 95) |
| BS17 | P-TGTTGGCTATGATGCATTGTTGGCTGGTGACCGGTA-XX (SEQ ID No: 96) |
| BS18 | P-TGTTGCTCTAGTAGGCTAGACCGTGTGTTACCGAGC-XX (SEQ ID No: 97) |
| BS19 | P-TGTTGGATCGACTGGTTGTTGCTAGCCAGCGTGGTA-XX (SEQ ID No: 98) |
| BS20 | P-TGTTGCATGACTGGTGCTGTTACTTACCACGCTGGC-XX (SEQ ID No: 99) |

TABLE 4

| PCR Primers | |
|---|---|
| Primer name | Primer Sequence |
| PCR1 | TAAGCAGCGGCTACCACrCATTGA/3SpC3/ (SEQ ID No: 100) |
| PCR2 | CCGGCATCAGTCAATGCrCTCAAA/3SpC3/ (SEQ ID No: 101) |
| PCR3 | GGTCGACGCAAGCGATTrACACTA/3SpC3/ (SEQ ID No: 102) |
| PCR4 | AGTTCGGTCAGAGCGTCrATTGCA/3SpC3/ (SEQ ID No: 103) |
| PCR5 | GCACCATCCATTGTCGTrGGTGAA/3SpC3/ (SEQ ID No: 104) |
| PCR6 | TGGCTGTGCTTGGAGTCrAATCGA/3SpC3/ (SEQ ID No: 105) |
| PCR7 | AACTCAGGTCCGTGTCGrGAAGAA/3SpC3/ (SEQ ID No: 106) |

TABLE 4-continued

| PCR Primers | |
|---|---|
| Primer name | Primer Sequence |
| PCR8 | CGTTGAACGCTACACGGrACGATA/3SpC3/ (SEQ ID No: 107) |
| PCR9 | CGGATCGGAGCTCGATTrGTGTCA/3SpC3/ (SEQ ID No: 108) |
| PCR10 | CTCGTGCAACTTCGGCTrAACCAA/3SpC3/ (SEQ ID No: 109) |
| PCR11 | TTCGCACCGCTCATACArCTTGGA/3SpC3/ (SEQ ID No: 110) |
| PCR12 | ACGTGGCTGAACAAGTCrGTAGCA/3SpC3/ (SEQ ID No: 111) |
| PCR13 | CACGTCCGCGTAGTTGArATCGTA/3SpC3/ (SEQ ID No: 112) |

TABLE 4-continued

| PCR Primers | |
|---|---|
| Primer name | Primer Sequence |
| PCR14 | CCATCGGCGACGAATAGrCAGTTA/3SpC3/ (SEQ ID No: 113) |
| PCR15 | GCGGCTAGGAACGCAACrAAGTAA/3SpC3/ (SEQ ID No: 114) |
| PCR16 | GACGCGAGATGCTGGTTrGTCTTA/3SpC3/ (SEQ ID No: 115) |
| PCR17 | TACCGGTCACCAGCCAArCAATGA/3SpC3/ (SEQ ID No: 116) |
| PCR18 | GCTCGGTAACACACGGTrCTAGCA/3SpC3/ (SEQ ID No: 117) |
| PCR19 | TACCACGCTGGCTAGCArACAACA/3SpC3/ (SEQ ID No: 118) |
| PCR20 | GCCAGCGTGGTAAGTAArCAGCAA/3SpC3/ (SEQ ID No: 119) |

Notes:
rA, rG and rC = RNA bases A, G and C, respectively; 3SpC3 = C3 spacer

Hybrid-Capture of Genomic Regions of Interest (Optional Step; Whole-Genome Sequencing does not Require Hybrid-Capture):

The purified PCR product (10 μL) was mixed with 5 μL of human Cot-1 DNA (stock of 1 μg/μL), 5 μL of blocking oligos that are complementary to the adapter sequences (20 blocking oligos total, stock of 12 μM of each oligo; oligo sequences listed in Table 5) and the mixture was left to dry overnight at 37° C. The mixture was resuspended in 15 μL of 2×IDT xGen hybridization buffer and 5 μL of IDT xGen hybridization enhancer (both from Integrated DNA Technologies) and incubated at 95° C. for 10 minutes. IDT xGen Lockdown hybrid capture probes (Integrated DNA Technologies) resuspended in 10 μL of 10 mM Tris (pH 7.5) were added and the mixture was incubated at 65° C. for 4 hours. The hybrid-capture probes were designed by Integrated DNA Technologies (IDT) to hybridize to the genomic regions of interest (typically exons of selected genes), and according to the manufacturer, they consisted of 120 nucleotide-long DNA oligonucleotides with a biotin label. The concentration of the hybrid capture probes is propriety information that IDT does not provide. During this incubation period, 100 μL of M-270 streptavidin Dynabeads (Thermo Fisher) were transferred to a microcentrifuge tube and placed on a magnetic rack. The supernatant was discarded and the beads were washed with IDT bead wash buffer (2×200 μL) and set aside. At the completion of the 4-hour hybridization period, the contents of the hybrid-capture reaction were transferred to the microcentrifuge tube containing the streptavidin Dynabeads and mixed well. The mixture was incubated at 65° C. for 45 minutes, with gentle shaking every 12 minutes to resuspend the beads. After the incubation period, 100 μL of Wash Buffer I (IDT), pre-heated to 65° C., was added to the mixture and the tube was placed on a magnetic rack. The supernatant was discarded and the beads were washed twice with Stringent Wash Buffer (2×200 μL; IDT) that was pre-heated to 65° C. The beads were subsequently washed at room temperature successively with 200 μL of Wash Buffer I, 200 μL of Wash Buffer II, and 200 μL of Wash Buffer III (all 3 buffers from IDT). After the completion of the washes, the beads were resuspended in 30 μL of 10 mM Tris (pH 7.5) and incubated at 95° C. for 2 minutes to release the hybrid-captured DNA. The tube was placed on a magnetic rack and the supernatant was transferred to a new microcentrifuge tube. To this solution containing 30 μL of purified, hybrid-captured DNA, 100 ng of carrier RNA (Qiagen) in 2 μL of water was added, followed by 60 μL of Agencourt Ampure XP beads (Beckman Coulter), and incubated for 10 minutes. The tube was placed on a magnetic rack and the supernatant was discarded. The beads were washed twice with 80% ethanol in water (2×150 μL) and left to dry for 10 minutes. The beads were resuspended in 10 μL of 10 mM Tris (pH 7.5) and incubated for 10 minutes. The tube was placed on a magnetic rack and the supernatant was transferred to a new microcentrifuge tube for post-hybrid-capture PCR amplification.

TABLE 5

| Blocking oligonucleotides used to minimize daisy-chaining during hybrid-capture | |
|---|---|
| Name | Sequence |
| Block1 | TGTTGCACTCGTAGCAATGGTGGTAGCCGCTGCTTA (SEQ ID No: 120) |
| Block2 | TGTTGCTGATCACGTTGAGGCATTGACTGATGCCGG (SEQ ID No: 121) |
| Block3 | TGTTGGACAGTTCGAGTGTAATCGCTTGCGTCGACC (SEQ ID No: 122) |
| Block4 | TGTTGGCATCACTGGCAATGACGCTCTGACCGAACT (SEQ ID No: 123) |
| Block5 | TGTTGCGTCATGTGTCACCACGACAATGGATGGTGC (SEQ ID No: 124) |
| Block6 | TGTTGCACAGTCTGCGATTGACTCCAAGCACAGCCA (SEQ ID No: 125) |
| Block7 | TGTTGGTCAAGTCGTCTTCCGACACGGACCTGAGTT (SEQ ID No: 126) |
| Block8 | TGTTGGAACTGACGATCGTCCGTGTAGCGTTCAACG (SEQ ID No: 127) |
| Block9 | TGTTGCTAGCTCAGGACACAATCGAGCTCCGATCCG (SEQ ID No: 128) |
| Block10 | TGTTGCATCGAACGTGGTTAGCCGAAGTTGCACGAG (SEQ ID No: 129) |
| Block11 | TGTTGGAGTCTATGCCAAGTGTATGAGCGGTGCGAA (SEQ ID No: 130) |
| Block12 | TGTTGGTACTGAAGGCTACGACTTGTTCAGCCACGT (SEQ ID No: 131) |
| Block13 | TGTTGCTACATCTGACGATTCAACTACGCGGACGTG (SEQ ID No: 132) |
| Block14 | TGTTGCGATGTACGAACTGCTATTCGTCGCCGATGG (SEQ ID No: 133) |
| Block15 | TGTTGGACTCATCGTACTTGTTGCGTTCCTAGCCGC (SEQ ID No: 134) |
| Block16 | TGTTGCCTAGTTGGAAGACAACCAGCATCTCGCGTC (SEQ ID No: 135) |
| Block17 | TGTTGGCTATGATGCATTGTTGGCTGGTGACCGGTA (SEQ ID No: 136) |
| Block18 | TGTTGCTCTAGTAGGCTAGACCGTGTGTTACCGAGC (SEQ ID No: 137) |
| Block19 | TGTTGGATCGACTGGTTGTTGCTAGCCAGCGTGGTA (SEQ ID No: 138) |

TABLE 5-continued

| Blocking oligonucleotides used to minimize daisy-chaining during hybrid-capture | |
|---|---|
| Name | Sequence |
| Block20 | TGTTGCATGACTGGTGCTGTTACTTACCACGCTGGC (SEQ ID No: 139) |

Post Hybrid-Capture PCR Amplification (Only Necessary if Hybrid Capture was Performed)

The captured DNA product (10 μL) was used as a template in a real-time PCR amplification (25 μL total volume) containing 5 μL of 5× Phire reaction buffer (Thermo Fisher), 0.5 μL of dNTP mix (10 mM of each dNTP), 1.5 μL SYBR Green (1× working stock in water), 2.5 μL of primer mix (20 primers total, working stock of 1 μM of each primer, listed in Table 4), 2.5 μL of RNase $H_2$ solution (working stock of 50 mU/μL; Integrated DNA Technologies), 2.5 μL of water and 0.5 μL of Phire Hot Start II DNA Polymerase (Thermo Fisher). Thermal cycling for PCR was carried out on a real-time PCR machine (Bio-Rad IQ5). The cycling parameters were as follows: 1 cycle of 98° C. for 30 seconds, then a maximum of 30 cycles of [98° C. for 10 seconds, 55° C. for 55 seconds and 72° C. for 55 seconds]. Instead of carrying out the PCR for a fixed number of cycles, the fluorescence signal was followed on the real-time PCR machine, and the tube was removed when the signal was nearing saturation (plateau phase). Typically for post-hybrid capture DNA templates, tubes were removed after ~19-21 cycles. To remove a tube, the PCR machine was paused during a 72° C. incubation period with the temperature maintained at 72° C. for at least 1 minute before removing the tube to promote complete polymerase extension on existing template DNA strands. After the completion of the PCR, 50 μL of Ampure XP beads were added to the reaction mixture and incubated for 10 minutes at room temperature. The mixture was placed on a magnetic rack to separate the beads. The supernatant was discarded, and the beads were washed twice with 80% ethanol in water (2×150 μL) and left to dry for 10 minutes. The beads were resuspended in 10 μL of 10 mM Tris (pH 7.5) off the magnetic rack and incubated for 10 minutes. The mixture was then placed back on the magnetic rack to pull the beads to the side of the tube, and the supernatant containing the PCR-amplified product was transferred to a new microcentrifuge tube.

Preparation of Sequencing Library by PCR Amplification:

The purified PCR product (either obtained without hybrid-capture or after post-hybrid capture PCR) was used as a template in a 25 μL PCR amplification reaction containing 5 μL of 5× Phire reaction buffer (Thermo Fisher), 0.5 μL of dNTP mix (10 mM of each dNTP), 2.5 μL of barcoded P5 adapter-containing primer mix (20 primers total, working stock of 1 μM of each primer; sequences listed in Table 6), 2.5 μL of barcoded P7 adapter-containing primer mix (20 primers total, working stock of 1 μM of each primer; sequences listed in Table 7), 2.5 μL of RNase H2 solution (working stock of 50 mU/μL; IDT), and 0.5 μL of Phire Hot Start II DNA Polymerase (Thermo Fisher). The cycling parameters were as follows: 1 cycle of 98° C. for 30 seconds, and 5 cycles of [98° C. for 10 seconds, 55° C. for 55 seconds, and 72° C. for 55 seconds]. After the completion of the PCR, 50 μL of Ampure XP beads were added to the reaction mixture and incubated for 10 minutes at room temperature. The mixture was placed on a magnetic rack to separate the beads. The supernatant was discarded, and the beads were washed twice with 80% ethanol in water (2×150 μL) and left to dry for 10 minutes. The beads were resuspended in 10 μL of 10 mM Tris (pH 7.5) off the magnetic rack and incubated for 10 minutes. The mixture was then placed back on the magnetic rack to pull the beads to the side of the tube, and the supernatant containing the PCR-amplified product was transferred to a new microcentrifuge tube and subsequently subjected to next-generation sequencing.

TABLE 6

| PCR primers comprising Illumina P5 adapter sequences | |
|---|---|
| Primer name | Primer sequence |
| AdapFwd1 | AATGATACGGCGACCACCGAGATCTACAC[BCF]ACACTCTTTCCCTACACG ACGCTCTTCCGATCTTAAGCAGCGGCTACCACrCATTG-XX (SEQ ID No: 140) |
| AdapFwd2 | AATGATACGGCGACCACCGAGATCTACAC[BCF]ACACTCTTTCCCTACACG ACGCTCTTCCGATCTCCGGCATCAGTCAATGCrCTCAA-XX (SEQ ID No: 141) |
| AdapFwd3 | AATGATACGGCGACCACCGAGATCTACAC[BCF]ACACTCTTTCCCTACACG ACGCTCTTCCGATCTGGTCGACGCAAGCGATTrACACT-XX (SEQ ID No: 142) |
| AdapFwd4 | AATGATACGGCGACCACCGAGATCTACAC[BCF]ACACTCTTTCCCTACACG ACGCTCTTCCGATCTAGTTCGGTCAGAGCGTCrATTGC-XX (SEQ ID No: 143) |
| AdapFwd5 | AATGATACGGCGACCACCGAGATCTACAC[BCF]ACACTCTTTCCCTACACG ACGCTCTTCCGATCTGCACCATCCATTGTCGTrGGTGA-XX (SEQ ID No: 144) |
| AdapFwd6 | AATGATACGGCGACCACCGAGATCTACAC[BCF]ACACTCTTTCCCTACACG ACGCTCTTCCGATCTTGGCTGTGCTTGGAGTCrAATCG-XX (SEQ ID No: 145) |
| AdapFwd7 | AATGATACGGCGACCACCGAGATCTACAC[BCF]ACACTCTTTCCCTACACG ACGCTCTTCCGATCTAACTCAGGTCCGTGTCGrGAAGA-XX (SEQ ID No: 146) |
| AdapFwd8 | AATGATACGGCGACCACCGAGATCTACAC[BCF]ACACTCTTTCCCTACACG ACGCTCTTCCGATCTCGTTGAACGCTACACGGrACGAT-XX (SEQ ID No: 147) |
| AdapFwd9 | AATGATACGGCGACCACCGAGATCTACAC[BCF]ACACTCTTTCCCTACACG ACGCTCTTCCGATCTCGGATCGGAGCTCGATTrGTGTC-XX (SEQ ID No: 148) |

TABLE 6-continued

| PCR primers comprising Illumina P5 adapter sequences | |
|---|---|
| Primer name | Primer sequence |
| AdapFwd10 | AATGATACGGCGACCACCGAGATCTACAC[BCF]ACACTCTTTCCCTACACG ACGCTCTTCCGATCTCTCGTGCAACTTCGGCTrAACCA-XX (SEQ ID No: 149) |
| AdapFwd11 | AATGATACGGCGACCACCGAGATCTACAC[BCF]ACACTCTTTCCCTACACG ACGCTCTTCCGATCTTTCGCACCGCTCATACArCTTGG-XX (SEQ ID No: 150) |
| AdapFwd12 | AATGATACGGCGACCACCGAGATCTACAC[BCF]ACACTCTTTCCCTACACG ACGCTCTTCCGATCTACGTGGCTGAACAAGTCrGTAGC-XX (SEQ ID No: 151) |
| AdapFwd13 | AATGATACGGCGACCACCGAGATCTACAC[BCF]ACACTCTTTCCCTACACG ACGCTCTTCCGATCTCACGTCCGCGTAGTTGArATCGT-XX (SEQ ID No: 152) |
| AdapFwd14 | AATGATACGGCGACCACCGAGATCTACAC[BCF]ACACTCTTTCCCTACACG ACGCTCTTCCGATCTCCATCGGCGACGAATAGrCAGTT-XX (SEQ ID No: 153) |
| AdapFwd15 | AATGATACGGCGACCACCGAGATCTACAC[BCF]ACACTCTTTCCCTACACG ACGCTCTTCCGATCTGCGGCTAGGAACGCAACrAAGTA-XX (SEQ ID No: 154) |
| AdapFwd16 | AATGATACGGCGACCACCGAGATCTACAC[BCF]ACACTCTTTCCCTACACG ACGCTCTTCCGATCTGACGCGAGATGCTGGTTrGTCTT-XX (SEQ ID No: 155) |
| AdapFwd17 | AATGATACGGCGACCACCGAGATCTACAC[BCF]ACACTCTTTCCCTACACG ACGCTCTTCCGATCTTACCGGTCACCAGCCAArCAATG-XX (SEQ ID No: 156) |
| AdapFwd18 | AATGATACGGCGACCACCGAGATCTACAC[BCF]ACACTCTTTCCCTACACG ACGCTCTTCCGATCTGCTCGGTAACACACGGTrCTAGC-XX (SEQ ID No: 157) |
| AdapFwd19 | AATGATACGGCGACCACCGAGATCTACAC[BCF]ACACTCTTTCCCTACACG ACGCTCTTCCGATCTTACCACGCTGGCTAGCArACAAC-XX (SEQ ID No: 158) |
| AdapFwd20 | AATGATACGGCGACCACCGAGATCTACAC[BCF]ACACTCTTTCCCTACACG ACGCTCTTCCGATCTGCCAGCGTGGTAAGTAArCAGCA-XX (SEQ ID No: 159) |

Notes:
[BCF] = Forward sample barcode; rA, rG and rC = A, G, C RNA bases; X = inverse dA (Glen Research #10-0001-02 and #20-0012-42). Each sample-specific barcode was 8 nucleotides long and differed from all other barcodes at a minimum of 2 positions.

TABLE 7

| PCR primers comprising Illumina P7 adapter sequences | |
|---|---|
| Primer name | Primer sequence |
| AdapRev1 | CAAGCAGAAGACGGCATACGAGAT[BCR]GTGACTGGAGTTCAGACGTGTG CTCTTCCGATCTTAAGCAGCGGCTACCACrCATTG-XX (SEQ ID No: 160) |
| AdapRev2 | CAAGCAGAAGACGGCATACGAGAT[BCR]GTGACTGGAGTTCAGACGTGTG CTCTTCCGATCTCCGGCATCAGTCAATGCrCTCAA-XX (SEQ ID No: 161) |
| AdapRev3 | CAAGCAGAAGACGGCATACGAGAT[BCR]GTGACTGGAGTTCAGACGTGTG CTCTTCCGATCTGGTCGACGCAAGCGATTrACACT-XX (SEQ ID No: 162) |
| AdapRev4 | CAAGCAGAAGACGGCATACGAGAT[BCR]GTGACTGGAGTTCAGACGTGTG CTCTTCCGATCTAGTTCGGTCAGAGCGTCrATTGC-XX (SEQ ID No: 163) |
| AdapRev5 | CAAGCAGAAGACGGCATACGAGAT[BCR]GTGACTGGAGTTCAGACGTGTG CTCTTCCGATCTGCACCATCCATTGTCGTrGGTGA-XX (SEQ ID No: 164) |
| AdapRev6 | CAAGCAGAAGACGGCATACGAGAT[BCR]GTGACTGGAGTTCAGACGTGTG CTCTTCCGATCTTGGCTGTGCTTGGAGTCrAATCG-XX (SEQ ID No: 165) |
| AdapRev7 | CAAGCAGAAGACGGCATACGAGAT[BCR]GTGACTGGAGTTCAGACGTGTG CTCTTCCGATCTAACTCAGGTCCGTGTCGrGAAGA-XX (SEQ ID No: 166) |
| AdapRev8 | CAAGCAGAAGACGGCATACGAGAT[BCR]GTGACTGGAGTTCAGACGTGTG CTCTTCCGATCTCGTTGAACGCTACACGGrACGAT-XX (SEQ ID No: 167) |
| AdapRev9 | CAAGCAGAAGACGGCATACGAGAT[BCR]GTGACTGGAGTTCAGACGTGTG CTCTTCCGATCTCGGATCGGAGCTCGATTrGTGTC-XX (SEQ ID No: 168) |
| AdapRev10 | CAAGCAGAAGACGGCATACGAGAT[BCR]GTGACTGGAGTTCAGACGTGTG CTCTTCCGATCTCTCGTGCAACTTCGGCTrAACCA-XX (SEQ ID No: 169) |

TABLE 7-continued

| PCR primers comprising Illumina P7 adapter sequences | |
|---|---|
| Primer name | Primer sequence |
| AdapRev11 | CAAGCAGAAGACGGCATACGAGAT[BCR]GTGACTGGAGTTCAGACGTGTG CTCTTCCGATCTTTCGCACCGCTCATACArCTTGG-XX (SEQ ID No: 170) |
| AdapRev12 | CAAGCAGAAGACGGCATACGAGAT[BCR]GTGACTGGAGTTCAGACGTGTG CTCTTCCGATCTACGTGGCTGAACAAGTCrGTAGC-XX (SEQ ID No: 171) |
| AdapRev13 | CAAGCAGAAGACGGCATACGAGAT[BCR]GTGACTGGAGTTCAGACGTGTG CTCTTCCGATCTCACGTCCGCGTAGTTGArATCGT-XX (SEQ ID No: 172) |
| AdapRev14 | CAAGCAGAAGACGGCATACGAGAT[BCR]GTGACTGGAGTTCAGACGTGTG CTCTTCCGATCTCCATCGGCGACGAATAGrCAGTT-XX (SEQ ID No: 173) |
| AdapRev15 | CAAGCAGAAGACGGCATACGAGAT[BCR]GTGACTGGAGTTCAGACGTGTG CTCTTCCGATCTGCGGCTAGGAACGCAACrAAGTA-XX (SEQ ID No: 174) |
| AdapRev16 | CAAGCAGAAGACGGCATACGAGAT[BCR]GTGACTGGAGTTCAGACGTGTG CTCTTCCGATCTGACGCGAGATGCTGGTTrGTCTT-XX (SEQ ID No: 175) |
| AdapRev17 | CAAGCAGAAGACGGCATACGAGAT[BCR]GTGACTGGAGTTCAGACGTGTG CTCTTCCGATCTTACCGGTCACCAGCCAArCAATG-XX (SEQ ID No: 176) |
| AdapRev18 | CAAGCAGAAGACGGCATACGAGAT[BCR]GTGACTGGAGTTCAGACGTGTG CTCTTCCGATCTGCTCGGTAACACACGGTrCTAGC-XX (SEQ ID No: 177) |
| AdapRev19 | CAAGCAGAAGACGGCATACGAGAT[BCR]GTGACTGGAGTTCAGACGTGTG CTCTTCCGATCTTACCACGCTGGCTAGCArACAAC-XX (SEQ ID No: 178) |
| AdapRev20 | CAAGCAGAAGACGGCATACGAGAT[BCR]GTGACTGGAGTTCAGACGTGTG CTCTTCCGATCTGCCAGCGTGGTAAGTAArCAGCA-XX (SEQ ID No: 179) |

Notes:
[BCR] = Reverse sample barcode; rA, rG and rC = A, G, C RNA bases; X = inverse dA (Glen Research #10-0001-02 and #20-0012-42). Each sample-specific barcode was 8 nucleotides long and differed from all otherbarcodes at a minimum of 2 positions.

Next-Generation Sequencing and Sequence Analysis:

The purified PCR products with P5 and P7 adapters incorporated were prepared for next-generation sequencing by measuring the concentration of DNA using an Agilent Bioanalyzer, and using quantitative PCR. The DNA was then diluted to the concentration recommended for loading onto an Illumina HiSeq 2500 flow cell (according to the manufacturer's specifications). Cluster formation was carried out on the flow cell according to Illumina's protocol. The sample was loaded onto a single lane of a flow cell. The sequencing was performed on a HiSeq® 2500 instrument in paired-end mode, with a read length of 150 base pairs in each direction (2×150 bp mode). Two index reads were also performed, with read lengths of 8 bases each. Several samples could be sequenced in a multiplexed fashion on a single lane of a flow cell by using a dual-index labeling scheme.

The sequence output from the Illumina sequencer was analyzed according to the following general scheme. First, each read-pair from a given cluster was joined by overlapping the 3'-regions to re-create a full sequence of a DNA insert fragment. Any read-pairs that did not have perfect sequence agreement in their overlapping 3'-regions (imperfect complementarity) were discarded because the discrepancy was likely arising from a sequencer error. The adapter sequences were identified at the two ends of the reconstructed insert sequence, and these adapter sequences were trimmed to yield a genomic insert sequence. For each genomic insert sequence, a note was made of which adapter was trimmed from each end (among 20 possible adapters), and which base was present at the adapter's mismatch position (to indicate whether the adapter was attached to the top or the bottom strand of the insert DNA fragment). Because 20 different adapters were used simultaneously in the ligation reaction, the number of possible adapter combinations on both sides of the genomic DNA insert was 20×20=400. Sequences that were likely to be arising from the same strand of a given genomic DNA fragment (PCR duplicates) could be identified if they had the same combination of adapters on both ends, the same bases at the mismatch positions, and they mapped to exactly the same position on the reference genome. Such replicate sequences were grouped together to form a single-strand family. Each single-strand family consisted of sequences that were likely arising from one strand of a DNA fragment. A family was excluded from consideration if it did not contain at least 3 replicate sequences. A single-strand consensus sequence (SSCS) was then generated from each single-strand family based on the most common base read at each sequence position. Five additional bases were trimmed from both 5' and 3' ends of the SSCS to eliminate any artifacts introduced into the genomic insert DNA during the enzymatic end-repair and adapter-ligation process. If an SSCS mapped to the same position on the reference genome as another SSCS, and the two SSCSs had were attached to the same combination of adapters, but the bases at the mismatch positions of the adapters differed, then those two SSCSs were considered to be arising from opposite strands of the same insert DNA fragment. Two such SSSCs arising from opposite strands of the same insert DNA fragment were referred to as paired SSCSs. If paired SSCSs had exactly the same sequence, this became known as a double-strand consensus sequence (DSCS). Such DSCSs were aligned to the reference genome, and any variations from the reference genome were tabulated. Variations determined in this way were highly likely to be arising from true DNA mutations or polymorphisms, and were extremely unlikely to be arising from artifacts of DNA damage, PCR errors, or sequencer errors.

Example 6

In this example, we use the concept of comparing sequences derived from paired-strands of individual double-stranded DNA fragments to improve the analysis of epigenetic modifications on DNA.

End Repair of Double-Stranded DNA Fragments and Ligation of Adapters:

In this example, DNA for analysis was obtained from the plasma of patient lung cancer, and from healthy volunteers. DNA was extracted from 1 mL of EDTA-plasma, using the methods that were detailed in Example 1. The yield of cell-free DNA from 1 mL of patient plasma was generally in the range of approximately 5-10 ng. To prepare the ends of the insert DNA molecules for ligation of adapters, the insert DNA (approximately 5-10 ng of DNA in 50 μL of 10 mM Tris, pH 7.5) was added to 7 μL of NEBNext Ultra II End Prep Reaction buffer and 3 μL of NEBNext Ultra II End Prep Enzyme Mix (both obtained from New England Biolabs). The solution was mixed well and incubated at 20° C. for 30 minutes, followed by 65° C. for 30 minutes. After the completion of the end-preparation reaction, ligation of adapters to DNA fragments was achieved by the addition of 2.5 μL of EM-Seq adapters, 30 μL of NEBNext Ultra II Ligation Master Mix and 1 μL of NEBNext Ligation Enhancer (all from New England Biolabs). The cocktail was mixed and was incubated at 20° C. for 15 minutes.

To purify the DNA, 110 μl of resuspended NEBNext Sample Purification Beads were added to each sample. Samples were mixed well, and incubated at room temperature for 5 minutes. A magnet was used to separate the beads from the supernatant. The supernatant was discarded. The beads where then washed with 200 μl of 80% freshly prepared ethanol while in the magnetic stand. The supernatant was again discarded. The wash was repeated again for a total of 2 washes. The beads were air dried for 2 minutes at room temperature. To elute the DNA, the tubes were removed from the magnetic stand and 29 μl of Elution Buffer was added. After mixing, the tubes were placed back on the magnetic stand, and the supernatant containing the purified DNA was transferred to a new tube (volume 28 μl).

Conversion of Ligated DNA:

The following steps were carried out according to the directions in the NEB Enzymatic Methyl Seq protocol: (1) oxidation of 5-Methylcytosines and 5-Hydroxymethylcytosines using TET2 enzyme, (2) clean-up of TET2 converted DNA, (3) Denaturation of DNA using sodium hydroxide, (4) deamination of cytosines using APOBEC enzyme, and (5) clean-up of deaminated DNA. The volume of cleaned-up, converted DNA was 20 μl.

PCR Amplification and Library Quantification:

According to the directions in the NEB Enzymatic Methyl Seq protocol, the following steps were performed: (1) PCR amplification using NEBNext Q5U polymerase, which is designed to tolerate the presence of deoxy-uracils in the template DNA (2) clean-up of amplified DNA, and (3) quantification of the resulting sequencing library using an Agilent Bioanalyzer and quantitative PCR.

Next-Generation Sequencing:

The quantified sequencing library was diluted to the concentration recommended for loading onto an Illumina HiSeq 2500 flow cell (according to the manufacturer's specifications). Cluster formation was carried out on the flow cell according to Illumina's protocol. The multiplexed, indexed samples were loaded onto a single lane of a flow cell. The sequencing was performed on a HiSeq® 2500 instrument in paired-end mode, with a read length of 150 base pairs in each direction (2×150 bp mode). Two index reads were also performed, with read lengths of 8 bases each.

Sequence Analysis:

The sequences from the Illumina sequencer were subjected to standard quality filters and then paired-end sequences were joined and adapter sequences were trimmed to yield full-length, converted insert sequences. After removing sequences of inserts that were shorter than 50 base pairs, the converted sequences were transformed to purine (R) and pyrimidine (Y) notation. Sequences were grouped together if they had exactly the same sequence in R/Y notation, indicating that they were derived from either strand of an individual double-stranded DNA fragment. Because cytosine to thymine conversion from the (+) strand would produce a different sequence pattern than cytosine to thymine conversion from the (−) strand, it was possible to differentiate converted sequences derived from the two paired strands within each sequence group. A group was only considered for the next reconstruction step if it contained at least one sequence derived from each of the two paired strands of the double-stranded DNA fragment. Finally, to reconstruct or decode the base sequence and the methylation or hydroxymethylation sites in the original, patient-derived double-stranded DNA fragments, we used a decoding scheme as shown in Table 8. This approach enabled reconstruction of the 4-letter DNA code in the original DNA fragments (by disambiguation of cytosines that were converted to thymines versus thymines that remained thymines). This approach also enabled identification of methylated or hydroxymethylated cytosines on both strands of the original DNA fragments. Importantly, this was able to be performed without requiring comparison to a reference genomic sequence.

TABLE 8

Table 8: Example scheme for reconstructing sequence and epigenetic modifications in original double-stranded DNA fragments from paired-strand converted sequences.

| | Base | | | | | |
|---|---|---|---|---|---|---|
| Converted reference strand base | T | T | C | G | A | G |
| Converted opposite strand base | G | A | G | C | T | T |
| Reconstructed original sequence of reference strand | C | T | *C | *G | A | G |

Note:
*C = modified cytosine (e.g., 5-methylcytosine or 5-hydroxymethylcytosine)
*G = Guanine base on reference strand that has a modified cytosine on the opposite strand.

Although the present invention has been described in terms of particular embodiments, it is not intended that the invention be limited to these embodiments. Modifications within the spirit of the invention will be apparent to those skilled in the art. It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A method of deducing base sequences and epigenetic modifications of a plurality of DNA fragments based on comparison of converted sequences derived from opposite, paired strands of individual double-stranded DNA fragments without requiring comparison to an external reference genomic sequence, the method comprising:

attaching adapter molecules to both paired DNA strands of individual double-stranded DNA fragments from among a plurality of DNA fragments;

converting cytosine bases in the DNA strands to uracil bases, wherein conversion efficiency depends on presence or absence of an epigenetic modification on the cytosine base;

using a polymerase chain reaction to generate copies of the converted DNA strands, wherein uracil bases in a template converted DNA strand may be replaced by thymine bases in a converted DNA copy;

sequencing the converted DNA copies to generate converted sequences;

forming sequence groups based on sequence features of the adapters and/or the converted DNA copies, wherein a sequence group comprises converted sequences derived from paired strands of an individual double-stranded DNA fragment;

comparing converted sequences derived from opposite, paired strands of individual double-stranded DNA fragments within each sequence group to deduce pre-conversion sequences of cytosine, thymine, epigenetically modified cytosine, adenine, and guanine bases in the plurality of DNA fragments; and generating an error-corrected consensus sequence including epigenetic modifications solely from the paired converted sequences, without a need for external reference sequence alignment.

2. The method of claim 1, wherein the epigenetic modification is 5-methylcytosine.

3. The method of claim 1, wherein the epigenetic modification is 5-hydroxymethylcytosine.

4. The method of claim 1, wherein the adapters comprise DNA sequences of sufficient diversity to permit ligated molecules to be distinguished from each other.

5. The method of claim 1, wherein the adapter comprises 5-methylcytosine and/or 5-hydroxymethylcytosine bases to prevent conversion to uracil or thymine.

6. The method of claim 1, wherein the conversion of cytosines is mediated by a chemical reaction comprising sodium bisulfite.

7. The method of claim 1, wherein the conversion of cytosines is mediated by enzymatic reactions comprising any of APOBEC, TET1, TET2, T4-beta-galactosidase.

8. The method of claim 1, wherein the lack of requirement for comparison to an external reference genomic sequence enables deducing base sequences and epigenetic modifications of a plurality of DNA fragments from any source of genomic DNA, including sources for which a reference sequence has not been established.

9. The method of claim 1, wherein grouping of converted sequences derived from paired strands of an individual double-stranded DNA fragment is based on the sequences having a common purine/pyrimidine base sequence (after reverse-complementation).

* * * * *

SEQUENCE LISTING

<160> NUMBER OF SEQ ID NOS: 179

<210> SEQ ID NO 1
<211> LENGTH: 24
<212> TYPE: DNA
<213> ORGANISM: Artificial Sequence
<220> FEATURE:
<223> OTHER INFORMATION: synthetic construct

<400> SEQUENCE: 1
attgtatcgt aatggtattg agtg 24

<210> SEQ ID NO 2
<211> LENGTH: 24
<212> TYPE: DNA
<213> ORGANISM: Artificial Sequence
<220> FEATURE:
<223> OTHER INFORMATION: synthetic construct

<400> SEQUENCE: 2
ryyryryyry rryrryryyr rryr 24

<210> SEQ ID NO 3
<211> LENGTH: 24
<212> TYPE: DNA
<213> ORGANISM: Artificial Sequence
<220> FEATURE:
<223> OTHER INFORMATION: synthetic construct

<400> SEQUENCE: 3
attacatcgt aataacatca aata 24

<210> SEQ ID NO 4
<211> LENGTH: 24
<212> TYPE: DNA
<213> ORGANISM: Artificial Sequence
<220> FEATURE:
<223> OTHER INFORMATION: synthetic construct

<400> SEQUENCE: 4
ryyryryyry rryrryryyr rryr 24

<210> SEQ ID NO 5
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (56)..(56)
<223> OTHER INFORMATION: This position is RNA

<400> SEQUENCE: 5
ctacacgacg ctcttccgat ctnnnnnnna ggcctgctga aaatgactga atataaactt 60

<210> SEQ ID NO 6
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (56)..(56)
<223> OTHER INFORMATION: This position is RNA

<400> SEQUENCE: 6
ctacacgacg ctcttccgat ctnnnnnnnc ctcacagtaa aaataggtga ttttggtcta 60

<210> SEQ ID NO 7
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (49)..(49)
<223> OTHER INFORMATION: This position is RNA

<400> SEQUENCE: 7
ctacacgacg ctcttccgat ctnnnnnnng actcccaggt acttccggaa cct 53

<210> SEQ ID NO 8
<211> LENGTH: 57
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (53)..(53)
<223> OTHER INFORMATION: This position is RNA

<400> SEQUENCE: 8
ctacacgacg ctcttccgat ctnnnnnnnc agctcaaagc aatttctaca cgagatc 57

<210> SEQ ID NO 9
<211> LENGTH: 58
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (54)..(54)
<223> OTHER INFORMATION: This position is RNA

<400> SEQUENCE: 9
ctacacgacg ctcttccgat ctnnnnnnng caagaggctt tggagtattt catgaaac 58

<210> SEQ ID NO 10
<211> LENGTH: 59
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (55)..(55)
<223> OTHER INFORMATION: This position is RNA

<400> SEQUENCE: 10
ctacacgacg ctcttccgat ctnnnnnnng gatcccagaa ggtgagaaag ttaaaattc 59

<210> SEQ ID NO 11
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (50)..(50)
<223> OTHER INFORMATION: This position is RNA

<400> SEQUENCE: 11
ctacacgacg ctcttccgat ctnnnnnnna aaacaccgca gcatgtcaag atca 54

<210> SEQ ID NO 12
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (47)..(47)
<223> OTHER INFORMATION: This position is RNA

<400> SEQUENCE: 12
ctacacgacg ctcttccgat ctnnnnnnnc atctgcctca cctccaccgt g 51

<210> SEQ ID NO 13
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (52)..(52)
<223> OTHER INFORMATION: This position is RNA

<400> SEQUENCE: 13
cagacgtgtg ctcttccgat ctnnnnnnnc tgaattagct gtatcgtcaa ggcact 56

<210> SEQ ID NO 14
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (50)..(50)
<223> OTHER INFORMATION: This position is RNA

<400> SEQUENCE: 14
cagacgtgtg ctcttccgat ctnnnnnnna ctgttcaaac tgatgggacc cact 54

<210> SEQ ID NO 15
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (47)..(47)
<223> OTHER INFORMATION: This position is RNA

<400> SEQUENCE: 15
cagacgtgtg ctcttccgat ctnnnnnnnc ttggcaaact cccccagctt g 51

<210> SEQ ID NO 16
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (52)..(52)
<223> OTHER INFORMATION: This position is RNA

<400> SEQUENCE: 16
cagacgtgtg ctcttccgat ctnnnnnnna tctccatttt agcacttacc tgtgac 56

<210> SEQ ID NO 17
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (52)..(52)
<223> OTHER INFORMATION: This position is RNA

<400> SEQUENCE: 17
cagacgtgtg ctcttccgat ctnnnnnnnt caatgcatgc tgtttaattg tgtgga 56

<210> SEQ ID NO 18
<211> LENGTH: 54
<212> TYPE: DNA
<213> ORGANISM: Artificial Sequence
<220> FEATURE:

<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (50)..(50)
<223> OTHER INFORMATION: This position is RNA

<400> SEQUENCE: 18
cagacgtgtg ctcttccgat ctnnnnnnna gcagaaactc acatcgagga tttc 54

<210> SEQ ID NO 19
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (51)..(51)
<223> OTHER INFORMATION: This position is RNA

<400> SEQUENCE: 19
cagacgtgtg ctcttccgat ctnnnnnnnt gcctccttct gcatggtatt ctttc 55

<210> SEQ ID NO 20
<211> LENGTH: 55
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(29)
<223> OTHER INFORMATION: n is a, c, g, or t
<220> FEATURE:
<221> NAME/KEY: misc_feature
<222> LOCATION: (51)..(51)
<223> OTHER INFORMATION: This position is RNA

<400> SEQUENCE: 20
cagacgtgtg ctcttccgat ctnnnnnnna gccaatattg tctttgtgtt cccgg 55

<210> SEQ ID NO 21
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (29)..(29)
<223> OTHER INFORMATION: This position is RNA

<400> SEQUENCE: 21
acactctttc cctacacgac gctcttccga tct 33

<210> SEQ ID NO 22
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(30)
<223> OTHER INFORMATION: This position is RNA

<400> SEQUENCE: 22
gtgactggag ttcagacgtg tgctcttccg atct 34

<210> SEQ ID NO 23
<211> LENGTH: 70
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (66)..(66)
<223> OTHER INFORMATION: This position is RNA

<400> SEQUENCE: 23
aatgatacgg cgaccaccga gatctacacn nnnnnnnaca ctctttccct acacgacgct 60
cttccgatct 70

<210> SEQ ID NO 24
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (62)..(62)
<223> OTHER INFORMATION: This position is RNA

<400> SEQUENCE: 24
caagcagaag acggcatacg agatnnnnnn nngtgactgg agttcagacg tgtgctcttc 60
cgatct 66

<210> SEQ ID NO 25
<211> LENGTH: 67
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(39)
<223> OTHER INFORMATION: stretch of n's represents a barcode positions, where each barcode in the set differs from all other barcodes in the set by at least two bases

<400> SEQUENCE: 25
aatgatacgg cgaccaccga gatctacacn nnnnnnnnna cactctttcc ctacacgacg 60
ctcttcc 67

<210> SEQ ID NO 26
<211> LENGTH: 77
<212> TYPE: DNA

<213> ORGANISM: Artificial Sequence
<220> FEATURE:
<223> OTHER INFORMATION: synthetic construct
<220> FEATURE:
<221> NAME/KEY: misc_feature
<222> LOCATION: (39)..(48)
<223> OTHER INFORMATION: stretch of n's represents a bead-specific
barcode

<400> SEQUENCE: 26 ttttttttt ggaagagcgt cgtgtaggga aagagtgtnn nnnnnnnngt gtagatctcg 60
gtggtcgccg tatcatt 77

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
aatgatacgg cgaccaccga gatc 24

<210> SEQ ID NO 28
<211> LENGTH: 67
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(39)
<223> OTHER INFORMATION: n is a, c, g, or t
<220> FEATURE:
<221> NAME/KEY: misc_feature
<222> LOCATION: (30)..(39)
<223> OTHER INFORMATION: stretch of n's represents a compartment-
specific barcode

<400> SEQUENCE: 28
aatgatacgg cgaccaccga gatctacacn nnnnnnnnna cactctttcc ctacacgacg 60
ctcttcc 67

<210> SEQ ID NO 29
<211> LENGTH: 67
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(39)
<223> OTHER INFORMATION: n is a, c, g, or t

<400> SEQUENCE: 29
aatgatacgg cgaccaccga gatctacacn nnnnnnnnna cactctttcc ctacacgacg 60
ctcttcc 67

<210> SEQ ID NO 30
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: This position is RNA

<400> SEQUENCE: 30
aatgatacgg cgaccaccga gatcta 26

<210> SEQ ID NO 31
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: This position is RNA

<400> SEQUENCE: 31
ggaagagcgt cgtgtaggga aagagt 26

<210> SEQ ID NO 32
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (55)..(55)
<223> OTHER INFORMATION: This position is RNA

<400> SEQUENCE: 32
ctactcactg ctctcgaccg tctgtwwwag gcctgctgaa aatgactgaa tataaactt 59

<210> SEQ ID NO 33
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (52)..(52)
<223> OTHER INFORMATION: This position is RNA

<400> SEQUENCE: 33
ctactcactg ctctcgaccg tctgtwwwga aacctgtctc ttggatattc tcgaca 56

<210> SEQ ID NO 34
<211> LENGTH: 58
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (54)..(54)
<223> OTHER INFORMATION: This position is RNA

<400> SEQUENCE: 34
ctactcactg ctctcgaccg tctgtwwwgg atcccagaag gtgagaaagt taaaattc 58

<210> SEQ ID NO 35
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (49)..(49)

<223> OTHER INFORMATION: This position is RNA

<400> SEQUENCE: 35
ctactcactg ctctcgaccg tctgtwwwaa aacaccgcag catgtcaaga tca 53

<210> SEQ ID NO 36
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (46)..(46)
<223> OTHER INFORMATION: This position is RNA

<400> SEQUENCE: 36
ctactcactg ctctcgaccg tctgtwwwca tctgcctcac ctccaccgtg 50

<210> SEQ ID NO 37
<211> LENGTH: 52
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (48)..(48)
<223> OTHER INFORMATION: This position is RNA

<400> SEQUENCE: 37
ctactcactg ctctcgaccg tctgtwwwtc ccaaccaagc tctcttgagg at 52

<210> SEQ ID NO 38
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (52)..(52)
<223> OTHER INFORMATION: This position is RNA

<400> SEQUENCE: 38
ctactcactg ctctcgaccg tctgtwwwca gctcaaagca atttctacac gagatc 56

<210> SEQ ID NO 39
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (49)..(49)
<223> OTHER INFORMATION: This position is RNA

<400> SEQUENCE: 39
ctactcactg ctctcgaccg tctgtwwwaa actgagcaag aggctttgga gta 53

<210> SEQ ID NO 40
<211> LENGTH: 58
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (54)..(54)
<223> OTHER INFORMATION: This position is RNA

<400> SEQUENCE: 40
ctactcactg ctctcgaccg tctgtwwwtt cttcatgaag acctcacagt aaaaatag 58

<210> SEQ ID NO 41
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (50)..(50)
<223> OTHER INFORMATION: This position is RNA

<400> SEQUENCE: 41
ctactcactg ctctcgaccg tctgtwwwtt gtgagtggat gggtaaaacc tatc 54

<210> SEQ ID NO 42
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (49)..(49)
<223> OTHER INFORMATION: This position is RNA

<400> SEQUENCE: 42
ctactcactg ctctcgaccg tctgtwwwaa attggagcat gtcgtcatgg aga 53

<210> SEQ ID NO 43
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (49)..(49)
<223> OTHER INFORMATION: This position is RNA

<400> SEQUENCE: 43
ctactcactg ctctcgaccg tctgtwwwcc cacgggaaag tggtgaagat atg 53

<210> SEQ ID NO 44
<211> LENGTH: 96
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (92)..(92)
<223> OTHER INFORMATION: This position is RNA

<400> SEQUENCE: 44
caagcagaag acggcatacg agatnnnnnn nngtgactgg agttcagacg tgtgctcttc 60
cgatctwwwc tgaattagct gtatcgtcaa ggcact 96

<210> SEQ ID NO 45
<211> LENGTH: 95
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (91)..(91)
<223> OTHER INFORMATION: This position is RNA

<400> SEQUENCE: 45
caagcagaag acggcatacg agatnnnnnn nngtgactgg agttcagacg tgtgctcttc 60
cgatctwwwc tcatgtactg gtccctcatt gcact 95

<210> SEQ ID NO 46
<211> LENGTH: 94
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (90)..(90)
<223> OTHER INFORMATION: This position is RNA

<400> SEQUENCE: 46
caagcagaag acggcatacg agatnnnnnn nngtgactgg agttcagacg tgtgctcttc 60
cgatctwwwa gcagaaactc acatcgagga tttc 94

<210> SEQ ID NO 47
<211> LENGTH: 95
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (91)..(91)
<223> OTHER INFORMATION: This position is RNA

<400> SEQUENCE: 47
caagcagaag acggcatacg agatnnnnnn nngtgactgg agttcagacg tgtgctcttc 60
cgatctwwwt gcctccttct gcatggtatt ctttc 95

<210> SEQ ID NO 48
<211> LENGTH: 95
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (91)..(91)
<223> OTHER INFORMATION: This position is RNA

<400> SEQUENCE: 48
caagcagaag acggcatacg agatnnnnnn nngtgactgg agttcagacg tgtgctcttc 60
cgatctwwwa gccaatattg tctttgtgtt cccgg 95

<210> SEQ ID NO 49
<211> LENGTH: 94
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (90)..(90)
<223> OTHER INFORMATION: This position is RNA

<400> SEQUENCE: 49
caagcagaag acggcatacg agatnnnnnn nngtgactgg agttcagacg tgtgctcttc 60
cgatctwwwa gggaccttac cttatacacc gtgc 94

<210> SEQ ID NO 50
<211> LENGTH: 96
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (92)..(92)
<223> OTHER INFORMATION: This position is RNA

<400> SEQUENCE: 50
caagcagaag acggcatacg agatnnnnnn nngtgactgg agttcagacg tgtgctcttc 60
cgatctwwwa tctccatttt agcacttacc tgtgac 96

<210> SEQ ID NO 51
<211> LENGTH: 95
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:

<221> NAME/KEY: misc_feature
<222> LOCATION: (91)..(91)
<223> OTHER INFORMATION: This position is RNA

<400> SEQUENCE: 51
caagcagaag acggcatacg agatnnnnnn nngtgactgg agttcagacg tgtgctcttc 60
cgatctwwwt ccaatccatt tttgttgtcc agcca 95

<210> SEQ ID NO 52
<211> LENGTH: 94
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (90)..(90)
<223> OTHER INFORMATION: This position is RNA

<400> SEQUENCE: 52
caagcagaag acggcatacg agatnnnnnn nngtgactgg agttcagacg tgtgctcttc 60
cgatctwwwa ctgttcaaac tgatgggacc cact 94

<210> SEQ ID NO 53
<211> LENGTH: 98
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (94)..(94)
<223> OTHER INFORMATION: This position is RNA

<400> SEQUENCE: 53
caagcagaag acggcatacg agatnnnnnn nngtgactgg agttcagacg tgtgctcttc 60
cgatctwwwc attattgcca acatgactta cttgatcc 98

<210> SEQ ID NO 54
<211> LENGTH: 94
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (90)..(90)
<223> OTHER INFORMATION: This position is RNA

<400> SEQUENCE: 54
caagcagaag acggcatacg agatnnnnnn nngtgactgg agttcagacg tgtgctcttc 60
cgatctwwwt ggctaaacgt cggtttattg tgca 94

<210> SEQ ID NO 55
<211> LENGTH: 94
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (90)..(90)
<223> OTHER INFORMATION: This position is RNA

<400> SEQUENCE: 55
caagcagaag acggcatacg agatnnnnnn nngtgactgg agttcagacg tgtgctcttc 60
cgatctwwwc ctcacattgc ccctgacaac atag 94

<210> SEQ ID NO 56
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: This position is RNA

<400> SEQUENCE: 56
aatgatacgg cgaccaccga gatctaca 28

<210> SEQ ID NO 57
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: This position is RNA

<400> SEQUENCE: 57
gtcgagagca gtgagtaggt gcgtag 26

<210> SEQ ID NO 58
<211> LENGTH: 74
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(41)
<223> OTHER INFORMATION: n is a, c, g, or t

<400> SEQUENCE: 58
aatgatacgg cgaccaccga gatctacacn nnnnnnnnnn nactacgcac ctactcactg 60
ctctcgaccg tctg 74

<210> SEQ ID NO 59

<211> LENGTH: 34
<212> TYPE: DNA
<213> ORGANISM: Artificial Sequence
<220> FEATURE:
<223> OTHER INFORMATION: primer

<400> SEQUENCE: 59
actacgcacc tactcactgc tctcgaccgt ctgt 34

<210> SEQ ID NO 60
<211> LENGTH: 37
<212> TYPE: DNA
<213> ORGANISM: Artificial Sequence
<220> FEATURE:
<223> OTHER INFORMATION: synthetic construct

<400> SEQUENCE: 60
taagcagcgg ctaccaccat tgttacgagt gcaacat 37

<210> SEQ ID NO 61
<211> LENGTH: 37
<212> TYPE: DNA
<213> ORGANISM: Artificial Sequence
<220> FEATURE:
<223> OTHER INFORMATION: synthetic construct

<400> SEQUENCE: 61
ccggcatcag tcaatgcctc aatgtgatca gcaacat 37

<210> SEQ ID NO 62
<211> LENGTH: 37
<212> TYPE: DNA
<213> ORGANISM: Artificial Sequence
<220> FEATURE:
<223> OTHER INFORMATION: synthetic construct

<400> SEQUENCE: 62
ggtcgacgca agcgattaca cttgaactgt ccaacat 37

<210> SEQ ID NO 63
<211> LENGTH: 37
<212> TYPE: DNA
<213> ORGANISM: Artificial Sequence
<220> FEATURE:
<223> OTHER INFORMATION: synthetic construct

<400> SEQUENCE: 63
agttcggtca gagcgtcatt gctagtgatg ccaacat 37

<210> SEQ ID NO 64
<211> LENGTH: 37
<212> TYPE: DNA
<213> ORGANISM: Artificial Sequence
<220> FEATURE:
<223> OTHER INFORMATION: synthetic construct

<400> SEQUENCE: 64
gcaccatcca ttgtcgtggt gatacatgac gcaacat 37

<210> SEQ ID NO 65
<211> LENGTH: 37
<212> TYPE: DNA
<213> ORGANISM: Artificial Sequence
<220> FEATURE:
<223> OTHER INFORMATION: synthetic construct

<400> SEQUENCE: 65
tggctgtgct tggagtcaat cgtagactgt gcaacat 37

<210> SEQ ID NO 66
<211> LENGTH: 37
<212> TYPE: DNA
<213> ORGANISM: Artificial Sequence
<220> FEATURE:
<223> OTHER INFORMATION: synthetic construct

<400> SEQUENCE: 66
aactcaggtc cgtgtcggaa gatgacttga ccaacat 37

<210> SEQ ID NO 67
<211> LENGTH: 37
<212> TYPE: DNA
<213> ORGANISM: Artificial Sequence
<220> FEATURE:
<223> OTHER INFORMATION: synthetic construct

<400> SEQUENCE: 67
cgttgaacgc tacacggacg attgtcagtt ccaacat 37

<210> SEQ ID NO 68
<211> LENGTH: 37
<212> TYPE: DNA
<213> ORGANISM: Artificial Sequence
<220> FEATURE:
<223> OTHER INFORMATION: synthetic construct

<400> SEQUENCE: 68
cggatcggag ctcgattgtg tcttgagcta gcaacat 37

<210> SEQ ID NO 69
<211> LENGTH: 37
<212> TYPE: DNA
<213> ORGANISM: Artificial Sequence
<220> FEATURE:
<223> OTHER INFORMATION: synthetic construct

<400> SEQUENCE: 69
ctcgtgcaac ttcggctaac catgttcgat gcaacat 37

<210> SEQ ID NO 70
<211> LENGTH: 37
<212> TYPE: DNA
<213> ORGANISM: Artificial Sequence
<220> FEATURE:
<223> OTHER INFORMATION: synthetic construct

<400> SEQUENCE: 70
ttcgcaccgc tcatacactt ggtatagact ccaacat 37

<210> SEQ ID NO 71
<211> LENGTH: 37
<212> TYPE: DNA
<213> ORGANISM: Artificial Sequence
<220> FEATURE:
<223> OTHER INFORMATION: synthetic construct

<400> SEQUENCE: 71
acgtggctga acaagtcgta gctttcagta ccaacat 37

<210> SEQ ID NO 72
<211> LENGTH: 37
<212> TYPE: DNA

<213> ORGANISM: Artificial Sequence
<220> FEATURE:
<223> OTHER INFORMATION: synthetic construct

<400> SEQUENCE: 72
cacgtccgcg tagttgaatc gttagatgta gcaacat 37

<210> SEQ ID NO 73
<211> LENGTH: 37
<212> TYPE: DNA
<213> ORGANISM: Artificial Sequence
<220> FEATURE:
<223> OTHER INFORMATION: synthetic construct

<400> SEQUENCE: 73
ccatcggcga cgaatagcag tttgtacatc gcaacat 37

<210> SEQ ID NO 74
<211> LENGTH: 37
<212> TYPE: DNA
<213> ORGANISM: Artificial Sequence
<220> FEATURE:
<223> OTHER INFORMATION: synthetic construct

<400> SEQUENCE: 74
gcggctagga acgcaacaag tatgatgagt ccaacat 37

<210> SEQ ID NO 75
<211> LENGTH: 37
<212> TYPE: DNA
<213> ORGANISM: Artificial Sequence
<220> FEATURE:
<223> OTHER INFORMATION: synthetic construct

<400> SEQUENCE: 75
gacgcgagat gctggttgtc tttcaactag gcaacat 37

<210> SEQ ID NO 76
<211> LENGTH: 37
<212> TYPE: DNA
<213> ORGANISM: Artificial Sequence
<220> FEATURE:
<223> OTHER INFORMATION: synthetic construct

<400> SEQUENCE: 76
taccggtcac cagccaacaa tgtatcatag ccaacat 37

<210> SEQ ID NO 77
<211> LENGTH: 37
<212> TYPE: DNA
<213> ORGANISM: Artificial Sequence
<220> FEATURE:
<223> OTHER INFORMATION: synthetic construct

<400> SEQUENCE: 77
gctcggtaac acacggtcta gcttactaga gcaacat 37

<210> SEQ ID NO 78
<211> LENGTH: 37
<212> TYPE: DNA
<213> ORGANISM: Artificial Sequence
<220> FEATURE:
<223> OTHER INFORMATION: synthetic construct

<400> SEQUENCE: 78
taccacgctg gctagcaaca actagtcgat ccaacat 37

<210> SEQ ID NO 79
<211> LENGTH: 37
<212> TYPE: DNA
<213> ORGANISM: Artificial Sequence
<220> FEATURE:
<223> OTHER INFORMATION: synthetic construct

<400> SEQUENCE: 79
gccagcgtgg taagtaacag catcagtcat gcaacat 37

<210> SEQ ID NO 80
<211> LENGTH: 36
<212> TYPE: DNA
<213> ORGANISM: Artificial Sequence
<220> FEATURE:
<223> OTHER INFORMATION: synthetic construct

<400> SEQUENCE: 80
tgttgcactc gtagcaatgg tggtagccgc tgctta 36

<210> SEQ ID NO 81
<211> LENGTH: 36
<212> TYPE: DNA
<213> ORGANISM: Artificial Sequence
<220> FEATURE:
<223> OTHER INFORMATION: synthetic construct

<400> SEQUENCE: 81
tgttgctgat cacgttgagg cattgactga tgccgg 36

<210> SEQ ID NO 82
<211> LENGTH: 36
<212> TYPE: DNA
<213> ORGANISM: Artificial Sequence
<220> FEATURE:
<223> OTHER INFORMATION: synthetic construct

<400> SEQUENCE: 82
tgttggacag ttcgagtgta atcgcttgcg tcgacc 36

<210> SEQ ID NO 83
<211> LENGTH: 36
<212> TYPE: DNA
<213> ORGANISM: Artificial Sequence
<220> FEATURE:
<223> OTHER INFORMATION: synthetic construct

<400> SEQUENCE: 83
tgttggcatc actggcaatg acgctctgac cgaact 36

<210> SEQ ID NO 84
<211> LENGTH: 36
<212> TYPE: DNA
<213> ORGANISM: Artificial Sequence
<220> FEATURE:
<223> OTHER INFORMATION: primer

<400> SEQUENCE: 84
tgttgcgtca tgtgtcacca cgacaatgga tggtgc 36

<210> SEQ ID NO 85
<211> LENGTH: 36
<212> TYPE: DNA
<213> ORGANISM: Artificial Sequence
<220> FEATURE:

<223> OTHER INFORMATION: synthetic construct

<400> SEQUENCE: 85
tgttgcacag tctgcgattg actccaagca cagcca 36

<210> SEQ ID NO 86
<211> LENGTH: 36
<212> TYPE: DNA
<213> ORGANISM: Artificial Sequence
<220> FEATURE:
<223> OTHER INFORMATION: synthetic construct

<400> SEQUENCE: 86
tgttggtcaa gtcgtcttcc gacacggacc tgagtt 36

<210> SEQ ID NO 87
<211> LENGTH: 36
<212> TYPE: DNA
<213> ORGANISM: Artificial Sequence
<220> FEATURE:
<223> OTHER INFORMATION: synthetic construct

<400> SEQUENCE: 87
tgttggaact gacgatcgtc cgtgtagcgt tcaacg 36

<210> SEQ ID NO 88
<211> LENGTH: 36
<212> TYPE: DNA
<213> ORGANISM: Artificial Sequence
<220> FEATURE:
<223> OTHER INFORMATION: synthetic construct

<400> SEQUENCE: 88
tgttgctagc tcaggacaca atcgagctcc gatccg 36

<210> SEQ ID NO 89
<211> LENGTH: 36
<212> TYPE: DNA
<213> ORGANISM: Artificial Sequence
<220> FEATURE:
<223> OTHER INFORMATION: synthetic construct

<400> SEQUENCE: 89
tgttgcatcg aacgtggtta gccgaagttg cacgag 36

<210> SEQ ID NO 90
<211> LENGTH: 36
<212> TYPE: DNA
<213> ORGANISM: Artificial Sequence
<220> FEATURE:
<223> OTHER INFORMATION: synthetic construct

<400> SEQUENCE: 90
tgttggagtc tatgccaagt gtatgagcgg tgcgaa 36

<210> SEQ ID NO 91
<211> LENGTH: 36
<212> TYPE: DNA
<213> ORGANISM: Artificial Sequence
<220> FEATURE:
<223> OTHER INFORMATION: synthetic construct

<400> SEQUENCE: 91
tgttggtact gaaggctacg acttgttcag ccacgt 36

<210> SEQ ID NO 92
<211> LENGTH: 36
<212> TYPE: DNA
<213> ORGANISM: Artificial Sequence
<220> FEATURE:
<223> OTHER INFORMATION: synthetic construct

<400> SEQUENCE: 92
tgttgctaca tctgacgatt caactacgcg gacgtg 36

<210> SEQ ID NO 93
<211> LENGTH: 36
<212> TYPE: DNA
<213> ORGANISM: Artificial Sequence
<220> FEATURE:
<223> OTHER INFORMATION: synthetic construct

<400> SEQUENCE: 93
tgttgcgatg tacgaactgc tattcgtcgc cgatgg 36

<210> SEQ ID NO 94
<211> LENGTH: 36
<212> TYPE: DNA
<213> ORGANISM: Artificial Sequence
<220> FEATURE:
<223> OTHER INFORMATION: synthetic construct

<400> SEQUENCE: 94
tgttggactc atcgtacttg ttgcgttcct agccgc 36

<210> SEQ ID NO 95
<211> LENGTH: 36
<212> TYPE: DNA
<213> ORGANISM: Artificial Sequence
<220> FEATURE:
<223> OTHER INFORMATION: synthetic construct

<400> SEQUENCE: 95
tgttgcctag ttggaagaca accagcatct cgcgtc 36

<210> SEQ ID NO 96
<211> LENGTH: 36
<212> TYPE: DNA
<213> ORGANISM: Artificial Sequence
<220> FEATURE:
<223> OTHER INFORMATION: synthetic construct

<400> SEQUENCE: 96
tgttggctat gatgcattgt tggctggtga ccggta 36

<210> SEQ ID NO 97
<211> LENGTH: 36
<212> TYPE: DNA
<213> ORGANISM: Artificial Sequence
<220> FEATURE:
<223> OTHER INFORMATION: synthetic construct

<400> SEQUENCE: 97
tgttgctcta gtaggctaga ccgtgtgtta ccgagc 36

<210> SEQ ID NO 98
<211> LENGTH: 36
<212> TYPE: DNA
<213> ORGANISM: Artificial Sequence
<220> FEATURE:
<223> OTHER INFORMATION: synthetic construct

<400> SEQUENCE: 98
tgttggatcg actggttgtt gctagccagc gtggta 36

<210> SEQ ID NO 99
<211> LENGTH: 36
<212> TYPE: DNA
<213> ORGANISM: Artificial Sequence
<220> FEATURE:
<223> OTHER INFORMATION: synthetic construct

<400> SEQUENCE: 99
tgttgcatga ctggtgctgt tacttaccac gctggc 36

<210> SEQ ID NO 100
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 100
taagcagcgg ctaccacrca ttga 24

<210> SEQ ID NO 101
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 101
ccggcatcag tcaatgcrct caaa 24

<210> SEQ ID NO 102
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 102
ggtcgacgca agcgattrac acta 24

<210> SEQ ID NO 103
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 103
agttcggtca gagcgtcrat tgca 24

<210> SEQ ID NO 104
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 104
gcaccatcca ttgtcgtrgg tgaa 24

<210> SEQ ID NO 105
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 105
tggctgtgct tggagtcraa tcga 24

<210> SEQ ID NO 106
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 106
aactcaggtc cgtgtcgrga agaa 24

<210> SEQ ID NO 107
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 107
cgttgaacgc tacacggrac gata 24

<210> SEQ ID NO 108
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 108
cggatcggag ctcgattrgt gtca 24

<210> SEQ ID NO 109
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 109
ctcgtgcaac ttcggctraa ccaa 24

<210> SEQ ID NO 110
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 110
ttcgcaccgc tcatacarct tgga 24

<210> SEQ ID NO 111
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 111
acgtggctga acaagtcrgt agca 24

<210> SEQ ID NO 112
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 112
cacgtccgcg tagttgarat cgta 24

<210> SEQ ID NO 113
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 113
ccatcggcga cgaatagrca gtta 24

<210> SEQ ID NO 114
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 114
gcggctagga acgcaacraa gtaa 24

<210> SEQ ID NO 115
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 115
gacgcgagat gctggttrgt ctta 24

<210> SEQ ID NO 116
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 116
taccggtcac cagccaarca atga 24

<210> SEQ ID NO 117
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 117
gctcggtaac acacggtrct agca 24

<210> SEQ ID NO 118
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 118
taccacgctg gctagcarac aaca 24

<210> SEQ ID NO 119
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: This position is RNA

<400> SEQUENCE: 119
gccagcgtgg taagtaarca gcaa 24

<210> SEQ ID NO 120
<211> LENGTH: 36
<212> TYPE: DNA
<213> ORGANISM: Artificial Sequence
<220> FEATURE:
<223> OTHER INFORMATION: synthetic construct

<400> SEQUENCE: 120
tgttgcactc gtagcaatgg tggtagccgc tgctta 36

<210> SEQ ID NO 121
<211> LENGTH: 36
<212> TYPE: DNA
<213> ORGANISM: Artificial Sequence
<220> FEATURE:
<223> OTHER INFORMATION: synthetic construct

<400> SEQUENCE: 121
tgttgctgat cacgttgagg cattgactga tgccgg 36

<210> SEQ ID NO 122
<211> LENGTH: 36
<212> TYPE: DNA
<213> ORGANISM: Artificial Sequence
<220> FEATURE:
<223> OTHER INFORMATION: synthetic construct

<400> SEQUENCE: 122
tgttggacag ttcgagtgta atcgcttgcg tcgacc 36

<210> SEQ ID NO 123
<211> LENGTH: 36
<212> TYPE: DNA
<213> ORGANISM: Artificial Sequence
<220> FEATURE:
<223> OTHER INFORMATION: synthetic construct

<400> SEQUENCE: 123
tgttggcatc actggcaatg acgctctgac cgaact 36

<210> SEQ ID NO 124
<211> LENGTH: 36
<212> TYPE: DNA
<213> ORGANISM: Artificial Sequence
<220> FEATURE:
<223> OTHER INFORMATION: synthetic construct

<400> SEQUENCE: 124
tgttgcgtca tgtgtcacca cgacaatgga tggtgc 36

<210> SEQ ID NO 125
<211> LENGTH: 36
<212> TYPE: DNA
<213> ORGANISM: Artificial Sequence
<220> FEATURE:
<223> OTHER INFORMATION: synthetic construct

<400> SEQUENCE: 125
tgttgcacag tctgcgattg actccaagca cagcca 36

<210> SEQ ID NO 126
<211> LENGTH: 36
<212> TYPE: DNA
<213> ORGANISM: Artificial Sequence
<220> FEATURE:
<223> OTHER INFORMATION: synthetic construct

<400> SEQUENCE: 126
tgttggtcaa gtcgtcttcc gacacggacc tgagtt 36

<210> SEQ ID NO 127
<211> LENGTH: 36
<212> TYPE: DNA
<213> ORGANISM: Artificial Sequence
<220> FEATURE:
<223> OTHER INFORMATION: synthetic construct

<400> SEQUENCE: 127
tgttggaact gacgatcgtc cgtgtagcgt tcaacg 36

<210> SEQ ID NO 128
<211> LENGTH: 36
<212> TYPE: DNA
<213> ORGANISM: Artificial Sequence
<220> FEATURE:
<223> OTHER INFORMATION: synthetic construct

<400> SEQUENCE: 128
tgttgctagc tcaggacaca atcgagctcc gatccg 36

<210> SEQ ID NO 129
<211> LENGTH: 36
<212> TYPE: DNA
<213> ORGANISM: Artificial Sequence
<220> FEATURE:
<223> OTHER INFORMATION: synthetic construct

<400> SEQUENCE: 129
tgttgcatcg aacgtggtta gccgaagttg cacgag 36

<210> SEQ ID NO 130
<211> LENGTH: 36
<212> TYPE: DNA
<213> ORGANISM: Artificial Sequence
<220> FEATURE:
<223> OTHER INFORMATION: synthetic construct

<400> SEQUENCE: 130
tgttggagtc tatgccaagt gtatgagcgg tgcgaa 36

<210> SEQ ID NO 131
<211> LENGTH: 36
<212> TYPE: DNA
<213> ORGANISM: Artificial Sequence
<220> FEATURE:

<223> OTHER INFORMATION: synthetic construct

<400> SEQUENCE: 131
tgttggtact gaaggctacg acttgttcag ccacgt 36

<210> SEQ ID NO 132
<211> LENGTH: 36
<212> TYPE: DNA
<213> ORGANISM: Artificial Sequence
<220> FEATURE:
<223> OTHER INFORMATION: synthetic construct

<400> SEQUENCE: 132
tgttgctaca tctgacgatt caactacgcg gacgtg 36

<210> SEQ ID NO 133
<211> LENGTH: 36
<212> TYPE: DNA
<213> ORGANISM: Artificial Sequence
<220> FEATURE:
<223> OTHER INFORMATION: synthetic construct

<400> SEQUENCE: 133
tgttgcgatg tacgaactgc tattcgtcgc cgatgg 36

<210> SEQ ID NO 134
<211> LENGTH: 36
<212> TYPE: DNA
<213> ORGANISM: Artificial Sequence
<220> FEATURE:
<223> OTHER INFORMATION: synthetic construct

<400> SEQUENCE: 134
tgttggactc atcgtacttg ttgcgttcct agccgc 36

<210> SEQ ID NO 135
<211> LENGTH: 36
<212> TYPE: DNA
<213> ORGANISM: Artificial Sequence
<220> FEATURE:
<223> OTHER INFORMATION: synthetic construct

<400> SEQUENCE: 135
tgttgcctag ttggaagaca accagcatct cgcgtc 36

<210> SEQ ID NO 136
<211> LENGTH: 36
<212> TYPE: DNA
<213> ORGANISM: Artificial Sequence
<220> FEATURE:
<223> OTHER INFORMATION: synthetic construct

<400> SEQUENCE: 136
tgttggctat gatgcattgt tggctggtga ccggta 36

<210> SEQ ID NO 137
<211> LENGTH: 36
<212> TYPE: DNA
<213> ORGANISM: Artificial Sequence
<220> FEATURE:
<223> OTHER INFORMATION: synthetic construct

<400> SEQUENCE: 137
tgttgctcta gtaggctaga ccgtgtgtta ccgagc 36

<210> SEQ ID NO 138
<211> LENGTH: 36
<212> TYPE: DNA
<213> ORGANISM: Artificial Sequence
<220> FEATURE:
<223> OTHER INFORMATION: synthetic construct

<400> SEQUENCE: 138
tgttggatcg actggttgtt gctagccagc gtggta 36

<210> SEQ ID NO 139
<211> LENGTH: 36
<212> TYPE: DNA
<213> ORGANISM: Artificial Sequence
<220> FEATURE:
<223> OTHER INFORMATION: synthetic construct

<400> SEQUENCE: 139
tgttgcatga ctggtgctgt tacttaccac gctggc 36

<210> SEQ ID NO 140
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 140
aatgatacgg cgaccaccga gatctacacn nnnnnnnaca ctctttccct acacgacgct 60
cttccgatct taagcagcgg ctaccaccat tg 92

<210> SEQ ID NO 141
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 141
aatgatacgg cgaccaccga gatctacacn nnnnnnnaca ctctttccct acacgacgct 60
cttccgatct ccggcatcag tcaatgcctc aa 92

<210> SEQ ID NO 142
<211> LENGTH: 92
<212> TYPE: DNA
<213> ORGANISM: Artificial Sequence
<220> FEATURE:
<223> OTHER INFORMATION: primer
<220> FEATURE:

```
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 142

aatgatacgg cgaccaccga gatctacacn nnnnnnnaca ctctttccct acacgacgct     60

cttccgatct ggtcgacgca agcgattaca ct                                   92


<210> SEQ ID NO 143
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 143

aatgatacgg cgaccaccga gatctacacn nnnnnnnaca ctctttccct acacgacgct     60

cttccgatct agttcggtca gagcgtcatt gc                                   92


<210> SEQ ID NO 144
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 144

aatgatacgg cgaccaccga gatctacacn nnnnnnnaca ctctttccct acacgacgct     60

cttccgatct gcaccatcca ttgtcgtggt ga                                   92


<210> SEQ ID NO 145
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
```

<222> LOCATION: (88)..(88)
<223> OTHER INFORMATION: This position is RNA

<400> SEQUENCE: 145
aatgatacgg cgaccaccga gatctacacn nnnnnnnaca ctctttccct acacgacgct 60
cttccgatct tggctgtgct tggagtcaat cg 92

<210> SEQ ID NO 146
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 146
aatgatacgg cgaccaccga gatctacacn nnnnnnnaca ctctttccct acacgacgct 60
cttccgatct aactcaggtc cgtgtcggaa ga 92

<210> SEQ ID NO 147
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 147
aatgatacgg cgaccaccga gatctacacn nnnnnnnaca ctctttccct acacgacgct 60
cttccgatct cgttgaacgc tacacggacg at 92

<210> SEQ ID NO 148
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 148
aatgatacgg cgaccaccga gatctacacn nnnnnnnaca ctctttccct acacgacgct 60
cttccgatct cggatcggag ctcgattgtg tc 92

<210> SEQ ID NO 149
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 149
aatgatacgg cgaccaccga gatctacacn nnnnnnnaca ctctttccct acacgacgct 60
cttccgatct ctcgtgcaac ttcggctaac ca 92

<210> SEQ ID NO 150
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 150
aatgatacgg cgaccaccga gatctacacn nnnnnnnaca ctctttccct acacgacgct 60
cttccgatct ttcgcaccgc tcatacactt gg 92

<210> SEQ ID NO 151
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 151
aatgatacgg cgaccaccga gatctacacn nnnnnnnaca ctctttccct acacgacgct 60
cttccgatct acgtggctga acaagtcgta gc 92

<210> SEQ ID NO 152
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 152
aatgatacgg cgaccaccga gatctacacn nnnnnnnaca ctctttccct acacgacgct     60
cttccgatct cacgtccgcg tagttgaatc gt                                   92

<210> SEQ ID NO 153
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 153
aatgatacgg cgaccaccga gatctacacn nnnnnnnaca ctctttccct acacgacgct     60
cttccgatct ccatcggcga cgaatagcag tt                                   92

<210> SEQ ID NO 154
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 154
aatgatacgg cgaccaccga gatctacacn nnnnnnnaca ctctttccct acacgacgct     60
cttccgatct gcggctagga acgcaacaag ta                                   92

<210> SEQ ID NO 155
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in

```
      the set by at least two bases
<220> FEATURE:
<221> NAME/KEY: misc_feature
<222> LOCATION: (88)..(88)
<223> OTHER INFORMATION: This position is RNA

<400> SEQUENCE: 155

aatgatacgg cgaccaccga gatctacacn nnnnnnnaca ctctttccct acacgacgct     60

cttccgatct gacgcgagat gctggttgtc tt                                   92


<210> SEQ ID NO 156
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 156

aatgatacgg cgaccaccga gatctacacn nnnnnnnaca ctctttccct acacgacgct     60

cttccgatct taccggtcac cagccaacaa tg                                   92


<210> SEQ ID NO 157
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 157

aatgatacgg cgaccaccga gatctacacn nnnnnnnaca ctctttccct acacgacgct     60

cttccgatct gctcggtaac acacggtcta gc                                   92


<210> SEQ ID NO 158
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (88)..(88)
<223> OTHER INFORMATION: This position is RNA

<400> SEQUENCE: 158
```

aatgatacgg cgaccaccga gatctacacn nnnnnnnaca ctctttccct acacgacgct 60
cttccgatct taccacgctg gctagcaaca ac 92

<210> SEQ ID NO 159
<211> LENGTH: 92
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (88)..(88)
<223> OTHER INFORMATION: This position is RNA

<400> SEQUENCE: 159
aatgatacgg cgaccaccga gatctacacn nnnnnnnaca ctctttccct acacgacgct 60
cttccgatct gccagcgtgg taagtaacag ca 92

<210> SEQ ID NO 160
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 160
caagcagaag acggcatacg agatnnnnnn nngtgactgg agttcagacg tgtgctcttc 60
cgatcttaag cagcggctac caccattg 88

<210> SEQ ID NO 161
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 161
caagcagaag acggcatacg agatnnnnnn nngtgactgg agttcagacg tgtgctcttc 60
cgatctccgg catcagtcaa tgcctcaa 88

<210> SEQ ID NO 162

<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 162
caagcagaag acggcatacg agatnnnnnn nngtgactgg agttcagacg tgtgctcttc 60
cgatctggtc gacgcaagcg attacact 88

<210> SEQ ID NO 163
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 163
caagcagaag acggcatacg agatnnnnnn nngtgactgg agttcagacg tgtgctcttc 60
cgatctagtt cggtcagagc gtcattgc 88

<210> SEQ ID NO 164
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 164
caagcagaag acggcatacg agatnnnnnn nngtgactgg agttcagacg tgtgctcttc 60
cgatctgcac catccattgt cgtggtga 88

<210> SEQ ID NO 165
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 165
caagcagaag acggcatacg agatnnnnnn nngtgactgg agttcagacg tgtgctcttc 60
cgatcttggc tgtgcttgga gtcaatcg 88

<210> SEQ ID NO 166
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 166
caagcagaag acggcatacg agatnnnnnn nngtgactgg agttcagacg tgtgctcttc 60
cgatctaact caggtccgtg tcggaaga 88

<210> SEQ ID NO 167
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 167
caagcagaag acggcatacg agatnnnnnn nngtgactgg agttcagacg tgtgctcttc 60
cgatctcgtt gaacgctaca cggacgat 88

<210> SEQ ID NO 168
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)

<223> OTHER INFORMATION: This position is RNA

<400> SEQUENCE: 168
caagcagaag acggcatacg agatnnnnnn nngtgactgg agttcagacg tgtgctcttc 60
cgatctcgga tcggagctcg attgtgtc 88

<210> SEQ ID NO 169
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 169
caagcagaag acggcatacg agatnnnnnn nngtgactgg agttcagacg tgtgctcttc 60
cgatctctcg tgcaacttcg gctaacca 88

<210> SEQ ID NO 170
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 170
caagcagaag acggcatacg agatnnnnnn nngtgactgg agttcagacg tgtgctcttc 60
cgatctttcg caccgctcat acacttgg 88

<210> SEQ ID NO 171
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 171
caagcagaag acggcatacg agatnnnnnn nngtgactgg agttcagacg tgtgctcttc 60
cgatctacgt ggctgaacaa gtcgtagc 88

<210> SEQ ID NO 172
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 172
caagcagaag acggcatacg agatnnnnnn nngtgactgg agttcagacg tgtgctcttc 60
cgatctcacg tccgcgtagt tgaatcgt 88

<210> SEQ ID NO 173
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 173
caagcagaag acggcatacg agatnnnnnn nngtgactgg agttcagacg tgtgctcttc 60
cgatctccat cggcgacgaa tagcagtt 88

<210> SEQ ID NO 174
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions, where each barcode in the set differs from all other barcodes in the set by at least two bases
<220> FEATURE:
<221> NAME/KEY: misc_feature
<222> LOCATION: (84)..(84)
<223> OTHER INFORMATION: This position is RNA

<400> SEQUENCE: 174
caagcagaag acggcatacg agatnnnnnn nngtgactgg agttcagacg tgtgctcttc 60
cgatctgcgg ctaggaacgc aacaagta 88

<210> SEQ ID NO 175
<211> LENGTH: 88
<212> TYPE: DNA
<213> ORGANISM: Artificial Sequence
<220> FEATURE:

```
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (84)..(84)
<223> OTHER INFORMATION: This position is RNA

<400> SEQUENCE: 175

caagcagaag acggcatacg agatnnnnnn nngtgactgg agttcagacg tgtgctcttc     60

cgatctgacg cgagatgctg gttgtctt                                        88


<210> SEQ ID NO 176
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (84)..(84)
<223> OTHER INFORMATION: This position is RNA

<400> SEQUENCE: 176

caagcagaag acggcatacg agatnnnnnn nngtgactgg agttcagacg tgtgctcttc     60

cgatcttacc ggtcaccagc caacaatg                                        88


<210> SEQ ID NO 177
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (84)..(84)
<223> OTHER INFORMATION: This position is RNA

<400> SEQUENCE: 177

caagcagaag acggcatacg agatnnnnnn nngtgactgg agttcagacg tgtgctcttc     60

cgatctgctc ggtaacacac ggtctagc                                        88


<210> SEQ ID NO 178
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions,
      where each barcode in the set differs from all other barcodes in
      the set by at least two bases
```

-continued

```
<220> FEATURE:
<221> NAME/KEY: misc_feature
<222> LOCATION: (84)..(84)
<223> OTHER INFORMATION: This position is RNA

<400> SEQUENCE: 178

caagcagaag acggcatacg agatnnnnnn nngtgactgg agttcagacg tgtgctcttc     60

cgatcttacc acgctggcta gcaacaac                                        88


<210> SEQ ID NO 179
<211> LENGTH: 88
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(32)
<223> OTHER INFORMATION: stretch of n's represents a barcode positions,
      where each barcode in the set differs from all other barcodes in
      the set by at least two bases
<220> FEATURE:
<221> NAME/KEY: misc_feature
<222> LOCATION: (84)..(84)
<223> OTHER INFORMATION: This position is RNA

<400> SEQUENCE: 179

caagcagaag acggcatacg agatnnnnnn nngtgactgg agttcagacg tgtgctcttc     60

cgatctgcca gcgtggtaag taacagca                                        88
```